US012527924B2

(12) United States Patent
Wuttke et al.

(10) Patent No.: US 12,527,924 B2
(45) Date of Patent: Jan. 20, 2026

(54) NEBULIZER AND CONTAINER

(71) Applicant: Boehringer Ingelheim International GmbH, Ingelheim am Rhein (DE)

(72) Inventors: Gilbert Wuttke, Ingelheim Am Rhein (DE); Herbert Graessl, Ingelheim Am Rhein (DE); Heinrich Kladders, Ingelheim Am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 961 days.

(21) Appl. No.: 16/631,667

(22) PCT Filed: Jul. 23, 2018

(86) PCT No.: PCT/EP2018/069945

§ 371 (c)(1),
(2) Date: Jan. 16, 2020

(87) PCT Pub. No.: WO2019/016409

PCT Pub. Date: Jan. 24, 2019

(65) Prior Publication Data

US 2020/0179620 A1 Jun. 11, 2020

(30) Foreign Application Priority Data

Jul. 21, 2017 (EP) .................................... 17020316
Jul. 20, 2018 (WO) ................. PCT/EP2018/069833

(51) Int. Cl.

| | |
|---|---|
| ***A61M 11/00*** | (2006.01) |
| ***A61M 15/00*** | (2006.01) |
| ***A61M 39/24*** | (2006.01) |

(52) U.S. Cl.

CPC ........ *A61M 11/007* (2014.02); *A61M 15/002* (2014.02); *A61M 15/0035* (2014.02);

(Continued)

(58) Field of Classification Search

CPC ........ A61M 11/00; A61M 11/006–007; A61M 11/02; A61M 15/00–0001;

(Continued)

(56) References Cited

U.S. PATENT DOCUMENTS 3,940,030 A 2/1976 Kondo
4,564,054 A * 1/1986 Gustavsson ........... A61J 1/2096 141/383

(Continued)

FOREIGN PATENT DOCUMENTS

CL 2020000145 A1 6/2020
CL 2020000149 A1 6/2020

(Continued)

OTHER PUBLICATIONS

International Search Report for related PCT Application No. PCT/EP2018/069947, 3 pages, dated Feb. 11, 2018.

(Continued)

*Primary Examiner* — Rachel T Sippel
*Assistant Examiner* — Jacqueline M Pinderski
(74) *Attorney, Agent, or Firm* — Calderon Safran & Wright P.C.; David S. Safran

(57) ABSTRACT

A nebulizer for nebulizing a liquid from a container, where the nebulizer includes a fluid pump for withdrawing the liquid in doses from the container and pressurizing the respective doses for nebulization. The container includes an air pump with a piston/cylinder arrangement to pressurizing the liquid in the container to help withdrawing the liquid from the container. A control valve limits the air pressure acting on the liquid.

26 Claims, 26 Drawing Sheets

(52) U.S. Cl.
CPC .... *A61M 15/0073* (2014.02); *A61M 15/0081* (2014.02); *A61M 2039/2426* (2013.01); *A61M 2205/07* (2013.01)

(58) Field of Classification Search
CPC ........... A61M 15/0065–0073; A61M 15/0081; A61M 2202/0468; A61M 2205/07; A61M 2205/273; B05B 11/00412; B05B 11/0044; B05B 11/3091; B05B 11/308; B65D 51/16; G06M 1/041; G06M 1/241
See application file for complete search history.

(56) References Cited

U.S. PATENT DOCUMENTS

| | | | | |
|---|---|---|---|---|
| 4,565,302 | A | 1/1986 | Pfeiffer | |
| 5,267,674 | A | 12/1993 | Von Schuckmann | |
| 5,833,088 | A | 11/1998 | Kladders | |
| 6,938,798 | B2 | 9/2005 | Stradella | |
| 6,988,496 | B1 * | 1/2006 | Eicher | B05B 11/0008 128/200.14 |
| 7,341,208 | B2 | 3/2008 | Eicher | |
| 7,703,454 | B2 | 4/2010 | Lee | |
| 7,819,285 | B2 | 10/2010 | Mochizuki | |
| 8,225,792 | B2 | 7/2012 | Kuriyama | |
| 8,936,177 | B2 | 1/2015 | Poulard | |
| 9,724,713 | B2 | 8/2017 | Baillet | |
| 2002/0074362 | A1 * | 6/2002 | Py | B05B 11/3092 222/398 |
| 2003/0209238 | A1 | 11/2003 | Eicher | |
| 2005/0011515 | A1 | 1/2005 | Lee | |
| 2005/0183718 | A1 * | 8/2005 | Wuttke | A61M 11/007 128/200.14 |
| 2006/0016449 | A1 | 1/2006 | Eicher | |
| 2007/0051745 | A1 | 3/2007 | Poulard | |
| 2007/0090205 | A1 | 4/2007 | Kunze | |
| 2008/0105702 | A1 | 5/2008 | Mochizuki | |
| 2008/0257915 | A1 | 10/2008 | Cecchi | |
| 2010/0083967 | A1 | 4/2010 | Kuriyama | |
| 2010/0300441 | A1 * | 12/2010 | Von Schuckmann | A61M 15/0065 128/203.15 |
| 2011/0168175 | A1 * | 7/2011 | Dunne | B65D 83/42 222/321.6 |
| 2012/0090603 | A1 * | 4/2012 | Dunne | A61M 15/0065 128/200.22 |
| 2012/0174919 | A1 | 7/2012 | Hausmann | |
| 2012/0260913 | A1 | 10/2012 | Bach | |
| 2015/0320948 | A1 | 11/2015 | Eicher | |
| 2016/0228902 | A1 * | 8/2016 | Crichton | A61M 35/00 |
| 2016/0296957 | A1 | 10/2016 | Baillet | |
| 2017/0203056 | A1 * | 7/2017 | Dunne | B05B 11/00416 |

FOREIGN PATENT DOCUMENTS

| | | | |
|---|---|---|---|
| CN | 101516451 | A | 8/2009 |
| EP | 0114617 | A2 | 8/1984 |
| EP | 1312418 | A2 | 5/2003 |
| EP | 1818108 | A1 | 8/2007 |
| EP | 2614848 | A1 | 7/2013 |
| FR | 2650763 | A1 | 2/1991 |
| JP | 2007516002 | A | 6/2007 |
| JP | 2007533356 | A | 11/2007 |
| JP | 2015127226 | A | 7/2015 |
| WO | 9606011 | A1 | 2/1996 |
| WO | 0049988 | A2 | 8/2000 |
| WO | 2004024340 | A1 | 3/2004 |
| WO | 2006016726 | A1 | 2/2006 |
| WO | 2007022898 | A1 | 3/2007 |
| WO | 2008049433 | A1 | 5/2008 |
| WO | 2009047173 | A2 | 4/2009 |
| WO | 2009103510 | A1 | 8/2009 |
| WO | 2009115200 | A1 | 9/2009 |
| WO | 2010063286 | A2 | 6/2010 |
| WO | 2010094305 | A1 | 8/2010 |
| WO | 2012160047 | A2 | 11/2012 |
| WO | 2015001281 | A1 | 1/2015 |
| WO | 2015132714 | A1 | 9/2015 |
| WO | 2015169732 | A1 | 11/2015 |
| WO | 2015169759 | A1 | 11/2015 |
| WO | 2016012102 | A1 | 1/2016 |
| WO | 2017076938 | A1 | 5/2017 |
| WO | 2017080895 | A1 | 5/2017 |
| WO | 2017129477 | A1 | 8/2017 |
| WO | 2019016409 | A2 | 1/2019 |
| WO | 2019016410 | A1 | 1/2019 |

OTHER PUBLICATIONS

International Search Report for corresponding PCT Application No. PCT/EP2018/069945, 7 pages, dated Jan. 15, 2019.

* cited by examiner

NEBULIZER AND CONTAINER

CROSS REFERENCE TO RELATED APPLICATIONS

This is a national phase application of International Application No. PCT/EP2018/069945, filed Jul. 23, 2018, which claims priority to International Application No. PCT/EP2018/069833, filed on Jul. 20, 2018; and EP 17020316.0, filed Jul. 21, 2017, the entire disclosures of which are hereby incorporated by reference.

BACKGROUND

The present invention relates to a nebulizer according to the disclosed embodiments and to a container according to disclosed embodiments.

WO 2009/047173 A2 discloses a nebulizer for nebulizing a liquid. A container can be inserted into the nebulizer. The container comprises a rigid outer casing and a bag containing multiple doses of the liquid. The container or its casing is vented so that the bag can collapse when withdrawing liquid.

The container may be constructed as described in WO 96/06011 A1 or WO 00/49988 A2.

WO 2010/094305 A1 discloses a nebulizer for nebulizing a liquid. A container can be inserted into the nebulizer. The container comprises a rigid outer casing and a collapsible bag containing multiple doses of the liquid. In order to avoid any undesired formation of vapor or gas bubbles in the bag when withdrawing liquid form the bag, the container can be pressurized by gas pressure in the casing to facilitate collapsing of the bag and withdrawal of liquid. However, this pressurization may lead to undesired leakage from the container during non-use, even if an additional valve is provided between the container and a pressure generator or fluid pump of the nebulizer. Further, the pressurization may significantly vary due to significant increase of the gas volume during liquid withdrawal and, thus, result in significant variation of the respectively withdrawn doses of liquid.

WO 2016/012102 A1 discloses a nebulizer for nebulizing a liquid. A container contains multiple doses of the liquid and can be inserted into the nebulizer. The container comprises a rigid outer casing and either a collapsible bag or a moveable fluid piston. The nebulizer comprises further a mechanism to help collapsing the bag or moving the fluid piston or pressurizing the liquid in the container, wherein the liquid is pressurized essentially only during withdrawal of liquid by applying an air pressure. According to one embodiment, the container comprises a pump piston for pressurizing air and a return spring for returning the pump piston, the pump piston being actuated by an actuation element formed by a housing part of the nebulizer. According to another embodiment, the container comprises a casing forming a cylinder into which a pump piston engages wherein the pump piston is connected with the housing part of the nebulizer. A special adaptation of known containers is required, and insertion of the container may be problematic. Further, the air pressure and, thus, the pressurization may significantly vary due to significant increase of the air volume when decreasing the liquid volume.

U.S. Pat. No. 3,940,030 A discloses a dispenser device for dispensing a liquid in a pressurized state from a container, wherein compressed air obtained by pushing a dispenser head is utilized as a propellant for the liquid.

SUMMARY

Object of the present invention is to provide a nebulizer and a container wherein withdrawal/sucking of liquid from the container is facilitated, while undesired leakage during non-use can be prevented or minimized, and/or wherein the withdrawn doses of liquid can be kept highly constant (in particular, for successive/repeated withdrawals of doses from the container) and/or precise metering is supported, and/or wherein the formation or growing of any gas bubble in the liquid can be prevented, and/or wherein a simple construction is possible.

The above object is achieved by a nebulizer according to one or more of the disclosed embodiments and/or by a container according to one or more of the disclosed embodiments.

The present invention relates to a nebulizer for nebulizing a liquid, preferably a liquid medicament, from a preferably replaceable container containing the liquid in a variable or collapsible/compressible volume formed or limited in particular by a collapsible bag or moveable fluid piston or any other construction such as a collapsible/compressible container made of diffusion-tight foils.

Preferably, the nebulizer comprises a housing part which can be detached or opened for inserting or replacing the container. Preferably, the nebulizer comprises a fluid pump or pressure generator for withdrawing the liquid (in particular a metered dose of liquid) from the container and/or for dispensing the dose of liquid. In particular, the container contains multiple doses of the liquid.

According to one aspect of the present invention, the nebulizer or its container comprises preferably an air pump for pressurizing the liquid in the container to help withdrawing the liquid in doses from the container, wherein the nebulizer or air pump comprises a control valve limiting the air pressure acting on the liquid in the container to a maximum value above the ambient pressure independently from a filling level of the container with the liquid. This supports or allows precise metering of the liquid and/or prevents any undesired leaking of liquid which could occur in case of very high pressures acting on the liquid.

According to another, independent aspect of the present invention, the container, air pump or pump piston comprises preferably a valve for controlling or limiting the air pressure acting on the liquid in the container and/or preventing any underpressure in the air pump or a pump chamber thereof. This allows a very simple construction and/or defined operation. In particular, this prevents leakage of the container due to high pressure and supports precise metering.

Preferably, a pressure pulse—in particular provided or generated by the nebulizer or air pump—acts on the variable volume or the liquid in the container at the beginning and/or during the tensioning of the nebulizer and/or withdrawal of liquid from the container. This helps withdrawing the liquid in doses from the container without forming or growing of any gas bubble within the liquid/container.

Preferably, the nebulizer or air pump comprises an inlet valve preventing any underpressure in the air pump or its pump chamber. This supports precise metering and can prevent any negative force acting on the liquid in the container during nebulization.

Preferably, the control valve and the inlet valve are formed by same valve or valve element. This allows a very simple construction.

According to a further, independent aspect of the present invention, the nebulizer or air pump comprises a pressure relief means to control and/or limit the air pressure within the air pump or its pump chamber and/or to decrease the air pressure acting on the liquid in the container, preferably dependent on the (axial) position of the container within the nebulizer or housing part, i.e. when a certain (axial) position of the container within the nebulizer is reached, and/or independent from the (actual) pressure in the air pump or its pump chamber and/or independent from the velocity of tensioning/cocking/loading of the nebulizer.

Preferably, the pressure relief means is embodied as a bypass channel integrated into the air pump, in particular its pump piston or cylinder, preferably wherein the bypass channel is openable when a predefined (axial) position of the pump piston within the cylinder is reached.

The pressure relief means helps to protect the nebulizer and/or container against damages that might be caused by a high air pressure maintained in the nebulizer, in particular in the pump chamber, and/or to prevent leakage of the nebulizer, e.g. after tensioning of the nebulizer without immediate nebulization. The pressure relief means ensures that the nebulizer is always pressure-neutral after tensioning, even if the nebulizer is not used/activated after tensioning.

Preferably, the air pump is arranged in and/or integrated into the nebulizer. Mostly preferred, the nebulizer, in particular its housing part or an insert therein, and the container form together the air pump. In particular, the air pump or its pump chamber can be arranged—at least partially—within the container.

According to another, independent aspect of the present invention, the container comprises an air pump including a pump piston and a return spring, preferably wherein the return spring is arranged between the pump piston and the variable or collapsible/compressible volume of the container. This allows a very compact construction wherein the filling volume of the container with liquid can be optimized. Further, this secures defined returning of the pump piston into its non-actuated position which also supports a defined operation and precise metering.

According to another, independent aspect of the present invention, the container, air pump or pump piston comprises preferably an actuation element for actuating the pump piston. This allows a very simple construction and facilitates insertion/replacement of the container as the container forms an assembly together with the air pump and actuation element.

Preferably, the air pump comprises or forms a piston/cylinder arrangement for temporarily pressurizing air in the container and/or for pressurizing the liquid in the container to help withdrawing the liquid in doses from the container. This allows a very simple construction of the air pump.

Preferably, the container comprises an inner container (which is flexible/compressible/collapsible, preferably in form of a collapsible bag, foil construction or the like) and a surrounding more rigid structure like a casing. Alternatively, the container may comprise a rigid structure or casing and a fluid piston moveable within the casing for forming a variable or collapsible/compressible volume for the liquid.

Preferably, the air pump pressurizes the container and/or liquid in the container only temporarily, in particular only when the nebulizer is cocked or tensioned or loaded (i.e. ready for nebulizing a dose of liquid) and/or when liquid is withdrawn out of the container. Thus, any undesired leakage of liquid from the container can be prevented or at least minimized and/or any (additional) valve between the container and the fluid pump or pressure generator of the nebulizer can be avoided. This allows a simple construction.

Further, the temporary pressurization of the liquid in the container can prevent the formation or growing of any gas bubble within the liquid/container. This supports precise metering and/or allows minimization or reduction of the total volume of liquid initially provided in the container.

Optionally, the air pump is arranged in the nebulizer and driven by the container for pumping air into the container and/or for pressurizing the liquid in the container. This allows a very simple construction and/or use of known containers.

According to an alternative embodiment, the container may form a pump piston of the air pump for pumping air into the container and/or for pressurizing the liquid in the container. This allows a very simple construction.

Preferably, the pump piston cooperates with the housing part of the nebulizer or with a cylinder or insert associated to or held by the housing part. This allows a very simple construction and requires only minor modification of known nebulizers.

Preferably, the air pump is arranged in, fastened to or formed by the housing part of the nebulizer that can be detached or opened for inserting or replacing the container.

Optionally, the container is moveable relative to the air pump during tensioning or cocking or loading the nebulizer or withdrawing a dose of liquid from the container and/or during nebulizing or dispensing a dose of liquid. This relative container movement is preferably used for actuating the air pump and/or for only temporarily pressurizing the liquid in the container and/or only temporarily connecting the air pump to the container (preferably, the air pump is not connected to the container in a non-tensioned or non-loaded state of the nebulizer). This allows a very simple and reliable construction.

Optionally, the air pump is fluidically connectable to a bottom or axial end of the container, preferably opposite to an outlet of the container and/or via a venting hole of the container. This allows a very simple construction or integration in known nebulizers.

According to a further, independent aspect of the present invention, the nebulizer, in particular the air pump, comprises a sealing device acting between the pump piston and the cylinder, wherein the sealing effect of the sealing device depends on the direction of movement of the pump piston relative to the cylinder.

Mostly preferred, the pump piston is only sealed against the cylinder by means of the sealing device or its seal during tensioning/cocking/loading of the nebulizer.

Due to the sealing device, i.e. the variable sealing effect, it is possible to reduce/minimize the impact of the air pump on the dispensing/nebulizing process. In particular, the container can be moved with less frictional resistance during the dispensing/nebulizing process.

BRIEF DESCRIPTION OF THE DRAWING

Further advantages, features, characteristics and aspects of the present invention will become apparent from the claims and the following description of preferred embodiments with reference to the drawings. It shows:

DETAILED DESCRIPTION

Figure 1:
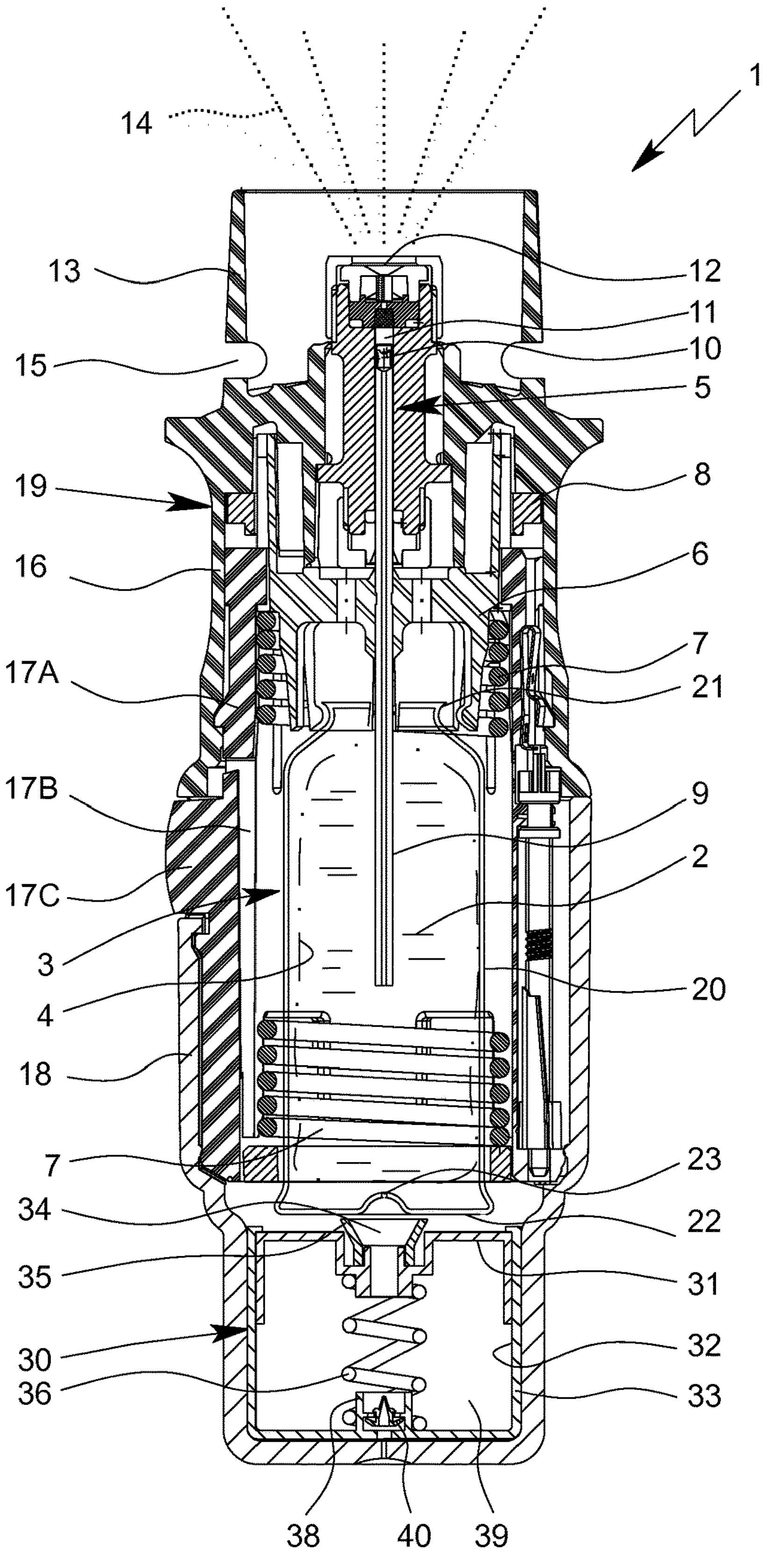
FIG. 1 a schematic section of a nebulizer according to a first embodiment of the present invention in a non-tensioned state.

In the Figures, the same reference numerals are used for identical or similar parts, resulting preferably in corresponding or comparable properties and advantages, even if the associated description is not repeated.

Figure 2:
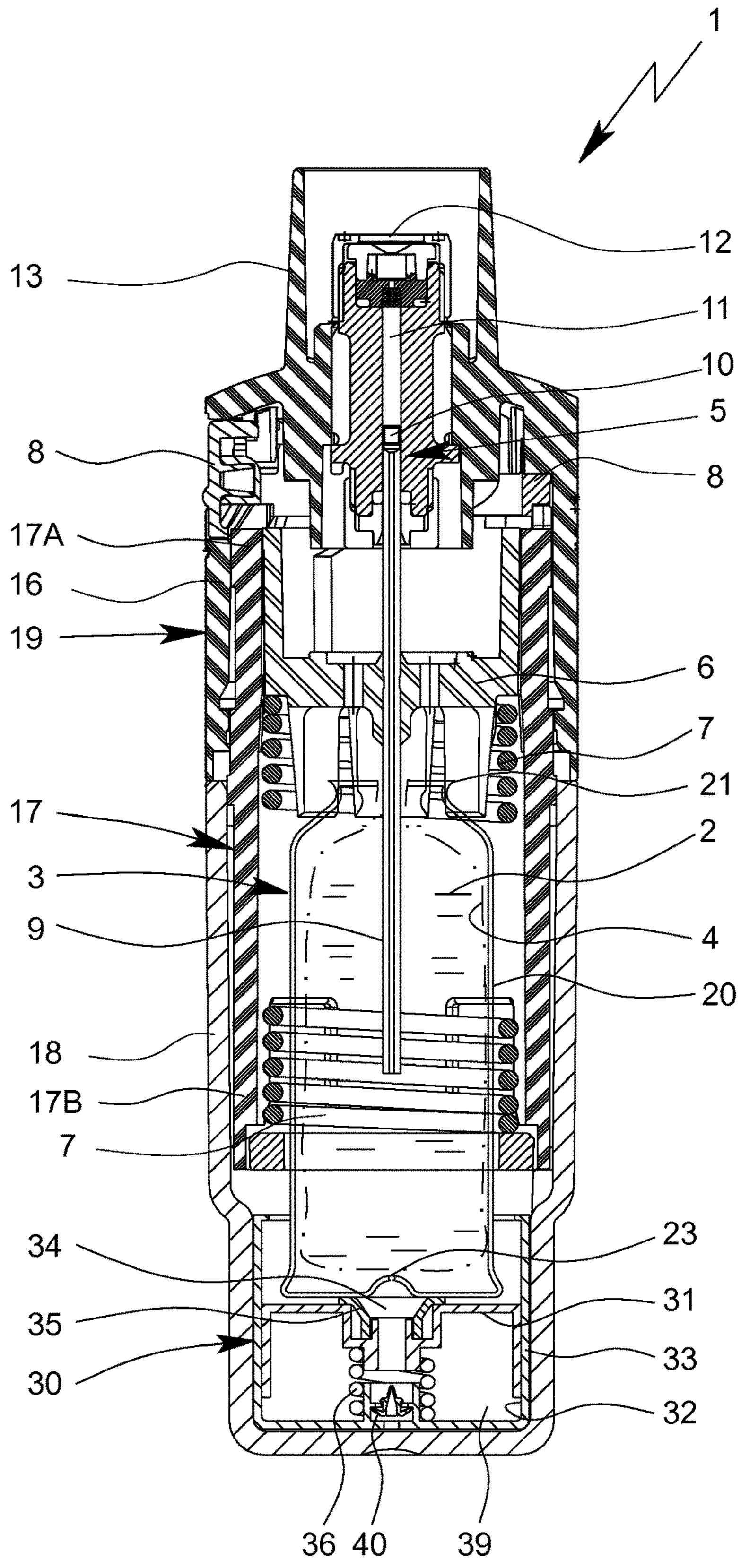
FIG. 2 a schematic section, rotated 90° compared with FIG. 1, of the nebulizer in a tensioned state.

FIGS. 1 and 2 show a nebulizer 1 according to the present invention for atomizing a liquid 2, particularly a highly effective pharmaceutical composition, medicament or the like, diagrammatically shown in a non-tensioned state (FIG. 1) and in a cocked or tensioned state (FIG. 2). The nebulizer 1 is constructed in particular as a portable inhaler and preferably operates only mechanical and/or propellant-free.

When the liquid 2, preferably a pharmaceutical composition, is nebulized, an aerosol 14 (FIG. 1) is formed or dispensed, which can be breathed in or inhaled by a user. Usually the inhaling is done at least once a day, more particularly several times a day, preferably at set intervals, depending on the complaint or illness from which a patient is suffering.

The nebulizer 1 is provided with or comprises or is adapted to receive an insertable or replaceable container 3 containing the liquid 2. The container 3 thus forms a reservoir for the liquid 2, which is to be nebulized.

Figure 3:
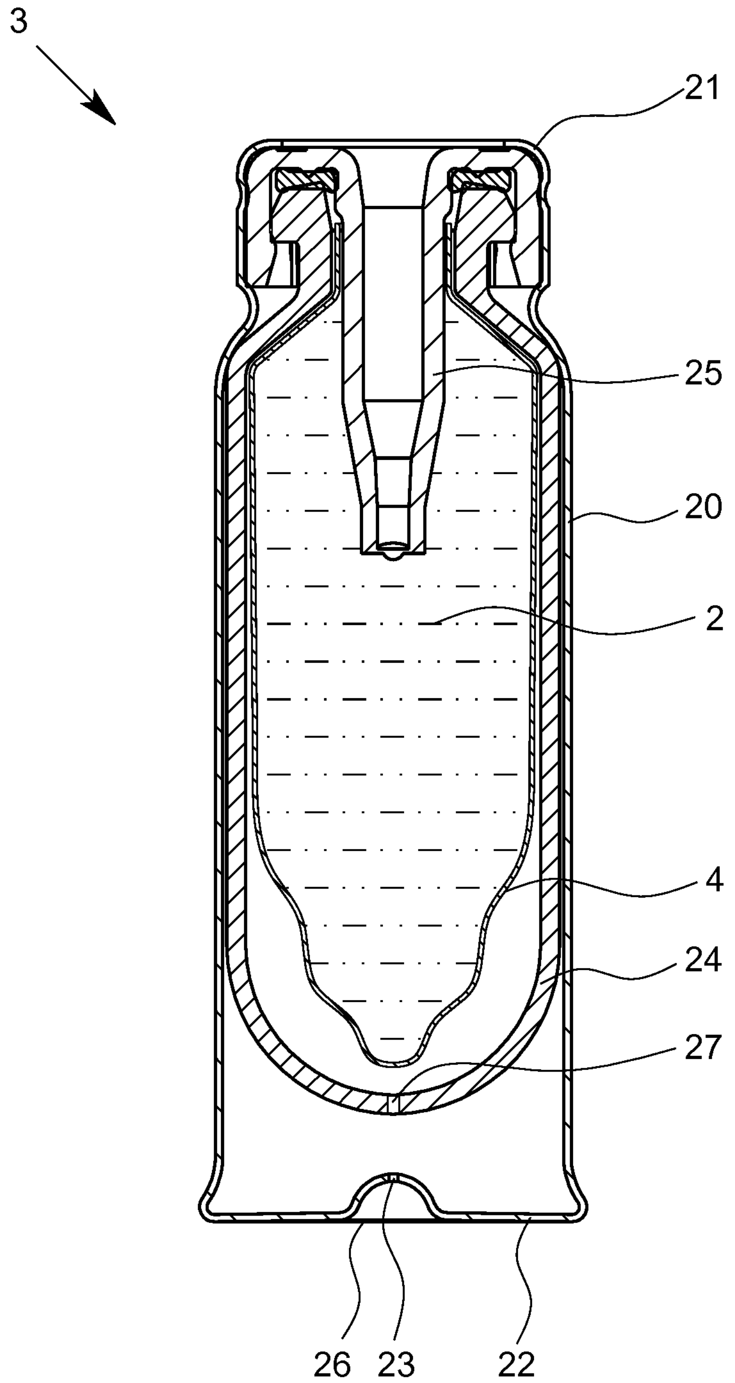
FIG. 3 a schematic section of a first embodiment of a container for the nebulizer.

The container 3 is shown in FIGS. 1 and 2 only schematically and in the section of FIG. 3 in more detail.

Preferably, the container 3 contains multiple doses of liquid 2 or active substance in particular sufficient to provide at least 100 or 150 and/or up to 200 or more dosage units or doses, for example, i.e. to allow at least 100 and/or up to 200 sprays or applications. The container 3 holds preferably a volume of about 0.5 to 20 ml.

Further, the number of doses contained in the container 3 and/or the total volume of the liquid 2 contained in the container 3 can vary depending on the liquid 2 or respective medicament and/or depending on the container 3 and/or depending on the necessary medication or the like.

Preferably, the nebulizer 1 is adapted to nebulize a dose of 1 to 80 microliters of liquid 2, even more preferably a dose of more than 5, 10 or 20 microliters or of about 50 microliters, within one actuation/use of the nebulizer 1/within one spray/aerosol delivery/dispension.

Preferably, the container 3 can be replaced or exchanged, wherein the total number of uses of the nebulizer 1 and thus the number of containers 3, which can be used with the same nebulizer 1, is preferably restricted, e.g. to a total number of four, five or six containers 3. WO 2012/162305 A1 discloses additionally such a restriction to the total numbers of containers 3 which can be used with the same nebulizer 1.

The container 3 is preferably substantially cylindrical or cartridge-shaped and once the nebulizer 1 has been opened the container 3 can be inserted therein preferably from below and changed if desired.

The container 3 is preferably of rigid construction, the liquid 2 in particular being held in a variable or collapsible/compressible volume 4, such as a (flexible) inner container of variable volume, preferably a collapsible bag, in the container 3.

The nebulizer 1 comprises a delivery mechanism, preferably a pressure generator or fluid pump 5, for conveying and nebulizing the liquid 2, particularly in a preset and optionally in an adjustable dosage amount. In particular, the pressure generator or fluid pump 5 withdraws or sucks liquid 2, namely a dose of the liquid 2, from the container 3 or its bag/volume 4, preferably when cocking or tensioning or loading the nebulizer 1. Then, the withdrawn liquid 2 or dose of liquid 2 is dispensed, in particular pressurized and/or nebulized, preferably in a second step after the tensioning or loading process. In particular, the nebulizer 1 comprises an energy store (preferably a drive spring 7) which is loaded (preferably tensioned) during the loading or tensioning process and the energy is released for nebulizing the liquid 2 or dose of liquid 2 which has been drawn into the nebulizer 1 during the tensioning or loading process. Thus, the normal use of the preferred nebulizer 1 encompasses the loading process and the dispensing process.

The nebulizer 1 or pressure generator/fluid pump 5 comprises preferably a holder 6 for holding the container 3, the drive spring 7 associated to the holder 6, only partly shown, and/or a blocking element 8 preferably in form of or with a button for preferably manual actuation or depressing. The blocking element 8 can catch and block the holder 6 and can be manually operated to release the holder 6 allowing drive spring 7 to expand.

The nebulizer 1 or pressure generator/fluid pump 5 comprises preferably a conveying element, such as a conveying tube 9, a non-return valve 10, a pressure chamber 11 and/or a nozzle 12 for nebulizing the liquid 2 into a mouthpiece 13.

The completely inserted container 3 is fixed or held in the nebulizer 1 via the holder 6 such that the conveying element fluidically connects the container 3 or its bag 4 to the nebulizer 1 or pressure generator/fluid pump 5. Preferably, the conveying tube 9 penetrates into the container 3 and/or bag/volume 4, preferably wherein the length of the conveying tube 9 varies depending on the embodiment.

The nebulizer 1 or holder 6 is preferably constructed so that the container 3 can be released or exchanged.

When the drive spring 7 is axially tensioned in the tensioning process or during cocking, the holder 6 with the container 3 and the conveying tube 9 are moved downwards in the drawings and liquid 2 is withdrawn or sucked out of the container 3 into the fluid pump 5 or its pressure chamber 11 through the non-return valve 10. In this state, the holder 6 is caught by the blocking element 8 so that the drive spring 7 is kept compressed. Then, the nebulizer 1 is in the cocked or tensioned state.

During the subsequent relaxation in the dispensing or nebulization process after actuation or pressing of the blocking element 8, the liquid 2 in the pressure chamber 11 is put under pressure (/is pressurized) as the conveying tube 9 with its now closed non-return valve 10 is moved back into the pressure chamber 11, here in the drawings upwards, by the relaxation or force of the drive spring 7 and now acts as a pressing ram or piston. This pressure forces the liquid 2 through the nozzle 12, whereupon it is nebulized into the aerosol 14, as shown in FIG. 1, and, thus, dispensed.

Generally, the nebulizer 1 operates with a spring pressure of 5 to 300 MPa, preferably 10 to 250 MPa, on the liquid 2, for the nebulization of aqueous liquids most preferably 10 to 50 MPa.

Preferably, the energy for the pressure generation is supplied by a drive spring 7 with a mean force ranging from 30 N to 120 N, most preferably with a mean force ranging from 45 N to 90 N, for instance 60 N.

Preferably, a volume of liquid 2 of more than 10, 20 or 30 microliters, preferably about 40 or 50 microliters, is delivered per stroke.

The liquid 2 is converted into or nebulized as aerosol 14, the droplets of which have an aerodynamic diameter of up to 20 micrometers, preferably 3 to 10 micrometers (with a high fraction of particles being smaller than 5 microns in case of the nebulizer 1 being an inhaler). Preferably, the generated jet spray has an angle of 20° to 160°, preferably 80° to 100°. These values also apply to the nebulizer 1 according to the teaching of the present invention as particularly preferred values.

A user or patient (not shown) can inhale the aerosol 14, preferably while air can be sucked into the mouthpiece 13 through at least one optional air supply opening 15.

The nebulizer 1 comprises preferably a housing 19 and/or (upper) housing part 16 and optionally a biasing or inner part 17 preferably which is rotatable relative thereto (FIG. 2) and/or has an upper part 17A and a lower part 17B (FIG. 1).

The nebulizer 1 or housing 19 comprises preferably a (lower) housing part 18. This part 18 is in particular manually operable, and/or releasable fixed, particularly fitted or held onto the inner part 17, preferably by means of a retaining element 17C.

Preferably, the housing parts 16 and 18 and/or other parts form the housing 19 of the nebulizer 1.

In order to insert and/or replace the container 3, preferably the housing 19 can be opened and/or the housing part 18 can be detached from the nebulizer 1, inner part 17 or housing 19.

Generally and preferably, the container 3 can be inserted before the housing 19 is closed and/or before the housing part 18 is connected to the housing 19. The container 3 may be inserted, opened and/or fluidically connected to the delivery mechanism or fluid pump 5 automatically or simultaneously when (completely) connecting the housing part 18 to the housing 19/nebulizer 1 and/or when (completely) closing the housing 19/nebulizer 1. Preferably, the container 3 is open or fluidically connected when tensioning the nebulizer 1 for the first time with the current container 3.

Preferably, the nebulizer 1 or drive spring 7 can be manually activated or tensioned or loaded, in particular by actuation or rotation of an actuation member, here preferably by rotating housing part 18 or any other component.

The actuation member, preferably the housing part 18, can be actuated, here rotated, relative to the upper housing part 16, carrying with it or driving the inner part 17. The inner part 17 acts on a gear or transmission to transform the rotation into an axial movement. As a result the drive spring 7 is tensioned in the axial direction by means of the gear or transmission (not shown) formed between the inner part 17, in particular its upper part 17A, and the holder 6 and acting on the holder 6. During tensioning the container 3 and holder 6 are moved axially downwards until the container 3 assumes an (end) position as shown in FIG. 2. In this activated or tensioned state the drive spring 7 is under tension and can be caught or held by the blocking element 8. During the nebulizing process the container 3 is moved back into its original position (non-tensioned position or state shown in FIG. 1) by (the force of) the drive spring 7. Thus, the container 3 executes a lifting or stroke movement during the tensioning process and during the nebulizing process.

The housing part 18 preferably forms a cap-like lower housing part and/or fits around or over or covers a lower free end portion of the container 3. As the drive spring 7 is tensioned the container 3 moves with its end portion or base 22 (further) into the housing part 18 or towards the end face thereof.

Some container 3, in particular container 3 having a collapsible bag/volume 4 containing the liquid 2, as the one shown in FIG. 3, need an aeration for pressure compensation in order to withdraw the liquid 2 from the container 3.

Preferably, the nebulizer 1 comprises an aeration means for aeration of the container 3 that is preferably sealed in the delivery state.

The optional aeration means, such as a piercing element, arranged in the housing part 18, may come in contact with the base 22 or a venting hole 23 of the container 3 and open or pierce the container 3 or a seal or foil 26 thereon when the container 3 makes contact with it for the first time, to allow air in or aeration.

Figure 5:
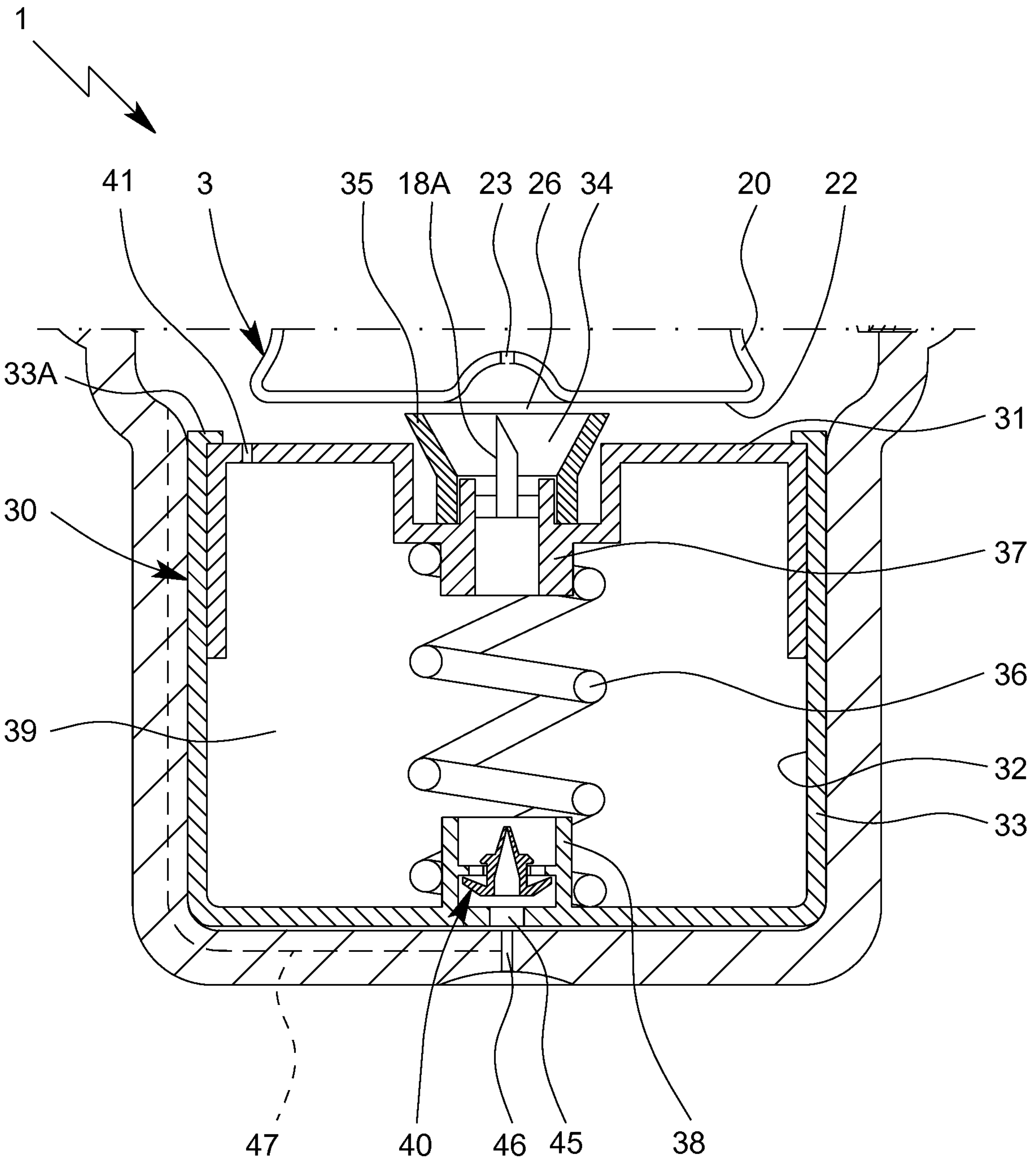
FIG. 5 a schematic section of a lower part of the nebulizer with a piston/cylinder arrangement in the non-tensioned state of FIG. 1.

In particular, FIG. 5 shows in a partial enlargement of FIG. 1 an air pump 30 in the lower part of the nebulizer 1 or housing part 18, wherein an aeration device 18A is schematically indicated. This aeration device 18A comprises or is formed by a piercing element or needle, in particular a hollow needle and/or with a tapered and/or inclined and/or sharp tip or the like, so that the aeration device 18A can easily open or pierce the seal/foil 26 and/or venting hole 23.

The venting hole 23 allows for pressure compensation inside the container 3 when liquid 2 is drawn from the container 3 during the tensioning of the nebulizer 1.

In particular, the container 3 comprises a rigid casing 20, a liquid outlet or head 21 and/or a base 22 opposite the outlet/head 21 as shown in FIG. 3. Preferably, the container 3, casing 20 or base 22 is provided with a venting opening or hole 23 which is opened before or during first use.

Preferably, the container 3 comprises in the first embodiment in addition to the outer, preferably metallic casing 20 an inner, preferably rigid container or shell 24. The shell 24 encompasses or surrounds the bag/variable volume 4.

The shell 24 is preferably made of plastics and/or extends up to the outlet or head 21.

Preferably, the shell 24 is rigidly fastened or received within the casing 20. However, other constructional solutions are possible as well.

The bag/volume 4 is received preferably within the shell 24 such that it can collapse within the shell 24 when liquid 2 is withdrawn. FIG. 3 shows a partially collapsed bag/volume 4 in a very schematic section.

The container 3 or bag/volume 4 is preferably closed by a closure 25 as schematically shown in FIG. 3. It has to be noted that the container 3 or closure 25 is still closed in FIG. 3, in particular the conveying element or tube 9 has not been inserted yet.

Further, FIG. 3 shows the container 3 with still closed venting. In particular, the seal 26, such as a foil or the like, covers or seals the base 22 or venting hole 23 of the container 3 or its casing 20. However, other constructional solutions are possible as well.

When the venting, in particular the seal 26, is open, air or any other gas can flow through the venting hole 23 into casing 20 and through a venting opening 27 into shell 24 so that pressure equalization is possible or achieved. In particular, negative air pressure can be avoided or at least compensated when withdrawing liquid 2 and, thus, collapsing bag/volume 4. However, a throttle effect of the venting hole 23 and venting opening 27 may have different impact on the temporary pressure differences occurring during liquid withdrawal which might result in some variation of the volume of withdrawn doses and/or might even result in the formation or growing of any gas bubble in the liquid 2/bag/volume 4. The present invention can minimize or avoid any such effects due to temporarily pressurizing the liquid 2 and/or temporarily pumping air into the container 3 as described later in detail.

Further, the container 3 could also be constructed as described in WO 2009/115200 A1.

Figure 4:
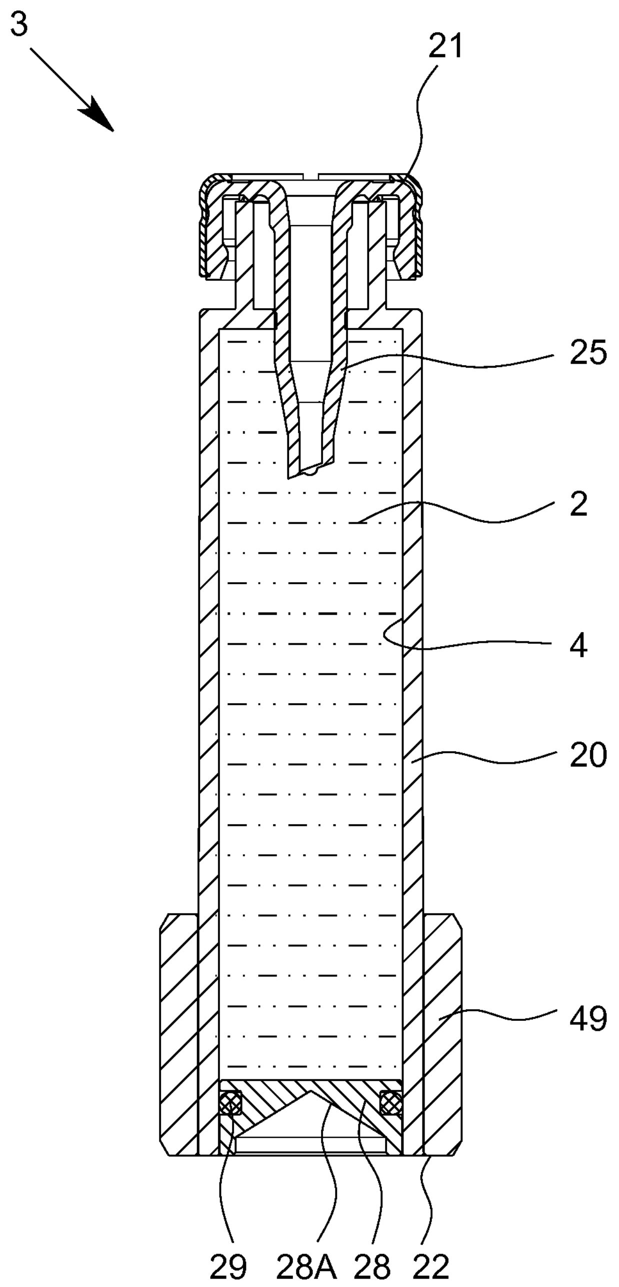
FIG. 4 a schematic section of a second embodiment of the container for the nebulizer.

FIG. 4 shows in a schematic section a second embodiment of the container 3. Here, the variable or collapsible/compressible volume 4 for the liquid 2 is formed or limited preferably by the (outer) casing 20 and a moveable element or piston, hereinafter called fluid piston 28.

Preferably, the fluid piston 28 is moveable axially and/or within the container 3 or casing 20 and/or relative thereto.

Preferably, the container 3 is provided with a seal 29 acting between the fluid piston 28 and the casing 20. In particular, the seal 29 is formed as a ring or lip and/or held by the fluid piston 28. However, other constructional solutions are possible as well.

FIG. 4 shows the container 3 in a delivery state and/or a completely filled state where the fluid piston 28 is in its initial position before withdrawing any liquid 2 from the container 3. In particular, the initial position is adjacent to or at the base 22 or axial end of the container 3 or casing 20 opposite to the outlet or head 21. Thus, a maximum filling volume of the container 3 can be realized.

Here, the piston 28 is preferably accessible from the exterior, in particular such that the venting hole 23 and the venting opening 27 can be omitted. However, other solutions are possible, e.g. wherein the container 3 is axially closed/sealed, in particular such that the container 3 needs an aeration for pressure compensation in order to withdraw the liquid 2 from the container 3. Such an embodiment will be described later, in particular with reference to FIGS. 15 to 24.

When withdrawing liquid 2, the piston 28 moves axially towards the outlet or head 21, here in the representation of FIG. 4 upwards.

The container 3 according to the embodiment shown in FIG. 4 preferably comprises also an at least essentially cylindrical form and/or a similar casing 20, head 21 and/or closure 25 as the container according to the embodiment of FIG. 3.

Preferably, both types or embodiments of containers 3 can be used in the nebulizer 1 shown in FIGS. 1 and 2.

The nebulizer 1 preferably comprises an air pump 30 for—in particular temporarily—pressurizing the liquid 2 in the container 3, in particular the bag/variable volume 4 in the container 3, preferably to help collapsing/compressing the bag/volume 4 and/or to facilitate withdrawal or sucking of liquid 2 from the container 3.

In the first embodiment of the nebulizer 1, the air pump 30 is formed preferably separately from the container 3.

The air pump 30 is preferably connectable—in particular only temporarily—to the container 3 or its casing 20 or base 22 or venting hole 23.

The air pump 30 is preferably arranged opposite to the fluid pump 5 and/or the liquid outlet or head 21 of the container 3.

The air pump 30 is arranged or located preferably at or in the housing part 18 and/or adjacent to the base 22 of the container 3.

Preferably, the air pump 30 comprises a pump piston 31 and a cylinder 32 cooperating with the pump piston 31. Thus, the air pump 30 comprises or forms a piston/cylinder arrangement for pressurizing the liquid 2 in the container 3 and/or for pumping air into the container 3.

Preferably, the pump piston 31 is cup-like.

Optionally, a sealing can be provided between the pump piston 31 and the cylinder 32. For example, a sealing element, such as an O-ring or the like, could be used. Alternatively or additionally, the inner surface of the cylinder 32 and/or the outer surface of the pump piston 31 can be provided with a glide agent, such as silicone, grease or the like, in order to reduce friction and/or for sealing.

The cylinder 32 may be formed by the housing part 18 or an element or insert 33 attached to or arranged in the nebulizer 1, the housing 19 or—most preferably—the housing part 18.

In the shown embodiment, the insert 33 is fixed in the housing part 18 by press-fit or form-fit or by glueing, welding or the like.

The air pump 30 or pump piston 31 preferably comprises a port 34 and/or seal 35 for pneumatically connecting the air pump 30 to the container 3 or its base 22 or venting hole 23.

Preferably, the seal 35 is arranged at or around the port 34 or forms the port 34 and/or is held by the pump piston 31.

Preferably the seal 35 forms an annular lip and/or conical connection portion for sealing against the container base 22 and/or surrounding the venting hole 23 when the container 3 is pneumatically connected to the air pump 30 or vice versa. In this state, the port 34 or seal 35 abuts preferably against the container base 22.

Preferably, the air pump 30, pump piston 31, port 34 and/or seal 35 is arranged centrally and/or below the container 3, base 22 or venting hole 23 and/or in axial alignment with the container 3 or its stroke movement.

The air pump 30 preferably comprises a return spring 36 for returning or biasing the pump piston 31 into its initial position shown in FIG. 1. The pump piston 31 is in this initial or upper position in particular when the nebulizer 1 is not in use or is not tensioned.

Preferably, the air pump 30 or insert 33 comprises a stop 33A as indicated in FIG. 5 for restricting the return travel of the pump piston 31 and/or defining the initial or upper position of the pump piston 31.

In the shown embodiment, the return spring 36 acts between the pump piston 31 and the housing part 18 or insert 33.

Preferably, the return spring 36 is formed by a helical spring and/or extends in axial direction or in the direction of stroke movement of the container 3 and/or is arranged centrally in the nebulizer 1, below the container 3 and/or in the air pump 30.

Preferably, the pump piston 31 comprises a bearing part 37, such as a recess or protrusion, for holding an associated end of the return spring 36.

Preferably, the insert 33 or housing part 18 comprises a bearing part 38, such as a recess or protrusion, for holding the associated end of the return spring 36.

The air pump 30 preferably comprises a pump chamber 39 formed between the pump piston 31 and the cylinder 32/insert 33. In particular, the volume of the pump chamber 39 is defined or varied by the position or movement of the pump piston 31.

FIG. 2 shows the nebulizer 1 in the tensioned state with the pump piston 31 in the actuated or depressed position. In this position, the pump piston has been moved (further) into the cylinder 32 or insert 33 or housing part 18 and air contained in the pump chamber 39 has been compressed and/or delivered into the container 3.

The air pump 30 works preferably (only) mechanically.

Preferably, the air pump 30 is arranged in the center of the nebulizer 1 and/or below the container 3 and/or axially aligned with the nebulizer 1 and/or container 3.

The air pump 30 or pump piston 31 is preferably actuated by the movement of the container 3 within the nebulizer 1 and/or the stroke-like movement or tensioning movement of the container 3.

In particular, the container 3 or its base 22 is spaced from the air pump 30, pump piston 31, port 34 or seal 35 when the nebulizer 1 or container 3 is in the non-tensioned state or after nebulizing a dose.

Thus, the air pump 30 is temporarily open and/or (pneumatically) disconnected from the container 3 or vice versa. In particular, the aeration or venting hole 23 is open or uncovered in the non-tensioned state so that free compensation is possible between the pressure within the container casing 20 and the outer atmosphere.

Preferably, the stroke-like movement or tensioning movement of the container 3 controls opening or filling of the air pump 30.

When tensioning the nebulizer 1, the container 3 is moving towards and/or relative to the air pump 30 or its pump piston 31. After a first (shorter) part of the tensioning movement, the container 3 or its base 22 (pneumatically) connects with the air pump 30 or its pump piston 31 or port 34/seal 35. During the further or second (larger) part of the tensioning movement, the air pump 30 or pump piston 31 is actuated or depressed so that an air pressure is generated which can directly act—here preferably via the port 34/seal 35 and the venting hole 23—on the liquid 2 in the container 3 or, more precisely, on the bag 4 (i.e. the variable volume) within the container 3. In other words, the air pump 30 pumps air into the space between the bag 4 and the casing 20/shell 24.

Preferably, the air pump 30 comprises a total volume and/or a pump volume of more than 0.1 $cm^3$, in particular of more than 0.5 $cm^3$, and more preferably of more than 1.0 $cm^3$. In particular, the pump volume is between 1 and 4 $cm^3$.

Preferably, the pump volume of the air pump 30, i.e. here the volume difference between the uncompressed state and the compressed state of the air pump 30 and/or the minimum volume of air pumped into the container 3 by the air pump 30 during each actuation, is more than 3%, in particular more than 5%, most preferably more than 8%, and/or less than 50%, preferably less than 40%, most preferably less than 30%, of the air volume of the container 3 after withdrawing the maximum number of doses of liquid 2 or all liquid 2.

Preferably, the air pump 30 provides a defined or limited pressure increase (depending on the maximum air pressure provided by the air pump 30) in the container 3 (in particular in the space between the inner container and the casing 20 and/or shell 24) or acting on the liquid 2/bag/volume 4 of more than 25 hPa, preferably more than 40 hPa, and most preferably of more than 50 hPa or 100 hPa, in particular just after tensioning the nebulizer 1.

The pressure increase mentioned above might depend on the state of collapsing/compressing of the bag/volume 4. The above values apply in particular when the bag/volume 4 is completely collapsed/compressed and/or when the maximum number of withdrawn doses of liquid 2 is reached.

The pressure acting on the bag/volume 4 in the container 3 increases during the second part of the tensioning movement of the container 3, i.e. during the actuation of the air pump 30, until the tensioned state or (end) position and the maximum air pressure are reached. This pressure increase helps of facilitates withdrawal or sucking of liquid 2 from the container 3 or its bag/volume 4.

Preferably, the nebulizer 1 or air pump 30 comprises at least one air leakage or valve 40 for controlling or limiting the (maximum) air pressure and/or for aerating the air pump 30 or its pump chamber 39 and/or for preventing any underpressure (negative pressure with respect to the ambient pressure) in the air pump 30 or pump chamber 39. However, the valve 40 is only optional and can be omitted.

Preferably, the pressure decreases again, in particular automatically, during the nebulization process (preferably due to movement of the pump piston 31 from its actuated position into the initial position or due expansion of the pump chamber 39 caused by the return spring 36 or due to disconnection of the air pump 30 or port 34 from the container 3 during the nebulization movement of the container 3) and/or preferably even already in the tensioned state (preferably due to the air leakage and/or valve 40).

Therefore, the bag 4 or liquid 2 is pressurized only temporarily in the container 3, preferably mainly only during the tensioning movement and/or preferably primarily only during withdrawal of a dose of liquid 2 from the container 3 or its bag/volume 4.

After withdrawing or sucking liquid 2 from the container 3 or its bag/volume 4, the nebulizer 1 is in the tensioned or cocked state and/or is ready for dispensing/nebulization.

In the tensioned or cocked state, the air pressure and, thus, the pressurization of liquid 2 decreases and, preferably, is terminated, in particular automatically, due to the air leakage, e.g. between the pump piston 31 and the cylinder 32 and/or between port 34/seal 35 and container base 22. To achieve a desired leakage, there can be provided radial play between the pump piston 31 and the cylinder 32 and/or a respective leakage channel or passage 41, e.g. in the seal 35 or valve 40 or pump piston 31.

The air pump 30 and the fluid pump 5 work/pressurize preferably alternately and/or act preferably on different parts of the nebulizer 1. In particular, the air pump 30 is adapted to pressurize the liquid 2 contained in the container 3 and the fluid pump 5 is adapted to pressurize the liquid 2 contained in the pressure chamber 11.

Mostly preferred, the air pump 30 pressurizes air and, thus, the liquid 2 in the container 3, when/during tensioning or loading the nebulizer 1 and/or during/for withdrawal of a dose of the liquid 2 from the container 3, and the fluid pump 5 pressurizes the dose of liquid 2 that has been withdrawn from the container 3 and/or is located in the pressure chamber 11 when/during/for dispensing or nebulizing the dose of liquid 2.

Figure 6:
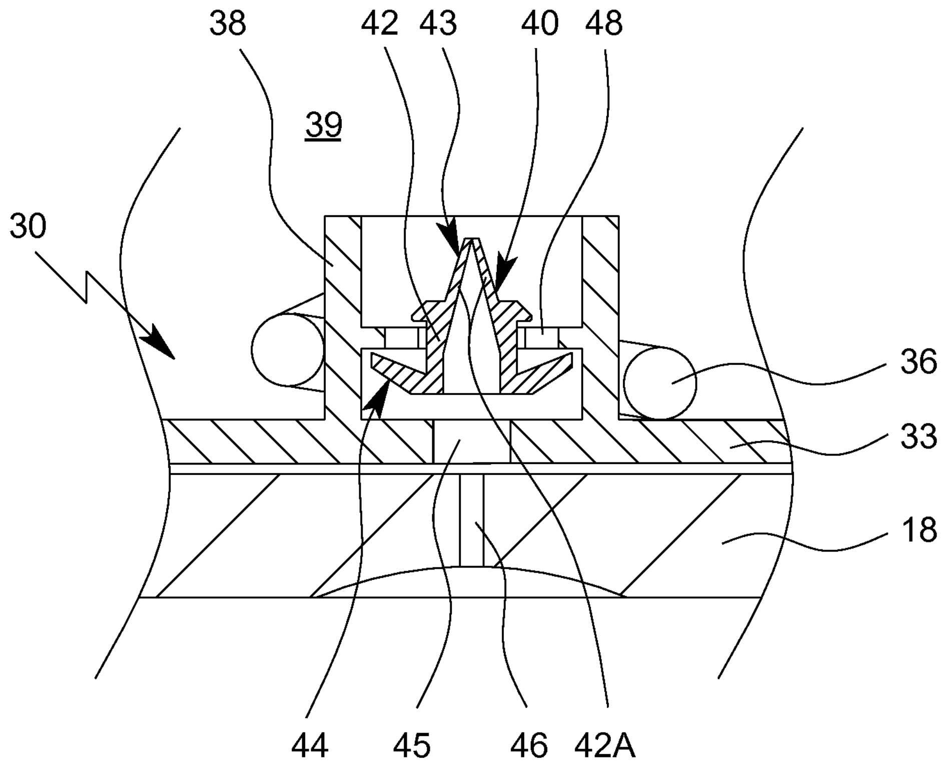
FIG. 6 a partial enlargement of FIG. 5 illustrating a preferred construction of a valve.

FIG. 5 shows in a partial enlargement of FIG. 1 the air pump 30 in the lower part of the nebulizer 1/housing part 18. FIG. 6 shows an enlargement of FIG. 5 in the area of the valve 40.

In the shown embodiment, the air pump 30 or pump piston 31 is preferably provided with the leakage passage 41 as schematically shown in FIG. 5. However, this leakage passage 41 is optional.

Preferably, the leakage passage 41 or any other air leakage, such as the optional/preferred radial play between the pump piston 31 and the cylinder 32, forms a throttle which is dimensioned such that the flow resistance is sufficiently high to create a sufficiently high air pressure during the tensioning stroke and is sufficiently low so that pressurized air can escape relatively quickly in the tensioned state from the pump chamber 39 into the housing 19 and/or environment so that the air pressure is quickly decreased in the tensioned state to avoid any undesired liquid flow in the tensioned state of the nebulizer 1 before firing (actuating blocking element 8 to initiate nebulization).

According to another embodiment, that will be described later with reference to FIGS. 15 to 20, a seal 54 or sealing device 57 acting between the pump piston 31 and the cylinder 32 might (temporarily) provide or open the leakage passage 41 between the pump piston 31 and the cylinder 32.

After actuating or firing the nebulizer 1, preferably by actuating or pressing element 8, the pressure generator or fluid pump 5 pressurizes and dispenses the previously withdrawn dose of the liquid 2 while the container 3 is moving in opposite direction and finally retracting from the air pump 30 and/or pump piston 31/port 34/seal 35.

The return spring 36 and/or any other return means biases or moves the pump piston 31 preferably back into its initial position. This ensures a defined operation of the air pump 30 and/or supports the dispensing stroke and/or prevents or reduces the occurrence of any negative force or holding effect acting on the container 3 during the dispensing stroke, i.e. during an upward movement in FIG. 2.

The air pump 30 may be provided or connected with the valve 40 allowing prompt and/or easy re-filling of the air pump 30 and/or preventing any underpressure in the air pump 30, e.g. during the dispensing or actuation stroke of the nebulizer 1, so that any negative influence of the air pump 30, such as a holding force acting opposite to the dispensing movement of the container 3, is securely prevented.

In FIGS. 5 and 6, the valve 40 is shown, but it is only optional, i.e. the valve 40 could be omitted.

In the preferred embodiment, the valve 40 in particular comprises a valve element 42 which is preferably formed as a unitary plastic part.

The valve 40 or valve element 42 preferably forms or comprises an inlet, duckbill or one-way/check valve 43 which opens to avoid or at least minimize any underpressure in the air pump 30 or pump chamber 39 during the dispensing stroke, i.e. when the pump piston 31 moves back from its actuated position shown in FIG. 2 to its initial position shown in FIGS. 1 and 5.

Preferably, the valve 40 or valve element 42 or inlet valve 43 comprises—in particular two—flexible portions 42A as schematically indicated in FIG. 6.

Preferably, the portions 42 have two flat areas that can assume a duckbill form in the closed position shown in FIG. 6 wherein the free ends of the portions 42A contact each other to close valve 43.

However, other constructional solutions are possible as well, in particular wherein the valve 40, valve element 42 and/or inlet valve 43 is dome-like shaped and/or curved and/or at least essentially hemispherical, as will be described with reference to FIG. 9.

The valve 40/43 and, in particular, the portions 42A open preferably very easily (i.e. at very low pressure difference between the ambient pressure and the pressure in the pump chamber 39) by flexing apart from each other in order to allow ambient air to flow into the pump chamber 39 in order to prevent any underpressure in the pump chamber 39. With other words, the valve 40 and, in particular, the portions 42A form preferably the inlet valve or check valve 43 in the present embodiment.

Preferably, the valve 40/43 and, in particular, the portions 42A can return to its closed position automatically, preferably due to a restoring force, and/or already due to a low pressure difference with higher pressure in the pump chamber 39 than in the environment.

During the nebulizing stroke, the return spring 36 moves the pump piston 31 starting from the actuated position back into its initial position. During this return travel, the air pump 30 or pump piston 31 keeps the seal 35 in contact with the container base 22 until the initial position and/or stop 33A is reached. During this return movement, the pump chamber 39 expands and would generate a significant underpressure so that aeration is advantageous. In particular, the aeration or inlet valve 43 prevents the occurrence of any (relevant) underpressure during this return travel or movement.

The valve 40 or inlet/check valve 43 is connected to the atmosphere preferably via an opening 45, here formed in the optional insert 33, and/or via a channel 46 which is preferably formed in the housing part 18 and may open to the bottom or environment.

Alternatively or additionally, a channel 47 may be formed in the housing part 18 as schematically shown by a dashed line in FIG. 5, and/or in the insert 33 for fluidically connecting the inside of the nebulizer 1 or its housing 19 with the valve 40 or inlet/check valve 43 to allow ventilation or aeration of the air pump 30 or its pump chamber 39, namely to allow (only) air flow into the pump chamber 39.

The valve 40 or valve element 42 or another valve of the nebulizer 1 or air pump 30 preferably comprises or forms a control valve 44 for controlling or limiting the air pressure acting on the liquid in the container 3 and/or provided or reached by the air pump 30.

In the shown embodiment, the control valve 44 is preferably formed like an umbrella and/or covers one or more outlet openings 48 as schematically shown in FIG. 6.

The control valve 44 opens preferably when a predetermined or desired air pressure is reached in the air pump 30 or pump chamber 39. Thus, a defined or maximum air pressure is provided for pressurizing the liquid 2 in the container 3.

The control valve 44 opens and closes preferably automatically, in particular in response to a pressure difference between the environment and the pump chamber 39 so that ambient air (or air from the inside of the nebulizer 1 with ambient pressure) can flow into the pump chamber 39, preferably with a very low or non-relevant flow resistance. In the opposite flow direction, the control valve 44 preferably closes and/or prevents any flow. However, the control valve 44 could also allow a defined leakage flow in this opposite direction to form the air leakage and/or so that e.g. the leakage passage 41 can be omitted.

The preferred controlling or limiting of the air pressure provided by the air pump 30 to a maximum air pressure (i.e. to a maximum value above the ambient air pressure) results in the advantage that the liquid 2 in the container 3 is pressurized with a desired and/or predetermined pressure independent from the filling level of the container 3, i.e. independent from the air volume of the container 3.

In the shown embodiment, the valve 40, the inlet/check valve 43 and/or control valve 44 are preferably located in or at the pump chamber 39 or bearing part 38. However, other constructional solutions are possible as well.

Preferably, the valve 40 or its valve element 42 forms both, the inlet/check valve 43 and the control valve 44, to simplify the construction.

Mostly preferred, the valve 40, the inlet/check valve 43 and the control valve 44 are formed integrally and/or in one piece.

It is also possible that the seal 35 forms the valve 40, inlet/check valve 43 and/or control valve 44 or vice versa.

In the embodiment shown in FIG. 5, the optional aeration device 18A is preferably arranged within or adjacent to the port 34 and/or seal 35 and/or at or adjacent to the pump piston 31 and/or bearing part 37. In particular, the aeration device 18A or its needle is held by radial ribs, an insert or the like cooperating or connected with the pump piston 31, bearing part 37 or the like.

In the shown embodiment, the aeration device 18A is arranged preferably at or within the port 34, seal 35 and/or bearing part 37, but allows a sufficient or unrestricted air flow therethrough. For this purpose, only few radial ribs might be provided and/or the aeration device 18A or its needle can be hollow.

As already mentioned, either the container 3 as shown in FIG. 3 or the container 3 as shown in FIG. 4 can be used with the nebulizer 1 shown in FIGS. 1 and 2. If the container 3 according to the second embodiment shown in FIG. 4 is used, the seal 35 of the air pump 30 should be adapted so that it abuts against the end or base 22 of the container 3, and not within the opening for the fluid piston 28.

In particular, the container 3 may comprise a modified end 49, here shown in FIG. 4 as an additional part, ring, sleeve or the like attached to the casing 20. This modified end 49 may form an annular end face or base 22 of the container 3 with which the seal 35 may cooperate.

However, other constructional solutions are possible. For example, the container 3 might be provided with the seal 35 instead of air pump 30 or pump piston 31.

Alternatively, the pump piston 31 can be directly connected or connectable with the container 3 or its base 22. In this case, the return spring 36 can be omitted similar to the second embodiment described below.

In the following, a second embodiment of the nebulizer 1 will be described with reference to the further drawings, wherein the description will focus on differences and new aspects and features so that the previous description shall apply in addition or in a similar manner even if not repeated.

Figure 7:
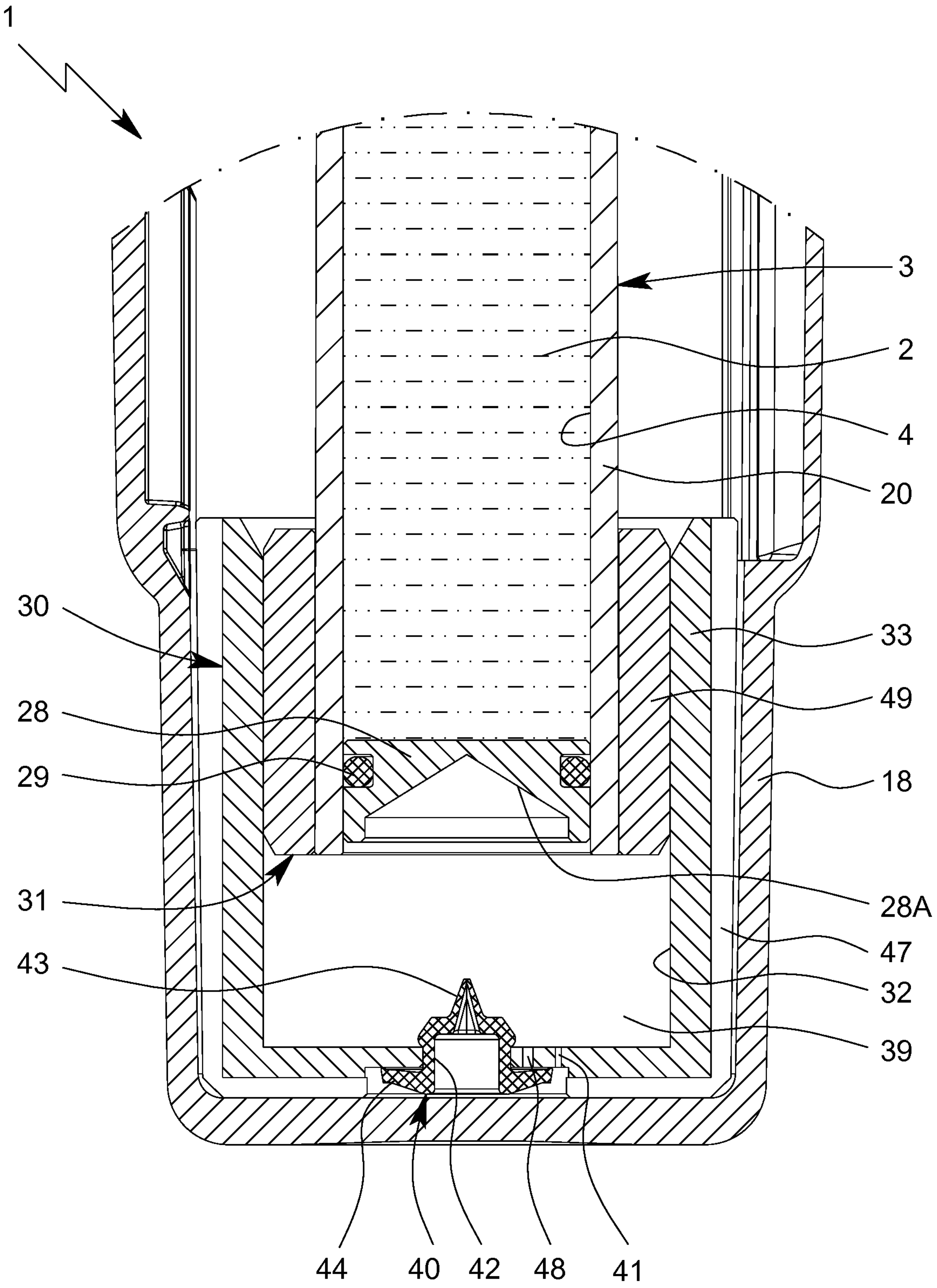
FIG. 7 a schematic section of a lower part of the nebulizer according to a second embodiment of the present invention in a non-tensioned state.
Figure 8:
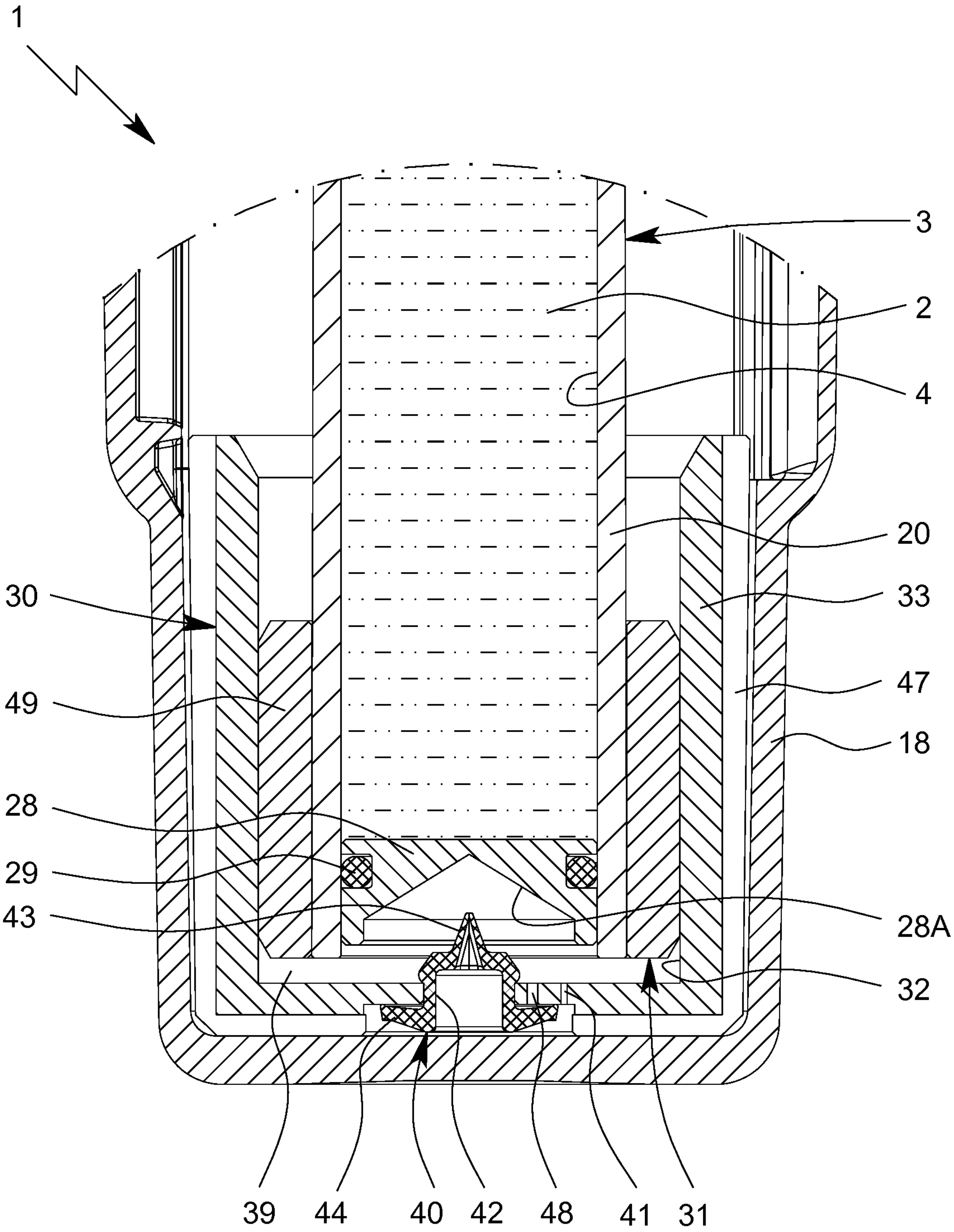
FIG. 8 a schematic section of the lower part of the nebulizer similar to FIG. 7, but in a tensioned state.

FIG. 7 shows a lower portion of the second embodiment of the nebulizer 1 with the container 3 according to the second embodiment in the non-tensioned state, i.e. an enlargement similar to FIG. 5, but with a modified air pump 30. FIG. 8 shows the nebulizer 1 and container 3 according to the second embodiment in a similar section, but in the tensioned state.

The nebulizer 1 according to the second embodiment uses the container 3 according to the second embodiment shown in FIG. 4.

In the second embodiment, the container 3, in particular its modified end 49, forms or is used as the pump piston 31. The container 3 cooperates with the cylinder 32 preferably formed by the housing part 18 or insert 33 so that a piston/cylinder arrangement for pressurizing the liquid 2 in the container 3 and/or for pumping air into the container 3 to help withdrawing the liquid 2 in doses from the container 3 is formed.

Here, the pump chamber 39 is formed between the container 3 or its base 22 and the cylinder 32/insert 33.

The container 3 or its modified end 49 is moveable or guided within the cylinder 32, preferably with very low friction and/or a (little) radial play forming a desired air leakage and making it possible to avoid the optional defined leakage passage 41.

In the second embodiment, the air pump 30 acts directly on the fluid piston 28 in order to pressurize the liquid 2 in the variable volume 4 of the container 3.

In the second embodiment, the valve 40 is preferably constructed similar as in the first embodiment and/or provides the same functionality.

In the second embodiment, the aeration channel 47 is formed preferably in the insert 33.

The container 3 or fluid piston 28 preferably comprises a recess 28A so that the valve 40 arranged on the bottom or base of the pump chamber 39 can protrude into the recess 28A in the tensioned state when the container 3 is completely filled, i.e. when the fluid piston 28 is in its first/lower axial (end) position at or adjacent to the container base 22.

Generally, the diameter of the pump chamber 39 or cylinder 32/pump piston 31 is preferably larger than the diameter of the bag/volume 4 in the container 3 to ensure a great pressure increase/amplification and/or high pump volume.

The present invention or air pump 30 prevents that any or at least any relevant underpressure can occur in the liquid 2 in the container 3 when a dose of the liquid 2 is withdrawn or sucked from the container 3. Thus, it can be ensured that always the same volume is withdrawn from the container 3.

In particular, the shown or proposed containers 3 allow an adaptation of the variable or collapsible/compressible volume 4 for the liquid 2 (here by collapsing the bag or movement of the fluid piston 28) in response to any pressure difference, in particular in response to any underpressure acting on the liquid 2 in the container 3 or volume 4. For the adaptation of the volume 4, in particular for collapsing the bag or moving the fluid piston 28, a certain pressure difference must be applied in order to overcome any inertia and/or friction or adhesion. The preferably temporary or only short-term pressurization of the variable volume 4, preferably by means of the air pressure or air pump 30, helps or supports to achieve the desired/required pressure difference to decrease the volume 4. Thus, any underpressure can be avoided in the volume 4 during the withdrawal of a dose of the liquid 2 from the container 3.

Preferably, a pressure pulse—in particular provided by the nebulizer 1 or air pump 30—acts on the variable volume 4 or the liquid 2 in the container 3 at the beginning and/or during the tensioning of the nebulizer 1 and/or withdrawal of liquid 2 from the container 3. This helps withdrawing the liquid 2 in doses from the container without forming or growing of any gas bubble within the liquid 2/container 3.

Figure 9:
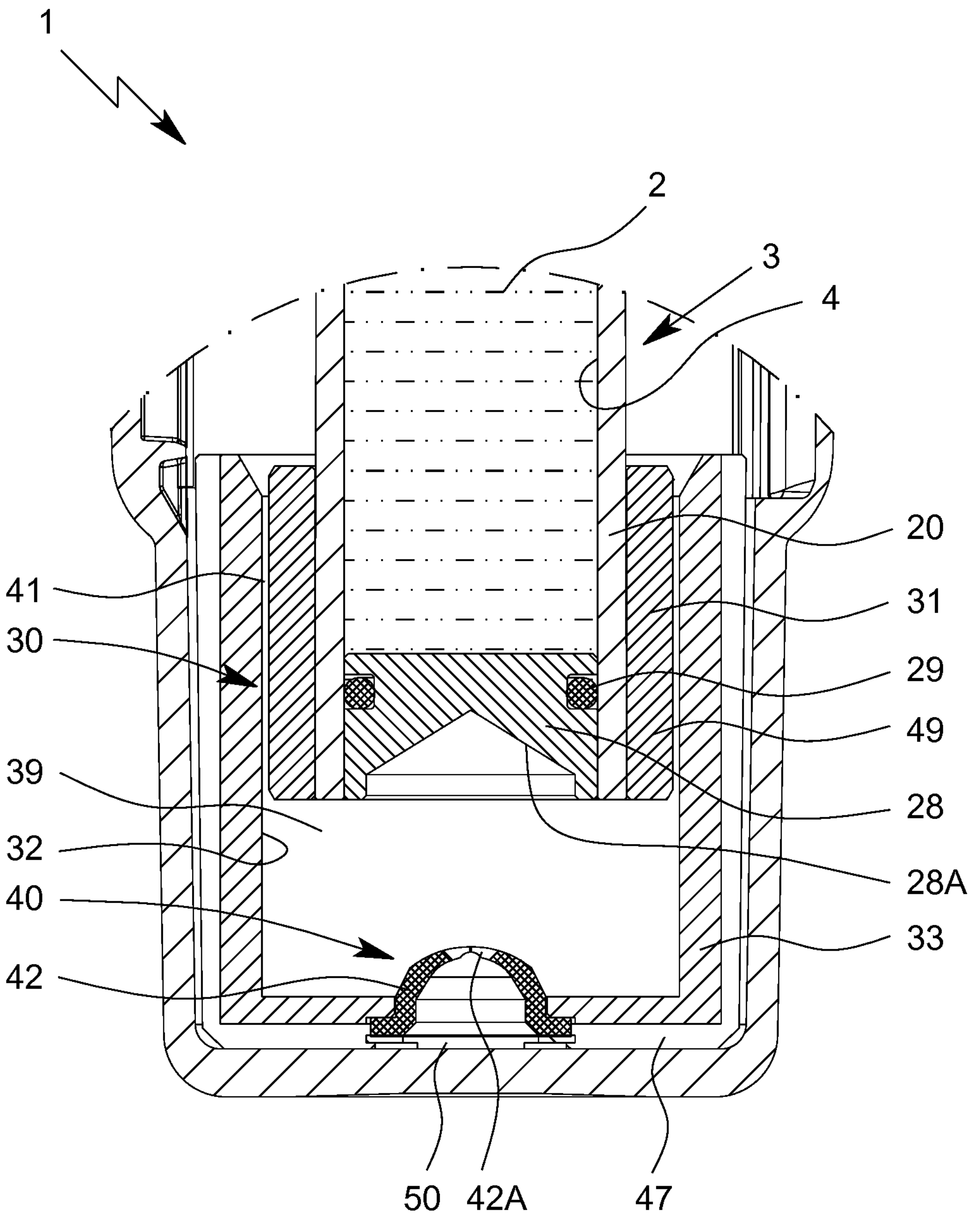
FIG. 9 a schematic section of a lower part of the nebulizer in the non-tensioned state similar to FIG. 7, but with a modified valve.

FIG. 9 shows in a partial section similar to FIG. 7 the nebulizer 1 according to the second embodiment with inserted container 3 according to the second embodiment in the non-tensioned state with a modified valve 40. In this modified version, the valve 40 is preferably dome-like shaped, curved and/or at least essentially hemispherical.

The modified valve 40 provides preferably the same functionality as the previously described versions and/or controls or limits the (maximum) air pressure in the pump chamber 39 and/or allows ambient air to flow into the pump chamber 39 in order to prevent any underpressure in the pump chamber 39.

Preferably, the valve element 42 of the modified valve 40 comprises slits and/or flexible portions 42A (preferably the portions 42A form sectors of a disk/circle in top view of the valve element 42).

As already mentioned, the valve 40 preferably comprises or forms both, the inlet valve 43 and the control valve 44. In particular due to the dome-like shape of the valve 40, the valve 43 and the control valve 44 preferably comprise a common air passageway and/or a common valve element 42, in particular common flexible portions 42A.

The valve 40 and, in particular, the portions 42A open preferably very easily (i.e. at a very low pressure difference between the ambient pressure and the pressure in the pump chamber 39) towards the interior of the air pump 30 or pump chamber 39 in order to allow ambient air to flow into the pump chamber 39 in order to prevent any underpressure in the pump chamber 39. With other words, the valve 40 and, in particular, the portions 42A preferably form the inlet valve or check valve 43 described above.

Preferably, the valve 40 and, in particular, the portions 42A can flex or open to the outside, i.e. away from the interior of the air pump 30, and allow air to escape from the pump chamber 39 only if the pressure inside the pump chamber 39 is significantly higher than the ambient air pressure, i.e. only if the pressure difference reaches or exceeds a maximum value corresponding to a maximum air pressure. With other words, the valve 40 and, in particular, the portions 42A preferably form the control valve 44 as described above.

As already mentioned, the nebulizer 1 preferably comprises the control valve 44 which is preferably adapted to open automatically when the pressure in the air pump 30, in particular its pump chamber 39, exceeds a (first) maximum value above the ambient pressure and/or which is preferably adapted to close automatically when the air pressure in the air pump 30, in particular its pump chamber 39, corresponds to a (second) maximum value above the ambient pressure.

Further, the nebulizer 1 preferably comprises the inlet valve 43 which is preferably adapted to open automatically when the air pressure in the air pump 30, in particular pump chamber 39, is below the ambient pressure and/or which is preferably adapted to close automatically when the air pressure in the air pump 30, in particular the pump chamber 39, corresponds to the ambient pressure.

Preferably, the valve 40, in particular the portions 42A, form(s) both, the control valve 44 and the inlet/check valve 43.

Preferably, the valve 40 and, in particular, the portions 42A is/are adapted to flex/open towards the interior of the air pump 30, in particular the pump chamber 39, more easily, i.e. by exerting a lower force, than towards the outside, i.e. away from the interior of the air pump 30 or pump chamber 39.

Preferably, the valve 40 and, in particular, the portions 42A is/are adapted to flex/open towards the interior of the air pump 30 or pump chamber 39 due to a pressure difference between the air pump 30 or pump chamber 39 and the atmosphere/environment that is lower than the pressure difference needed to flex/open the valve 40 and, in particular, the portions 42A towards the outside and/or away from the interior of the air pump 30 or pump chamber 39.

Mostly preferred, the valve 40 and, in particular, the portions 42A is/are adapted to open and close within two different operating/pressure ranges, namely a first operating/pressure range and a second operating/pressure range, preferably wherein the second operating/pressure range is below the first operating/pressure range.

Preferably, the first operating range is above the ambient pressure and the second operating range is below the ambient pressure.

In the first operating/pressure range the valve 40, in particular the portions 42A, flex(es)/open(s) preferably towards the outside of and/or away from the interior of the air pump 30 or pump chamber 39, in particular in order to reduce the air pressure in the air pump 30 or pump chamber 39.

In the second operating/pressure range the valve 40, in particular the portions 42A, flex(es)/open(s) preferably towards the inside of air pump 30 or pump chamber 39, in order to increase the air pressure in the air pump 30 or pump chamber 39.

Preferably, the force/pressure difference (across the valve 40) needed to open the valve 40 and, in particular, the portions 42A, depends on the opening direction of the valve 40.

The directional properties of the valve 40 and, in particular, the portions 42A are preferably achieved by the dome-like shape of the valve 40.

Preferably, due to the additional force needed to push the tips of the portions 42A past each, a higher force, i.e. pressure difference, is needed to open the valve 40 to the outside of and/or away from the interior of the air pump 30 or pump chamber 39 than into the other direction. However, the directional properties can also be achieved otherwise, e.g. by using anisotropy, enforcements and/or notches, grooves or the like within the portions 42A.

In particular due to the valve 40 or inlet valve 43 and/or the reduced/throttled air flow therethrough, the nebulizer 1 and/or the movement of the container 3—in particular during nebulization and/or priming—is preferably (additionally) damped, preferably such that the force is reduced with which the container 3 is stopped during nebulization, in particular when being used for the first time and/or when air in particular in the conveying tube 9 and/or pressure chamber 11 is pushed out of the nebulizer 1 (so called priming). With other words, the valve 40 or inlet valve 43 serves as a damper within the nebulizer 1 or air pump 30. In this way, shaking of the liquid 2 and/or foam formation is prevented or reduced.

The nebulizer 1, housing part 18, air pump 30 or valve 40 is provided preferably with a support/throttle element 50, such as a ring with a radial slit or the like, in order to support or secure the valve element 42, in particular from below and/or in a respective opening in the insert 33, and/or to throttle the inlet and/or outlet air path. However, other constructional solutions are possible as well.

In the shown embodiment, the air passage 41 is not realized by a separate or additional bore or hole e.g. in the insert 33 as shown in FIGS. 7 and 8 or in the pump piston 31 as indicated in FIG. 5, but by a preferred and defined radial play between the cylinder 32 on one hand and the pump piston 31/modified end 49 on the other hand.

As in the previous embodiments, the leakage passage 41 allows a relatively slow (in comparison to the pressure increase during the tensioning movement or actuation of the air pump 30) pressure compensation or equalization between the pump chamber 39 and the ambient air pressure, preferably within about 2 to 10 s, most preferably within about 4 to 6 s.

Further, the radial play avoids or minimizes the friction between the container 3 and the cylinder 32 so that a negative force acting against the nebulization movement is avoided as such negative force might negatively influence the nebulization process.

In the following, a third embodiment of the container 3 and nebulizer 1 will be described with reference to the further drawings wherein the description will emphasize differences and a new aspect so that the previous features and aspects apply preferably in addition or in a similar manner even if not repeated.

Figure 10:
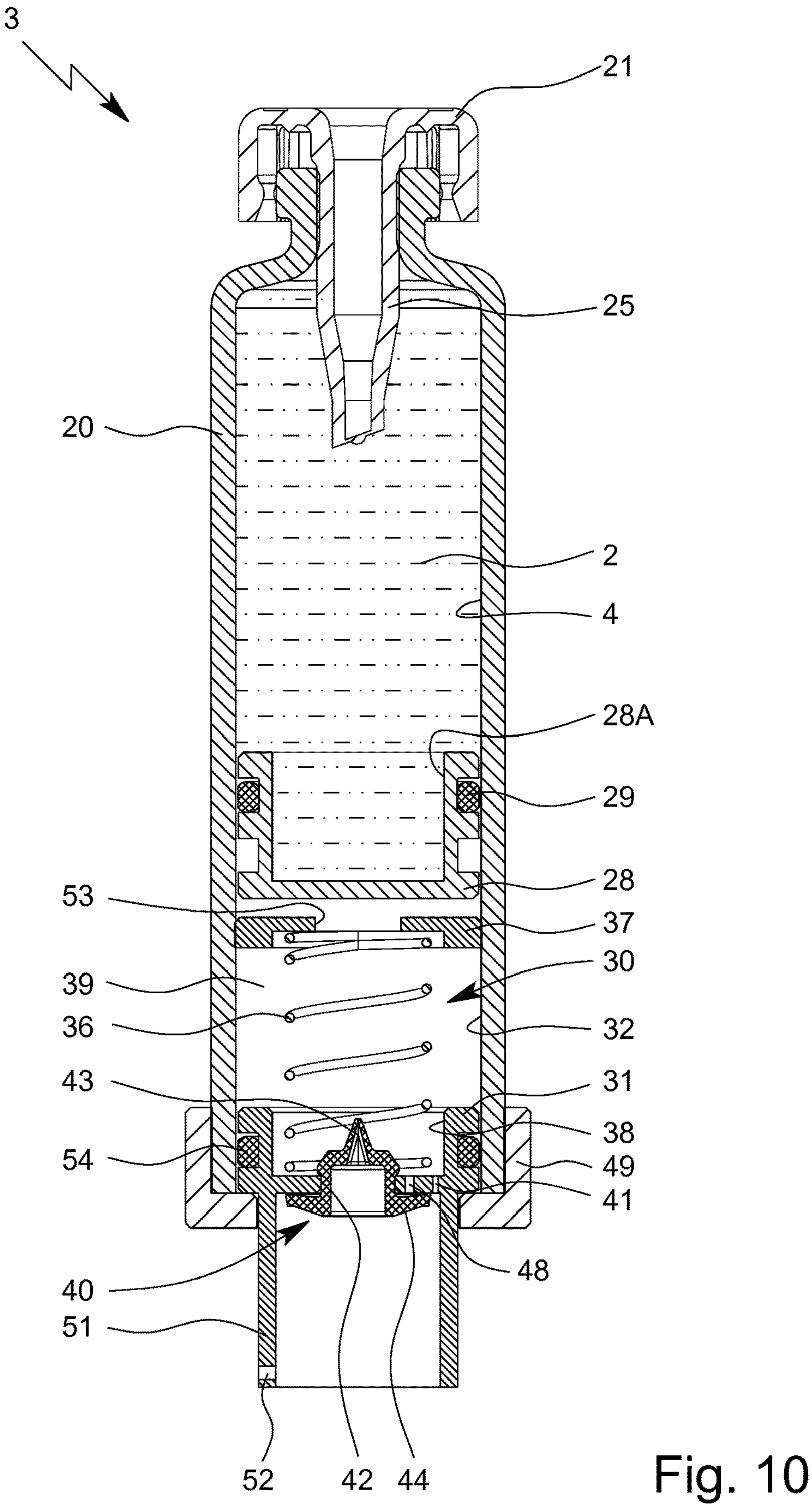
FIG. 10 a schematic section of a third embodiment of the container according to the present invention.
Figure 11:
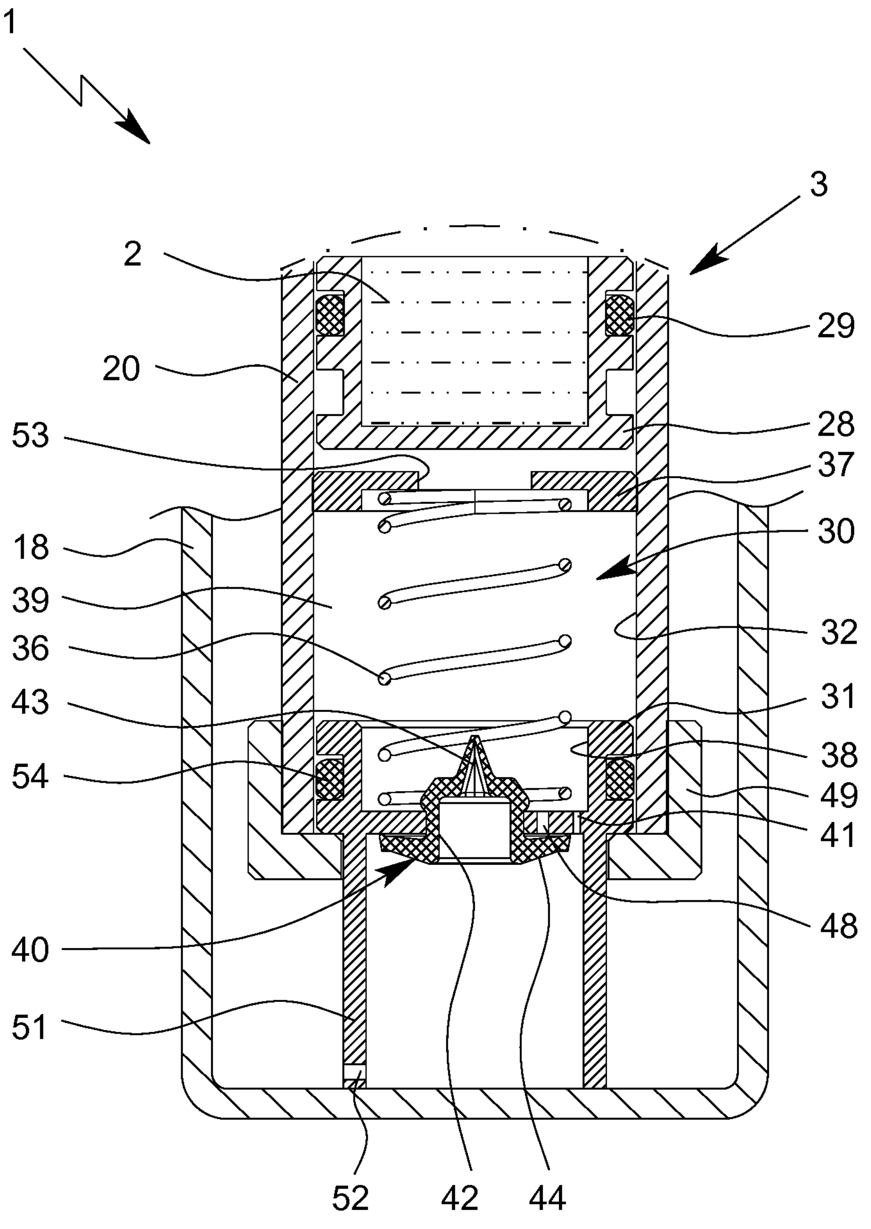
FIG. 11 a schematic section of a lower part of the nebulizer with the container according to the third embodiment in the non-tensioned state.
Figure 12:
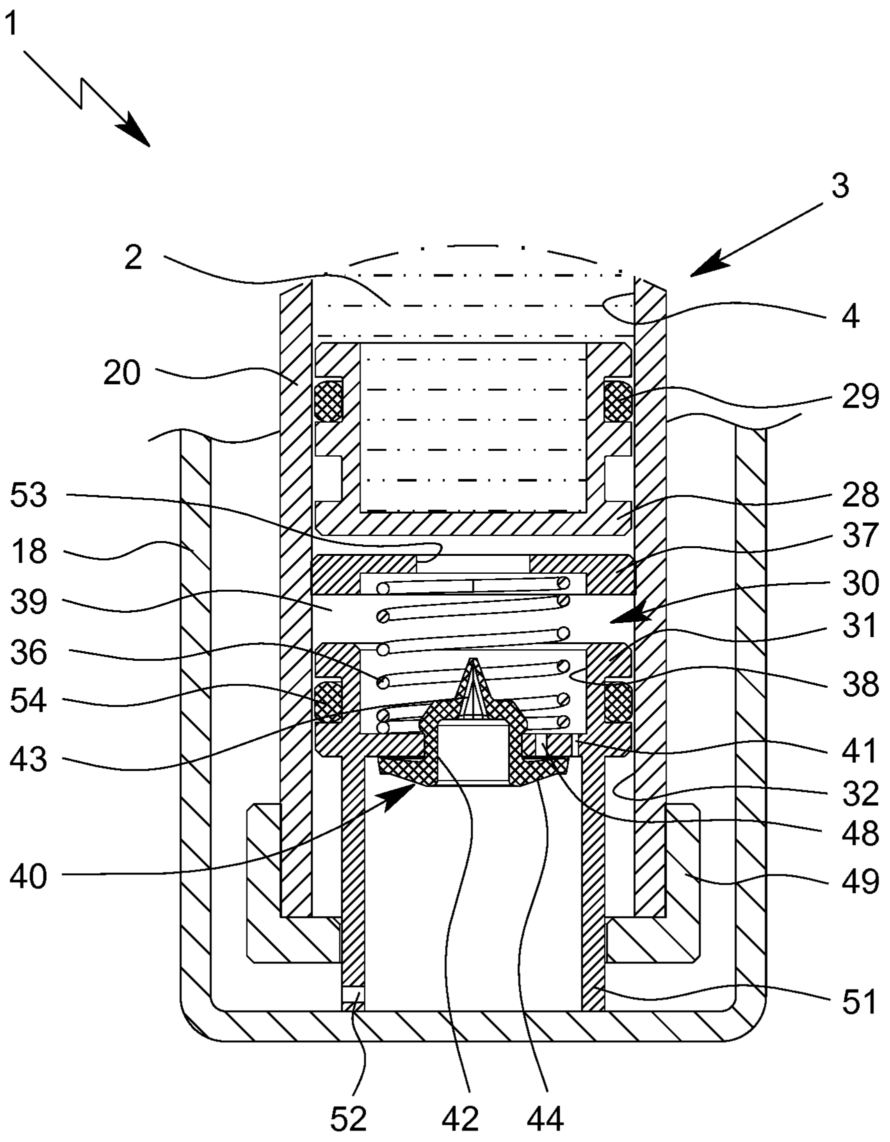
FIG. 12 a schematic section of the lower part of the nebulizer and container similar to FIG. 11, but in a tensioned state.

FIG. 10 shows a schematic section of the third embodiment of the container 3. FIG. 11 shows in a schematic section a lower part (similar to FIGS. 5 and 7 to 9) of a third embodiment of the nebulizer 1 with the container 3 according to the third embodiment in the non-tensioned state. FIG. 12 shows a similar section of the lower part as FIG. 10, but in a tensioned state.

The container 3 preferably comprises the fluid piston 28 axially moveable in the container 3 or its casing 20. In particular, the fluid piston 28 is axially moveable depending on the volume of liquid 2 contained in the container 3 or the variable or collapsible/compressible volume 4 formed therein.

The piston 28 preferably comprises a substantial axial extension, of about 50% or more of the diameter of the cylindric volume 4 to prevent any undesired tilting of the fluid piston 28 because tiling might result in blocking the axial movement of the fluid piston 28.

The fluid piston 28 comprises the central recess 28A which opens here preferably towards the volume 4 or closure 25 in order to optimize or maximize the filling volume of the container 3 with liquid 2.

In the third embodiment, the air pump 30 is preferably arranged or located in the container 3 or its casing 20.

The container 3, air pump 30 or piston 31 preferably comprises the valve 40, inlet valve 43 and/or control valve 44 as already described.

The valve 40 or valve element 42 is preferably inserted in a corresponding through-hole or opening of the pump piston 31 and/or is preferably self-retentive or self-mounting.

In particular, the functionality of the valve 40, inlet valve 43 and/or outlet/control valve 44 is the same as already described with reference to the other embodiments.

Preferably, a seal 54 is arranged between the pump piston 31 and the cylinder 32 formed by the inner side of the container 3 or its casing 20. The seal 54 may be formed by a ring, lip or the like and/or extend around pump piston 31, in particular in a respective annular groove on the circumference of the pump piston 31.

The pump piston 31 is biased into its initial position or axial (end) position shown in FIG. 10 by the return spring 36 or any other suitable biasing means.

The pump piston 31 preferably comprises a recess or annular shoulder or the like as bearing part 38 for receiving and/or guiding the associated end of the return spring 36.

The other end of return spring 36 is held by the bearing part 37 which is preferably located within and/or integrated into the container 3 or its casing 20. Preferably, the bearing part 37 is ring-like and/or provides a preferably central opening 53 for connecting the pump chamber 39 (which is formed between the pump piston 31 and the bearing 37 and surrounded by the cylinder 32) to the rest of the container 3 so that pressurized air can flow towards or act on the liquid 2, variable volume 4 and/or fluid piston 28.

Preferably, the return spring 36 is arranged between the fluid piston 28 and the pump piston 31 and/or extends through or (only) in the pump chamber 39.

The valve 40, valve element 42, inlet valve 43 and/or control valve 44 are preferably located centrally and/or within or in alignment with the return spring 36 and/or at one axial end of the return spring 36.

The container 3, its casing 20 or the modified end 49 preferably forms an axial stop for the pump piston 31, in particular such that the pump piston 31 is inseparable from the container 3 and/or cannot move outside the cylinder 32.

The container 3, air pump 30 or pump piston 31 preferably comprises an actuation element 51 for actuating the pump piston 31.

Preferably, the actuation element 51 is formed unitary with the pump piston 31 and/or is inseparable from the container 3 and/or air pump 30.

In the shown embodiment, the actuation element 51 is preferably formed as a hollow cylinder which extends in axial direction or alignment outside the container 3 or its casing 20.

Preferably, the actuation element 51 comprises at least one venting passage 52 allowing an air exchange of the valve 40, 43 and/or 44 with the environment via the hollow actuating element 51 and the at least one venting passage 52. However, other constructional solutions are possible as well.

The actuation element 51 and the pump piston 31 are preferably unitary or integrally formed and/or are made preferably of plastics.

FIG. 11 shows a section of a lower part of the nebulizer 1 with the container 3 in the non-tensioned state. In this state, the container 3 is in its upper position axially most distant from the housing part 18, in particular from its axial bottom or end. In this state, the pump piston 31 might already be pushed a little bit inwards into the container 3 and/or upwards in FIG. 11 in order to ensure that the actuation element 51 always abuts with its axial free end on the axial end or bottom of the housing part 18.

FIG. 12 shows the lower part of the nebulizer 1 and container 3 in a similar section as FIG. 11, but in the tensioned state. Here, the container 3 has moved (more) into the housing part 18 and/or with its free end or modified end 49 towards to the axial bottom or end of the housing part 18.

Consequently, the actuation element 51 and, thus, the pump piston 31 have been axially moved relative to the container 3 to reduce the volume of the pump chamber 39 and/or to pressurize air for pressurizing the liquid 2 in the container 3 when withdrawing a dose of liquid 2 from the container 3 during the tensioning movement (here downward movement) of the container 3.

Thus, the air pump 30 pressurizes air when tensioning or loading the nebulizer 1.

Preferably, the axial end or modified end 49 of the container 3 guides the actuation element 51 radially so that the pump piston 31 cannot tilt.

Generally, it is preferred that the absolute maximum air pressure of the air pump 30 or pump chamber 39 (this pressure is reached just when the nebulizer 1 reaches the tensioned state) returns automatically and/or gradually to the ambient air pressure within 10 s, in particular about 8 s, preferably about 6 s or less. This return time depends on the dimension of the air leakage and/or construction of the valve 40.

Preferably, the (relative) maximum air pressure (i.e. the pressure difference between the air pressure in the air pump 30/pump chamber 39 and the environment) is more than 80 mbar, in particular more than 100 mbar, and/or less than 300 mbar, in particular less than 200 mbar.

Generally, friction occurs between the fluid piston 28 and the casing 20/cylinder 32. This is known as "glide force". When a dose of liquid 2 is withdrawn from the container 3, an underpressure occurs. This underpressure "sucks" the fluid piston 28 inwards.

When the container 3 has not been used for a long time an additional friction force known as "break loose force" can occur so that the fluid piston 28 sticks to the cylinder wall.

By means of the air pump 30 and/or the application of air pressure during the tensioning, the glide force and in particular the break loose force can be overcome.

Preferably, the container 3, its casing 20 or the cylinder 32 can be made of glass or provide an inner surface of glass in order to reduce the friction and in particular the glide force and/or break loose force.

Alternatively or additionally, the inner surface of the cylinder 32 can be provided with a glide agent, such as silicone, and/or a baking of silicone or the like, in order to reduce the friction and in particular the glide force and/or break loose force.

In particular, a uniform coating preferably of oil can be produced by baking. Such a film is more stable on the inner surface of the cylinder 32 and remains in place even when the container 3 is filled with the liquid 2.

Preferably, the container 3 or casing 20 or inner surface of the cylinder 32 is baked or covered with silicone. This is done preferably just before filling the container 3 with the liquid 2. Prior to the filling, the baked container 3 is preferably sterilized.

The present invention allows, supports or ensures a very precise metering and/or facilitates to keep the volume of the dispensed doses highly constant. Further, it can prevent the formation or growing of any gas bubble within the liquid 2 or bag/variable volume 4. This allows also a minimization or reduction of the total volume of liquid 2 initially provided in the container 3 even if a very high number of doses such as 100 or 150 doses or more are provided.

Figure 13:
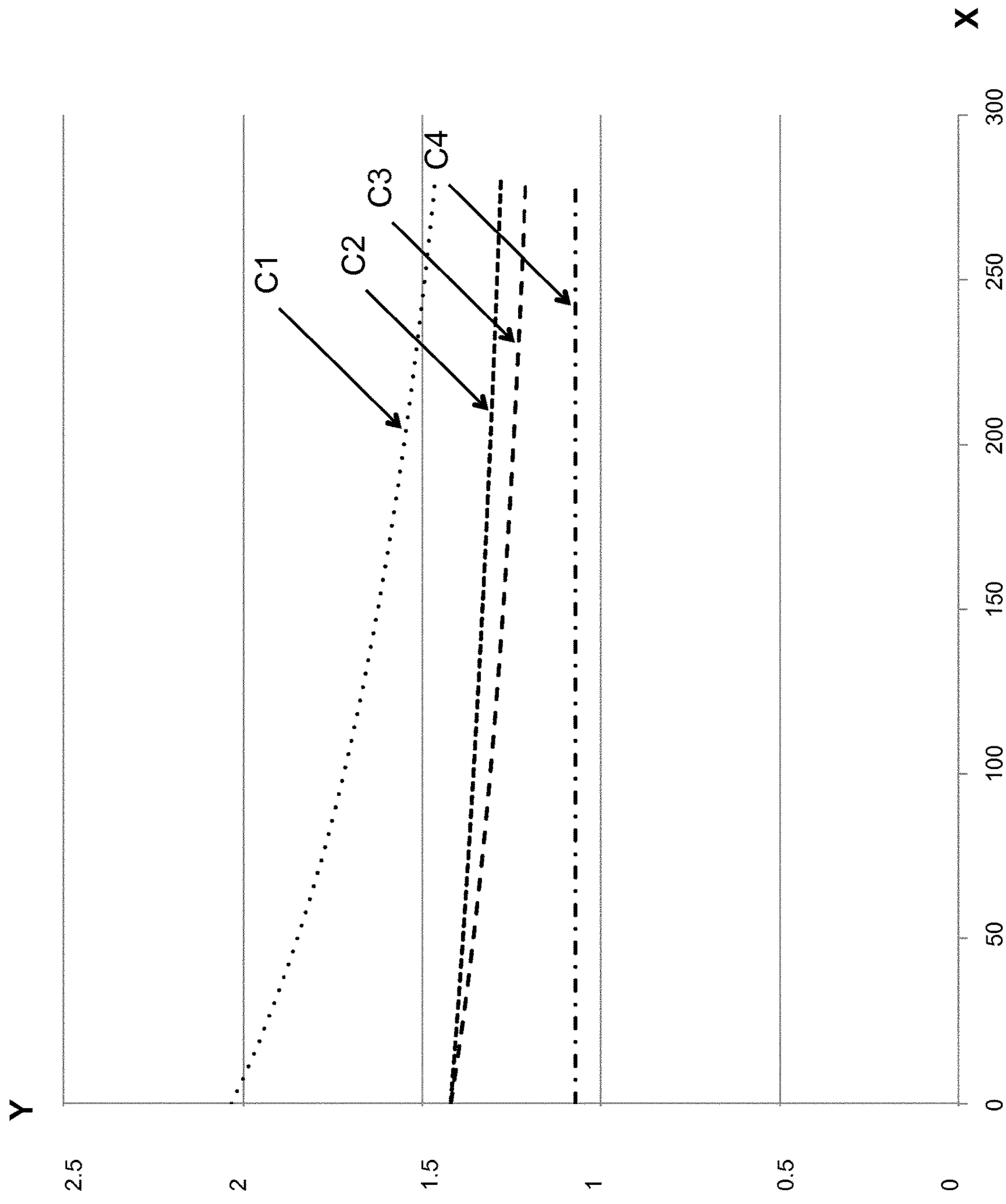
FIG. 13 a diagram of the pressure progression as a function of actuations.

FIG. 13 shows schematically in a diagram different pressure progressions as a function of actuations (number of dispensed doses of liquid 2) for the nebulizer 1/air pump 30 according to the first embodiment (shown in FIGS. 1, 2 and 5) with the container 3 according to the first embodiment (shown in FIG. 3).

The X axis denotes the number of actuations. The axis starts with "0" which means that no dose of liquid 2 has been withdrawn or dispensed from the container 3, i.e. the container 3 or its volume 4 is completely filled at this point.

The Y axis denotes the pressure in bar. The pressure of 1.0 bar represents or corresponds to the normal pressure (ambient air pressure) in the calculation.

As already mentioned, a certain pressure difference must be applied to overcome any inertia and/or friction or adhesion to ensure the desired collapse of the variable volume 4, here the bag, of the container 3 so that any underpressure in the variable volume 4 can be avoided or at least minimized during withdrawal of a dose of the liquid 2 and/or so that a very precise/defined and in particular constant volume of liquid 2 is withdrawn during each tensioning stroke or pump process or loading of the fluid pump 5. This pressure difference is particularly between 40 mbar and 100 mbar and has been assumed to be 70 mbar in the shown diagram. This is reflected by curve C4 which shows the absolute pressure corresponding to the desired or assumed pressure difference of 70 mbar which should be reached or exceeded to ensure or facilitate precise metering as explained.

The curves C1 to C3 show different calculations of the pressure progression under different conditions. The progression of curve C1 has been confirmed by respective experiments (without valve 40/43). Further, the values used for the calculations correspond to the sample used for experiments.

The curves C1 to C3 show the maximum air pressure that is reached during an actuation or tensioning.

In all cases, the air volume of the container 3 is about 2 ml at the beginning and the pump volume of the air pump 30 is about 3.5 ml.

For curve C1, the total volume of the air pump 30 is about 5 ml and the volume of each dose of withdrawn liquid 2 is 15 microliters.

For curve C2, the total volume of the air pump 30 is about 10 ml and the volume is 15 microliters for each dose of liquid 2 that is withdrawn during each actuation. In particular, the effective length of the cylinder 32/insert 33 is doubled/varied in order to double/vary the total volume of the air pump 30.

For curve C3, the same volume, i.e. about 10 ml, is the total volume of the air pump 30, wherein the volume of each dose of liquid 2 is 30 microliters.

It is visible that all three curves C1 to C3 lie significantly above the desired minimum curve C4 so that the desired minimum pressure (difference) is reached or exceeded and precise metering can be expected or supported.

The difference between curve C1 on one hand and curves C2 and C3 on the other hand shows that the total volume of the air pump 30, of an air buffer (the total air volume, i.e. sum of air pump 30 and completely filled container 3 minus the pump volume of the air pump 30, i.e. about 3.5 ml for C1 and about 8.5 ml for C2 and C3) and/or of both, the air pump 30 and container 3, influences the dependency on the number of actuations, in particular such that the gradient of the curves C2 and C3 is less than the gradient of curve C1 with lower total volume/air buffer. Therefore, a higher total air volume/air buffer may be advantageous to achieve a more uniform operation.

Further, the above comparison shows that the lower total air volume leads to a higher air pressure level which might lead to undesired liquid leakage. Thus, the control of the air pressure—preferably by means of valve 40 or 43—might be advantageous in particular in this case. However, the effect of the optional valve 40/43 has not been considered in curves C1 to C3.

The comparison of curves C2 and C3 shows that the influence of the volume of the withdrawn dose of the liquid 2 is relatively small in comparison to the influence of the total air volume, but with higher volume of each dose the curve C3 declines faster than the curve C2 with smaller volume of each dose.

Figure 14:
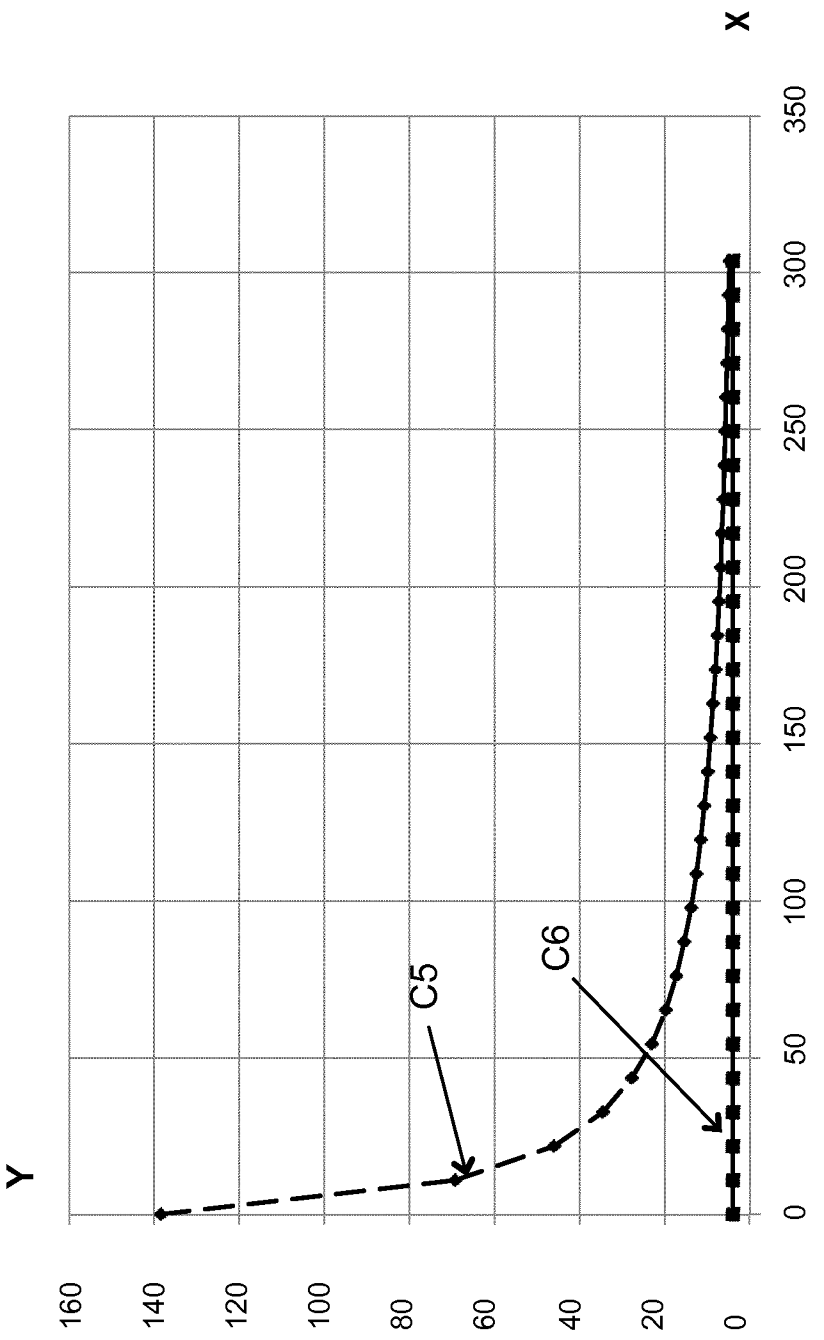
FIG. 14 another diagram of the pressure progression as a function of actuations.

FIG. 14 shows schematically in another diagram the pressure progression as a function of the actuations for the nebulizer 1/container 3/air pump 30 according to the third embodiment shown in FIGS. 10 to 12.

The X axis denotes the number of actuations. The axis starts with "0" which means that no dose of liquid 2 has been withdrawn or dispensed from the container 3, i.e. the container 3 or its volume 4 is completely filled at this point.

The Y axis denotes the force or pressure difference acting on the fluid piston 28 to pressurize the liquid 2 in the container 3/volume 4. The Y axis uses a scale which is proportional to the actual pressure or force values.

For curve C5, the pump volume of the air pump 30 is about 1.4 ml and the total air volume of the container 3 including the volume of the air pump 30 is about 1.55 ml at the beginning with completely filled container 3. Further, a dose of 15 μl is withdrawn or discharged during each actuation.

The curve C5 has been calculated based on the above values and shows the maximum force or pressure difference which acts on the fluid piston 28 during an actuation or tensioning.

The curve C5 shows a very strong dependency or steep gradient, in particular at the beginning. Consequently, the (maximum) air pressure (difference) and force acting on the fluid piston 28 and, thus, on the liquid 2 in the container 3 varies highly with the actuations or over the time of usual use of the container 3.

The high dependency or high gradient mentioned above results in particular from the minimal or little air buffer (difference between the total air volume and the pump volume; here caused by a minimum gap or air space between the pistons 28 and 31 even with completely filled container 3) at the beginning, i.e. with completely filled container 3. Thus, increasing the air buffer can be advantageous, but reduces the available volume 4 for the liquid 2 when the total size of the container 3 is kept constant. Thus, it might be very helpful to control or limit the maximum air pressure, in particular by means of the valve 40 or 43, so to keep the force or pressure difference acting on the fluid piston 28 and on the liquid 2 in the container 3 at a desired level. However, the effect of the optional valve 40/43 has not been considered in curve C5.

The diagram of FIG. 14 shows schematically as curve C6 a desired minimum force or pressure difference which should be reached or exceeded in order ensure that a potential break loose force for moving the fluid piston 28 is (surely) overcome.

In the following, further preferred embodiments of the nebulizer 1/container 3 will be described with reference to FIGS. 15 to 26, wherein only relevant differences of new aspects/features are described or emphasized and wherein the previous explanation and description applies preferably additionally or correspondingly even without repetition. In particular, the nebulizer 1/container 3 according to FIGS. 15 to 26 might comprise one or several features described with reference to FIGS. 1 to 14, in particular to FIGS. 3 and 7 to 9, or vice versa.

Figure 15:
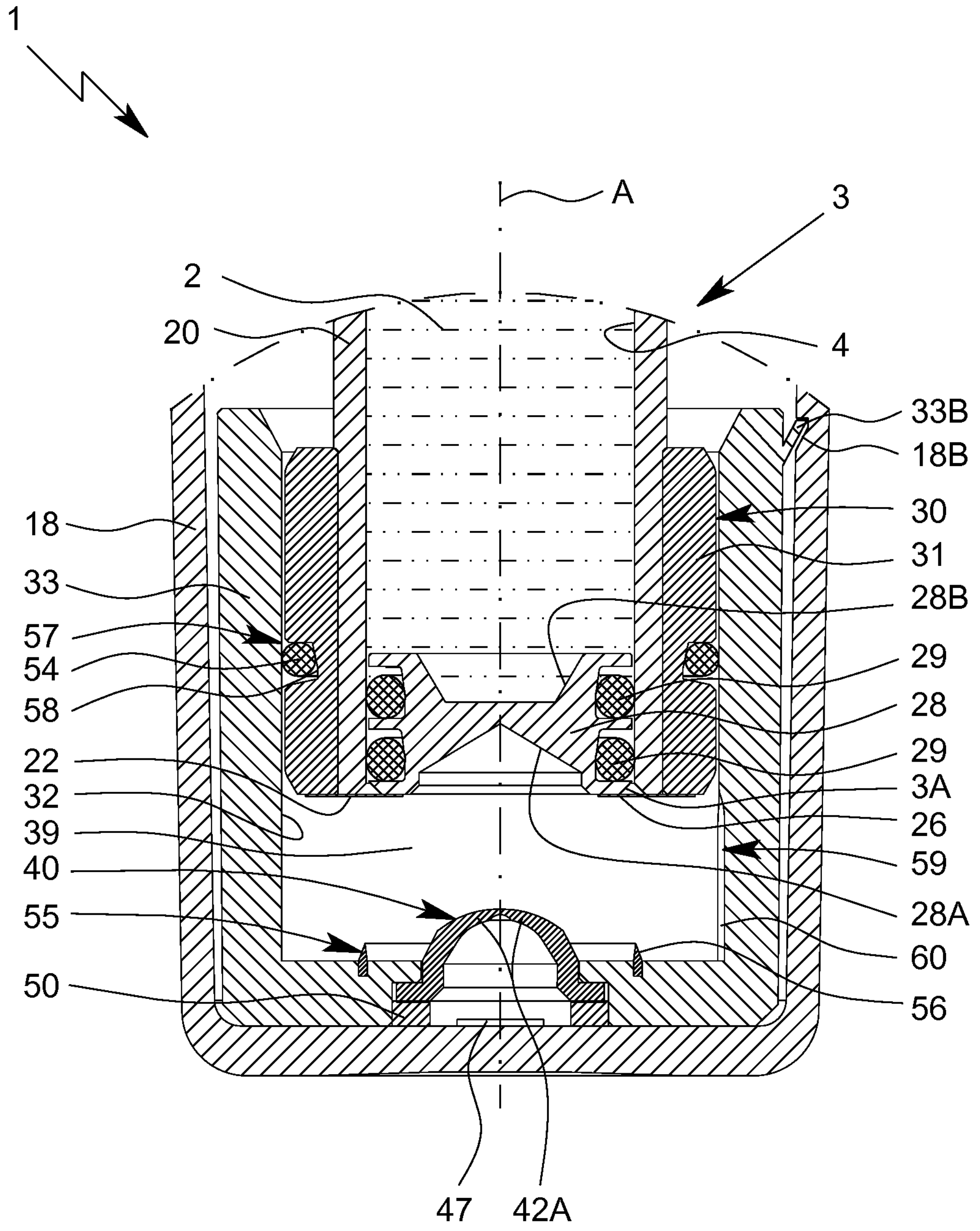
FIG. 15 a schematic section of a lower part of the nebulizer according to another embodiment in a delivery state.
Figure 16:
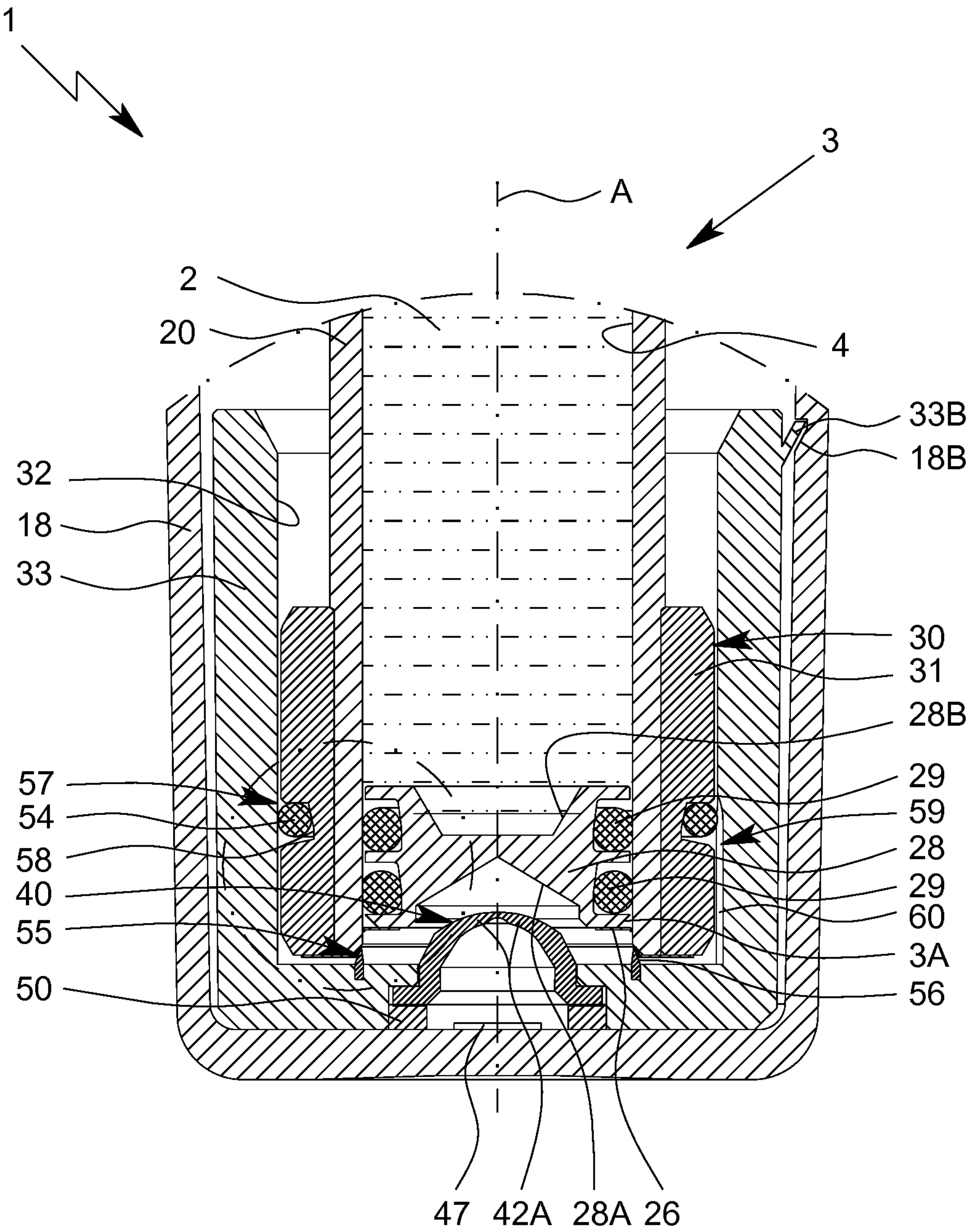
FIG. 16 a schematic section of the lower part of the nebulizer according to FIG. 15 in the tensioned state.
Figure 17:
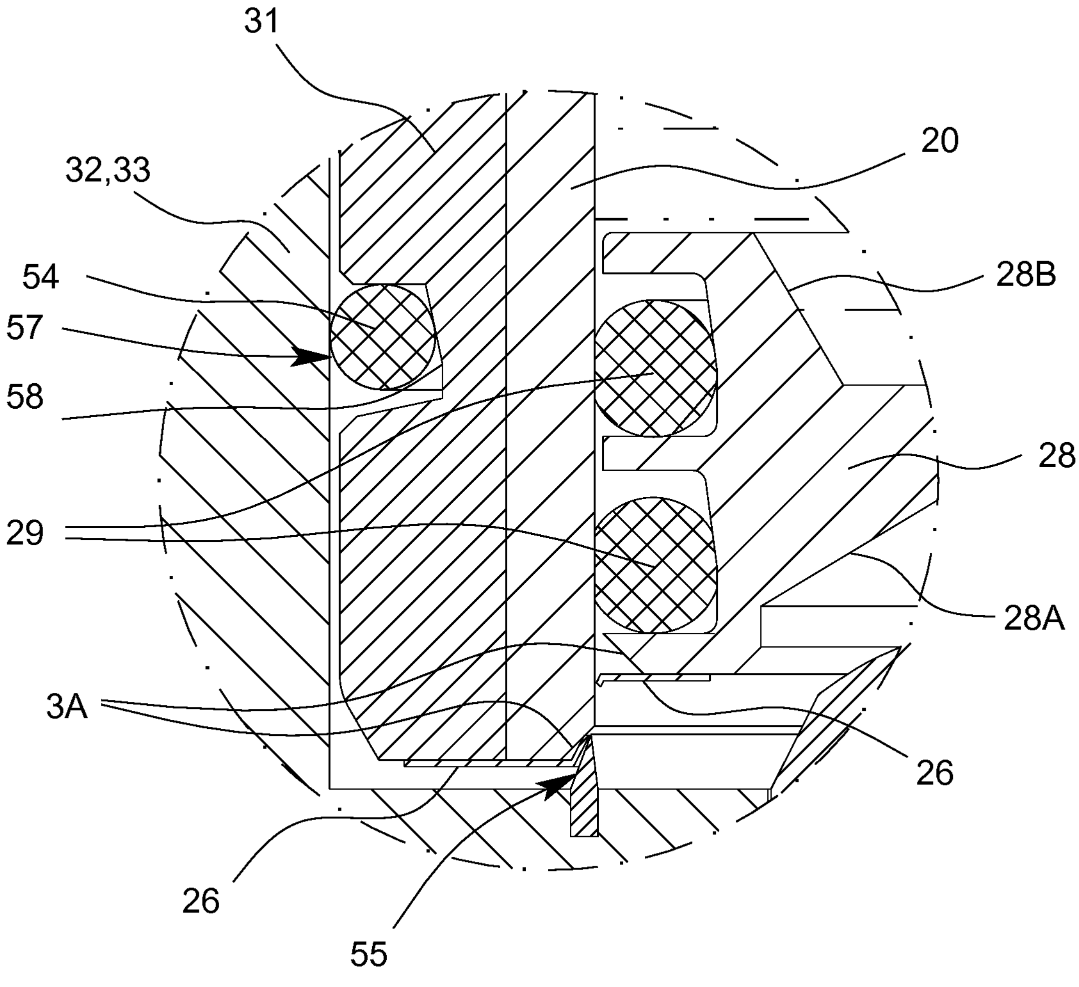
FIG. 17 a partial enlargement of FIG. 16.
Figure 18:
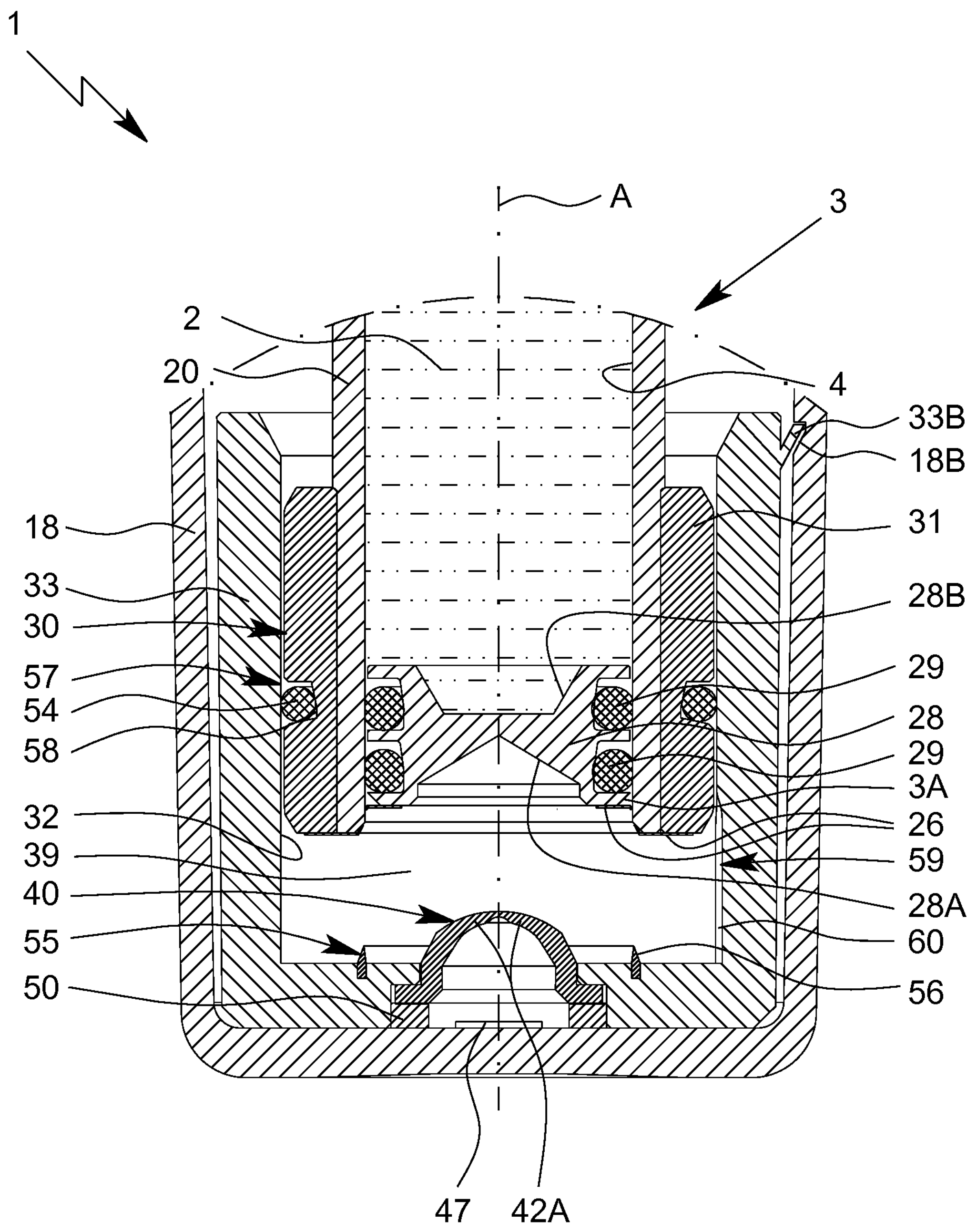
FIG. 18 a schematic section of the lower part of the nebulizer according to FIG. 15 in the non-tensioned state.

FIG. 15 shows in a schematic section another preferred embodiment of the nebulizer 1 in the delivery/unused state. FIG. 16 shows the nebulizer 1 when being used/tensioned for the first time, i.e. when the seal 26 attached to the axial end of the container 3 is opened. FIG. 17 shows a partial enlargement of the nebulizer 1 in order to illustrate the opening of the seal 26. FIG. 18 shows the nebulizer 1 after being activated, i.e. after nebulization of a dose of the liquid 2, and, thus, in the non-tensioned state.

The delivery/unused state of the nebulizer 1/container 3 is preferably the state in which the nebulizer 1/container 3 is delivered from the factory.

Preferably, the nebulizer 1 is not tensioned in the delivery/unused state of the nebulizer 1.

Mostly preferred, the container 3, in particular its seal 26, is intact/unopened/unpierced in the delivery/unused state of the container 3. Preferably (in case of a container 3 with a fluid piston 28), the fluid piston 28 sits flush with the axial end of the container 3, casing 20 and/or pump piston 31 in the delivery/unused state of the container 3.

As already mentioned, the insert 33 is preferably attached to the housing part 18 in a force-fit and/or form-fit manner and/or by glueing, welding or the like. The FIGS. 15 to 18 illustrate a possible form-fit connection between the insert 33 and the housing part 18, preferably wherein the insert 33 is clipped into the housing 18. For example, the insert 33 might be equipped with a protrusion 33B and the housing part 18 with a corresponding recess 18B or vice versa, preferably wherein the protrusion 33B protrudes into the recess 18B when the insert 33 is clipped into the housing 18. However, other constructional solutions are possible as well.

As already mentioned, the container 3 might be provided with an (axial) seal 26, preferably wherein the seal 26 covers or seals the container 3, in particular its axial end or base 22, mostly preferred the gap between the pump piston 31 and the cylinder 32.

The seal 26 serves as a barrier against contamination, e.g. dust, and/or can be used as a quality seal and/or label and/or might comprise notes or user instructions.

In the embodiment shown in FIGS. 15 to 18, the seal 26 is embodied as a ring, in particular such that the (first) recess 28A is axially accessible and/or not covered by seal 26. However, other constructional solutions are possible as well, in particular wherein the seal 26 covers the entire axial end of the container 3, as will be described later.

Preferably, the seal 26 is attached to the bottom/axial end of the container 3. In the current embodiment, the seal 26 is preferably attached, e.g. adhered, to the fluid piston 28 on the one hand and the casing 20 and/or pump piston 31 on the other hand. In this way, no parts fall off when the seal 26 is opened. However, other solutions are possible as well, as will be described later with reference to FIGS. 20 to 23.

The nebulizer 1 preferably comprises an opening device 55 for opening the seal 26, preferably when using/tensioning the nebulizer 1 for the first time.

In particular, the opening device 55 is adapted to pierce or cut open the seal 26, preferably between the pump piston 31 and the cylinder 32 and/or in a circular/annular manner and/or around the axis A and/or such that air can flow through the seal 26.

Preferably, the opening device 55 comprises one or several features of the aeration device 18A as described with reference to FIG. 5.

Preferably, the opening device 55 comprises at least one opening element 56, preferably wherein the opening element 56 comprises a sharp/tapered end/tip in order to open, pierce or cut open the seal 26.

In the current embodiment, the opening device 55, in particular opening element 56, is embodied as a ring, preferably wherein the opening device 55 or opening element 56 extends around the valve 40. However, other constructional solutions are possible, in particular wherein the opening device 55 or opening element 56 is embodied as a spike or set of spikes, as will be described with reference to FIGS. 20 to 24.

The opening device 55 is preferably attached/connected to the housing part 18, cylinder 32, insert 33 and/or valve 40, preferably in a form-fit and/or force-fit manner and/or by welding. In particular, constructional solutions are possible wherein the opening device 55 is formed integrally with the housing part 18, cylinder 32, insert 33 and/or valve 40, as will be explained later with reference to FIG. 23.

According to another preferred embodiment, the opening device 55 is spring-mounted for tolerance compensation.

Preferably, the opening device 55, in particular its opening element 56, protrudes into the pump chamber 39, in particular axially and/or from a side opposite to the pump piston 31 and/or the fluid piston 28.

In the current embodiment, the valve 40 protrudes preferably further into the pump chamber 39 than the opening device 55. With other words, the valve 40 is higher than the opening device 55 or its opening element 56.

As already mentioned, the fluid piston 28 can comprise a (central) recess 28A on a side turned away from the volume 4, i.e. facing the pump chamber 39, or on a side facing the volume 4, i.e. turned away from pump chamber 39.

In the embodiment shown in FIGS. 15 to 18, the fluid piston 28 comprises two recesses 28A, 28B on different sides, i.e. a (first) recess 28A on a side turned away from the volume 4 and/or facing the pump chamber 39 and a (second) recess 28B on a side facing the volume 4 and/or turned away from the pump chamber 39.

Preferably, the first recess 28A is adapted to axially receive the valve 40, inlet valve 43 and/or control valve 44, in particular such that the container 3, pump piston 31 and/or base 22 can be moved axially towards the bottom of the housing part 18, cylinder 32 and/or insert 33, in particular towards the opening device 55, without interfering with and/or contacting the valve 40, inlet valve 43 and/or control valve 44 and/or such that the opening device 55 can open/pierce the seal 26.

In particular, due to the first recess 28A it is possible to open/pierce the seal 26 by means of the opening device 55 although the valve 40 is higher than the opening device 55. However, other constructional solutions are possible as well. In particular, the opening device 55 might protrude further into the pump chamber 39 than the valve 40. For example, the valve 40 could be embedded into the insert 33 or housing part 18, in particular such that the opening device 55 protrudes further into the pump chamber 39 than the valve 40. In such an embodiment, the seal 26 could cover the entire axial end of the container 3.

Preferably, the opening device 55, the opening element(s) 56, the valve 40 and/or the first recess 28A are concentrically arranged, preferably wherein the (outer) diameter of the preferably annular/circular arranged opening device 55 or its opening elements 56 is larger than the (outer) diameter of the valve 40 and/or first recess 28A, in particular such that the opening device 55 or its opening element(s) 56 open(s)/cut(s)/pierce(s) the seal 26 in/along a circle that is concentrical to the valve 40 and/or first recess 28A and/or comprises an (outer) diameter that is larger than the (outer) diameter of the valve 40 and/or first recess 28A.

Mostly preferred, the container 3, in particular its casing 20, and/or the fluid piston 28 comprise(s) a preferably circumferential/circular recess 3A to (axially) receive the opening device 55, in particular its opening element(s) 56, preferably wherein the recess 3A is arranged on a surface of the container 3, in particular its casing 20, and/or the fluid piston 28 facing the opening device 55, in particular its opening element(s) 56. In this way, opening/piercing of the seal 26 is facilitated and the opening device 55, in particular its opening element(s) 56, do (es) not hit rigid material. Further, due to a circumferential/circular recess 3A the orientation of the container 3 relative to the opening device 55, in particular its opening element(s) 56, is irrelevant.

The (second) recess 28B is preferably adapted to axially receive the closure 25, in particular its axial end, mostly preferred the conveying tube 9 (not shown) or a preferably funnel-shaped connection/port (not shown) for the conveying tube 9 extending through the closure 25, preferably wherein the conveying tube 9 or a connection/port extends only a few mm into the volume 4 or is flush with the closure 25. Further, due to the (second) recess 28B the volume 4 is increased.

Preferably, the fluid piston 28 serves as an axial seal for the closure 25 and/or is adapted to close/seal the container 3, in particular closure 25, from the inside and/or when the fluid piston 28 reaches the closure 25 and/or is moved axially against the closure 25.

Mostly preferred, the (second) recess 28B is adapted to seal/close the closure 25 when the fluid piston 28 is axially moved into its upper axial (end) position.

Due to the (second) recess 28B it is possible to increase the volume 4 and, thus, the number of doses that can be withdrawn from the volume 4 and/or container 3. Further, the container 3, in particular the closure 25, can be closed from the inside when the fluid piston 28 reaches its upper axial (end) position and cannot be moved further towards the closure 25. In this way, a leakage can be prevented, e.g. when the container 3 is removed.

Another advantage of the recesses 28A, 28B is the weight reduction without a reduction of the (radial) contact surface of the fluid piston 28 and, thus, without increasing the risk to twist/tilt the fluid piston 28 within the container 3/casing 20.

Further, the elasticity of the fluid piston 28 is increased (in particular when being made out of elastomer, thermoplastic and/or thermoset, mostly preferred of rubber), in particular such that the fluid piston 28 fits sealingly into the container 3 or casing 20, preferably such that an (additional) seal 29 can be omitted, as will be described with regard to FIGS. 20 to 23.

As already mentioned, the fluid piston 28 preferably comprises a (radial) seal 29, preferably wherein the seal 29 acts between the fluid piston 28 and the casing 20. Preferably, the seal 29 is embodied as a seal ring, i.e. O-ring, a sealing lip, a—preferably two-component injection—molded seal or the like.

Mostly preferred, the seal 29 is placed into a circumferential groove of the fluid piston 28.

As best seen in enlargement shown in FIG. 17, the seal 29 might be equipped with an axial play. In particular, the groove containing the seal ring might be broader/wider than the seal ring, in particular such that the fluid piston 28 or its base body can be moved axially relative to the casing 20 without moving the seal 29 relative to the casing 20. In this way, a (remaining) pressure difference between the volume 4 and the pump chamber 39 can be balanced or reduced, in particular after tensioning and/or actuating the nebulizer 1.

In the present embodiment, the fluid piston 28 preferably comprises several, here two, seals 29, preferably wherein the seals 29 are axially spaced apart from each other.

As already described in particular with reference to the embodiment shown in FIGS. 10 to 12, the nebulizer 1 or container 3 can comprise a (radial) seal 54 that is arranged between the pump piston 31 and the cylinder 32 and/or that acts between the pump piston 31 and the cylinder 32, in particular such that the gap between the cylinder 32 and the pump piston 31 is sealed.

The seal 54 is preferably embodied as a seal ring, i.e. O-ring, a (preferably double) sealing lip, a—preferably two-component injection—molded seal or the like.

In the present embodiment, the seal 54 is preferably an O-ring. However, other solutions are possible as well, in particular wherein the seal 54 is embodied as a (double) sealing lip, that is injection molded onto the pump piston 31 or cylinder 32 and/or protrudes radially from the pump piston 31 or cylinder 32.

Preferably, the seal 54 extends around the pump piston 31, in particular in a circumferential groove thereof.

Mostly preferred, the nebulizer 1 or container 3 comprises a sealing device 57, preferably wherein a sealing device 57 comprises or forms the seal 54 and/or acts between the pump piston 31 and the cylinder 32.

The sealing device 57, in particular seal 54, is preferably adapted to compensate tolerances between the housing part 18, cylinder 32 or insert 33 on the one hand and the container 3, casing 20 or pump piston 31 on the other hand.

Preferably, the sealing device 57 comprises/causes a (variable) sealing effect between the pump piston 31 and the cylinder 32, preferably wherein the sealing effect depends on the direction of movement of the pump piston 31 relative to the cylinder 32.

Preferably, the sealing device 57 is adapted to increase the sealing effect, to close the gap between the pump piston 31 and the cylinder 32 and/or to seal the pump piston 31 against the cylinder 32 during withdrawal of a dose of the liquid 2 from the container 3 or volume 4 and/or during tensioning the nebulizer 1 and/or when the pump piston 31 is moved towards the bottom of the housing part 18.

Preferably, the sealing device 57 is adapted to decrease the sealing effect, to loosen the seal 57 and/or to open the gap between the pump piston 31 and the cylinder 32 during pressurizing the dose of the liquid 2 for nebulization and/or during dispensing the dose of the liquid 2 and/or when the pump piston 31 is moved towards the mouthpiece 13.

Mostly preferred, the pump piston 31 is only sealed against the cylinder 32 and/or the pump chamber 39 is only closed by means of the sealing device 57 or its seal 54 during tensioning/cocking/loading of the nebulizer 1 and/or when the pump piston 31 is moved towards the bottom of the housing part 18 and/or when the air pump 30 is to be used.

The sealing device 57 is preferably adapted to apply a (variable) force/pressure on the seal 54, the pump piston 31 and/or the cylinder 32, and/or a variable friction between the pump piston 31 and the cylinder 32, in particular wherein the force/pressure/friction level depends on the direction of movement of the pump piston 31 relative to the cylinder 32.

Preferably, the sealing device 57 is adapted to increase the force/pressure/friction between the pump piston 31 and the cylinder 32 depending on the direction of movement of the pump piston 31 within the cylinder 32.

Mostly preferred, the sealing device 57 is adapted to increase the force/pressure/friction between the pump piston 31 and the cylinder 32 during withdrawal of a dose of the liquid 2 from the container 3 or volume 4 and/or during tensioning the nebulizer 1 and/or when the pump piston 31 is moved towards the bottom of the housing part 18.

Mostly preferred, the sealing device 57 is adapted to decrease the force/pressure/friction between the pump piston 31 and the cylinder 32 during pressurizing the dose of the liquid 2 for nebulization and/or during dispensing the dose of the liquid 2 and/or when the pump piston 31 is moved towards the mouthpiece 13.

With other words, the sealing device 57 provides two different sealing states/positions. In a first sealing state/position, shown in FIGS. 15 to 17, the pump piston 31 is sealed against the cylinder 32, preferably with high force/pressure, and/or a strong seal, i.e. a seal having a high (mechanical) strength, between the pump piston 31 and the cylinder 32 is established.

In a second sealing state/position, shown in FIG. 18, the pump piston 31 is sealed against the cylinder 32 with less force/pressure than in the first sealing state/position or no force/pressure at all. In the second sealing state/position, the seal between the pump piston 31 and the cylinder 32 has preferably a lower (mechanical) strength than in the first sealing state/position.

Due to the sealing device 57, i.e. the variable sealing effect, it is possible to reduce/minimize the impact of the air pump 30 on the dispensing/nebulizing process. In particular, the container 3 can be moved with less frictional resistance during the dispensing/nebulizing process (than during the tensioning/loading process and/or fluid withdrawal).

The sealing device 57 preferably comprises a (circumferential) groove 58, preferably wherein the groove 58 extends around the pump piston 31 or cylinder 32.

Preferably, the seal 54 is arranged in the groove 58.

The groove 58 is preferably broader than the seal 54, in particular such that the seal 54 is (axially) movable within the groove 58, i.e. up and down. With other words, the sealing device 57 comprises preferably an axial play, in particular such that a seal 54 can move axially within the groove 58.

As best seen in FIG. 17, the groove 58, in particular its width, is preferably tapered and/or comprises preferably a (radial) depth that varies along its axial extension, i.e. along its width.

The depth of the sealing device 57, in particular groove 58, is preferably the radial extent of the groove 58. The width of the sealing device 57, in particular groove 58, is preferably the axial extent of the groove 58.

Generally, the terms "radial" and "axial" relate preferably to the main/central axis A of the nebulizer 1 or container 3.

Preferably, the main/central axis A of the nebulizer 1 or container 3 is the longitudinal, rotational and/or motion axis of the—preferably cylindrical and/or elongated—nebulizer 1 or container 3.

In particular, the main/central axis A is formed or defined by the reciprocating movement and/or the main/longitudinal extension of the nebulizer 1 or container 3 and/or the main direction of nebulization.

Preferably, the groove 58 deepens towards the bottom or base 22 of the container 3 and/or tapers towards the head 21 of the container 3.

When the container 3 and/or the pump piston 31 is moved downwards, i.e. towards the bottom of the housing part 18 and/or away from the mouthpiece 13, and/or during tensioning of the nebulizer 1 (as shown in FIGS. 15 to 17), the seal

54 is preferably moved into the contrary direction within the groove 58, i.e. upwards, and/or into the narrower portion of the groove 58 and/or is pressed with a greater force against the pump piston 31/cylinder 32. This increases the force/pressure/friction and/or the sealing effect between the pump piston 31 and cylinder 32, in particular such that no air can leak from the pump chamber 39 through the gap between the pump piston 31 and cylinder 32.

When the container 3 and/or the pump piston 31 is moved upwards, i.e. away from the bottom of the housing part 18 and/or towards the mouthpiece 13, and/or during dispensing/nebulizing a dose of the liquid 2 (as shown in FIG. 18), the seal 54 moves preferably downwards in the groove 58 and/or into its deeper portion. In this way, the seal 54 is pressed with less force against the pump piston 31/cylinder 32. Thus, the force/pressure/friction and/or the sealing effect between the pump piston 31 and cylinder 32 is decreased. In particular, the container 3 can be moved with less frictional resistance during the dispensing/nebulizing process, i.e. due to the variable friction of the sealing device 57 it is possible to reduce/minimize the impact of the air pump 30 on the dispensing/nebulizing process.

Further, the sealing device 57 can be adapted to provide an air passage between the pump piston 31 and cylinder 32 and/or to unseal/open the gap between the pump piston 31 and cylinder 32 during nebulization and/or dispensing the dose of the liquid 2, in particular such that air can leak through the gap between the pump piston 31 and the cylinder 32.

Optionally, the nebulizer 1, in particular the air pump 30, comprises a pressure control device 59, hereafter referred to as the control device 59, preferably for pressure compensation and/or wherein the control device 59 is adapted to control and/or limit the air pressure within the air pump 30 or its pump chamber 39, preferably independent from the velocity of tensioning/cocking/loading of the nebulizer 1, i.e. the speed with which the housing part 18 is rotated relative to the upper housing part 16.

Preferably, the nebulizer 1, in particular the control device 59, comprises an (over-) pressure means/depressurization means/pressure relief means/valve 60, hereinafter referred to as pressure relief means 60.

Preferably, the control device 59 comprises the pressure relief means 60 and, further, the valve 40, the inlet valve 43 and/or the control valve 44.

Mostly preferred, the control device 59, in particular its pressure relief means 60, is adapted to decrease the air pressure in the air pump 30 or its pump chamber 39, preferably dependent on the (axial) position of the container 3 within the nebulizer 1 or housing part 18.

In contrast to the valve 40, inlet valve 43 and/or control valve 44, the pressure relief means 60 is activatable/openable dependent on the (axial) position of the container 3 within the nebulizer 1, in particular housing part 18, and/or of the pump piston 31 within the cylinder 32 and/or independent from the (actual) pressure in the air pump 30 or pump chamber 39 (whereas the valve 40, inlet valve 43 and/or control valve 44 are/is adapted to open dependent on the air pressure in the air pump 30 or its pump chamber 39).

The control device 59, in particular its pressure relief means 60, is preferably embodied as a bypass or a bypass channel which is integrated into the pump piston 31 or cylinder 32. Preferably, the control device 59, in particular its pressure relief means 60, operates and/or is embodied as an overpressure valve that opens depending on the (axial) position of the container 3 within the nebulizer 1.

Preferably, the control device 59, in particular pressure relief means 60, is formed by a longitudinal/axial groove within the pump piston 31 or cylinder 32, preferably wherein the groove extends at least essentially parallel to the central axis A of the nebulizer 1. However, other constructional solutions are possible as well.

The control device 59, in particular the pressure relief means 60, is preferably activated or activatable and/or opened or openable, when a predefined (axial) position of the pump piston 31 within/relative to the cylinder 32 is reached, in particular when the pump piston 31 reaches its first/lower axial (end) position, and/or (only) during tensioning of the nebulizer 1, in particular at the end of the tensioning process (as shown in FIG. 16).

Preferably, the control device 59, in particular the pressure relief means 60, is adapted to bypass the sealing device 57, in particular seal 54, and/or to pneumatically connect the air pump 30, in particular its pump chamber 39, to the atmosphere/environment, in particular such that a (remaining) overpressure—compared to the ambient pressure—in the nebulizer 1 or air pump 30, in particular its pump chamber 39, can be compensated.

The control device 59, in particular the pressure relief means 60, is preferably activated and/or opened when the seal 54 of the sealing device 57 reaches and/or is on the same level as the pressure relief means 60, in particular the axial (upper) end of the bypass channel, as shown in FIG. 16. Preferably, this is the case when the pump piston 31 reaches its first/lower axial (end) position within the cylinder 32 and/or when the volume of the pump chamber 39 is minimized. However, other solutions are possible as well, e.g. wherein the pump piston 31 opens a resilient flap or the like.

When being activated/opened (as shown in FIG. 16), the control device 59, in particular its pressure relief means 60, bypasses the sealing device 57, in particular seal 54, and/or pneumatically connects the air pump 30, in particular its pump chamber 39, to the atmosphere/environment and/or decreases the pressure in the air pump 30 or its pump chamber 39 to ambient pressure, preferably abruptly, e.g. within less than one second, preferably less than 0.5 seconds.

The control device 59, in particular pressure relief means 60, is preferably adapted to compensate the overpressure generated during the tensioning process and/or by the air pump 30 and, thus, helps to protect the nebulizer 1 and/or container 3 against damages that might be caused by a high air pressure maintained in the nebulizer 1, in particular pump chamber 39, and/or to prevent leakage of the nebulizer 1, e.g. after tensioning of the nebulizer without immediate nebulization.

With other words, the control device 59, in particular the pressure relief means 60, is preferably adapted to temporarily open the pump chamber 39, and/or to temporarily connect the air pump 30, in particular its pump chamber 39, to the atmosphere/environment, in particular at the end of the tensioning process. Thus, the pump chamber 39 is preferably only temporarily closed during the tensioning process.

Due to the control device 59 and/or the combination of the pressure relief means 60 on the one hand and the valve 40/control valve 44 on the other hand, the air pressure within the air pump 30 or its pump chamber 39 is limited/controlled by two different mechanisms during tensioning of the nebulizer 1. First, the air pressure is limited to a maximum value defined by the valve 40/control valve 44. Second, the air pressure is (abruptly) reduced to ambient pressure, when a predefined axial position of the pump piston 31 within the cylinder 32 is reached and/or when the tensioning process ends.

Further, the value of the air pressure within the air pump 30 or its pump chamber 39 is limited/controlled independent from the velocity of tensioning/cocking/loading of the nebulizer 1, i.e. the speed with which the housing part 18 is rotated relative to the upper housing part 16.

Figure 19:
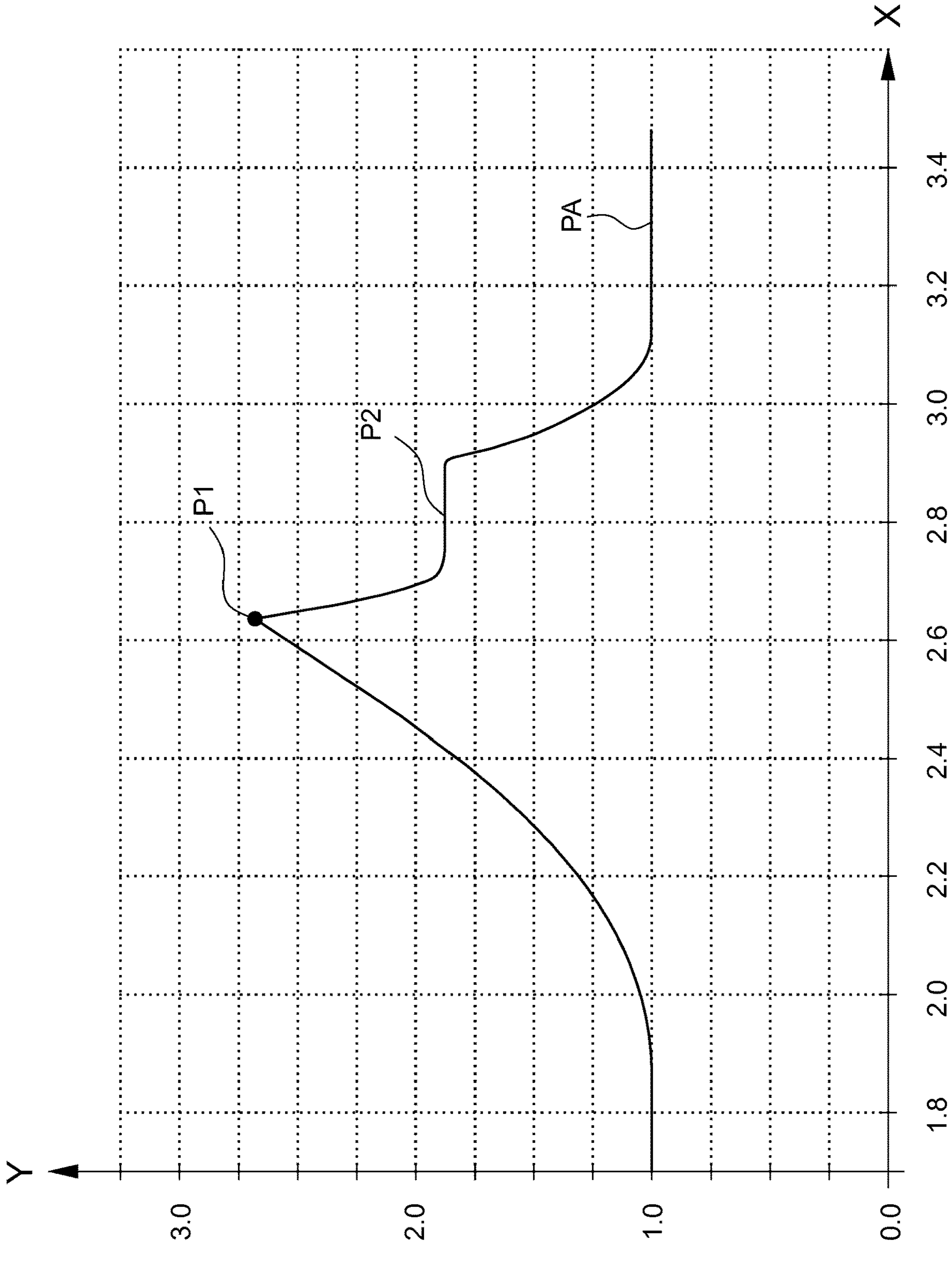
FIG. 19 a diagram of the pressure progression as a function of the axial location of the container.

FIG. 19 shows schematically in a diagram the pressure progression as a function of the axial position of the container 3 within the housing part 18 and/or of the pump piston 31 within the cylinder 32, in particular as a function of the axial displacement of the container 3 during the tensioning process starting from the non-tensioned state. The values shown have been determined experimentally.

The X-axis denotes the axial position or displacement of the container 3 and/or pump piston 31 in mm. It starts with "0" which means that the container 3 and/or pump piston 31 has not been moved out of its non-tensioned state, i.e. towards the bottom of the nebulizer 1 or housing part 18.

The Y-axis denotes the pressure in bar within the pump chamber 39. The pressure of 1.0 bar represents or corresponds to the normal pressure or ambient air pressure PA. Preferably, the pressure depends on the volume displaced by the pump piston 31.

During the tensioning process, the air pressure within the nebulizer 1, in particular air pump 30 or its pump chamber 39, increases, preferably until the first maximum value P1 is reached. In the present diagram, the first maximum value P1 is reached when the container 3 has been moved by approximately 2.65 mm.

The first maximum value P1 is preferably above the ambient pressure PA and/or above the second maximum value P2, mostly preferred above 2 bar and/or below 3 bar. In the present diagram, the first maximum value P1 corresponds to approximately 2.7 bar.

When the first maximum value P1 is reached, the valve 40/control valve 44 opens, in particular such that the pressure decreases until the second maximum value P2 is reached. In other words, for increasing air pressure in the air pump 30/pump chamber 39 the valve 40/control valve 44 opens at a first maximum (pressure) value P1 and in particular, for decreasing air pressure inside the air pump 30/pump chamber 39 the valve 40/control valve 44 closes at a second (pressure) value P2 which is lower than P1. Thus, the control valve 43 limits the air pressure acting on the fluid piston 28 and, thus, on the liquid 2 in the container 3 to a first maximum (pressure) value P1.

Preferably, the second maximum value P2 is above the ambient pressure PA and/or below the first maximum value P1, mostly preferred above 1 bar and/or below 2 bar. In the present diagram, the second maximum value P2 corresponds to 1.8 bar.

When the second maximum value P2 is reached, the valve 40/control valve 44 closes, preferably automatically, as already described. In particular, the valve 40/control valve 44 is closed when the air pressure within the air pump 30/pump chamber 39 is lower than a second value P2 which is lower than the first maximum value P1.

When a predefined/certain axial position of the cylinder 3 within the nebulizer 1 and/or of the pump piston 31 within the cylinder 32 is reached, in the diagram between 2.8 mm and 3 mm starting from the non-tensioned state, the control device 59 and/or pressure relief means 60 is activated/opened, in particular such that the air pressure within the air pump 30 and/or its pump chamber 39 is preferably abruptly decreased to ambient pressure PA, mostly preferred within less than one second, 0.5 seconds or 0.1 seconds, as already mentioned.

FIGS. 20 to 26 show a further embodiment of the nebulizer 1 and container 3.

Figure 20:
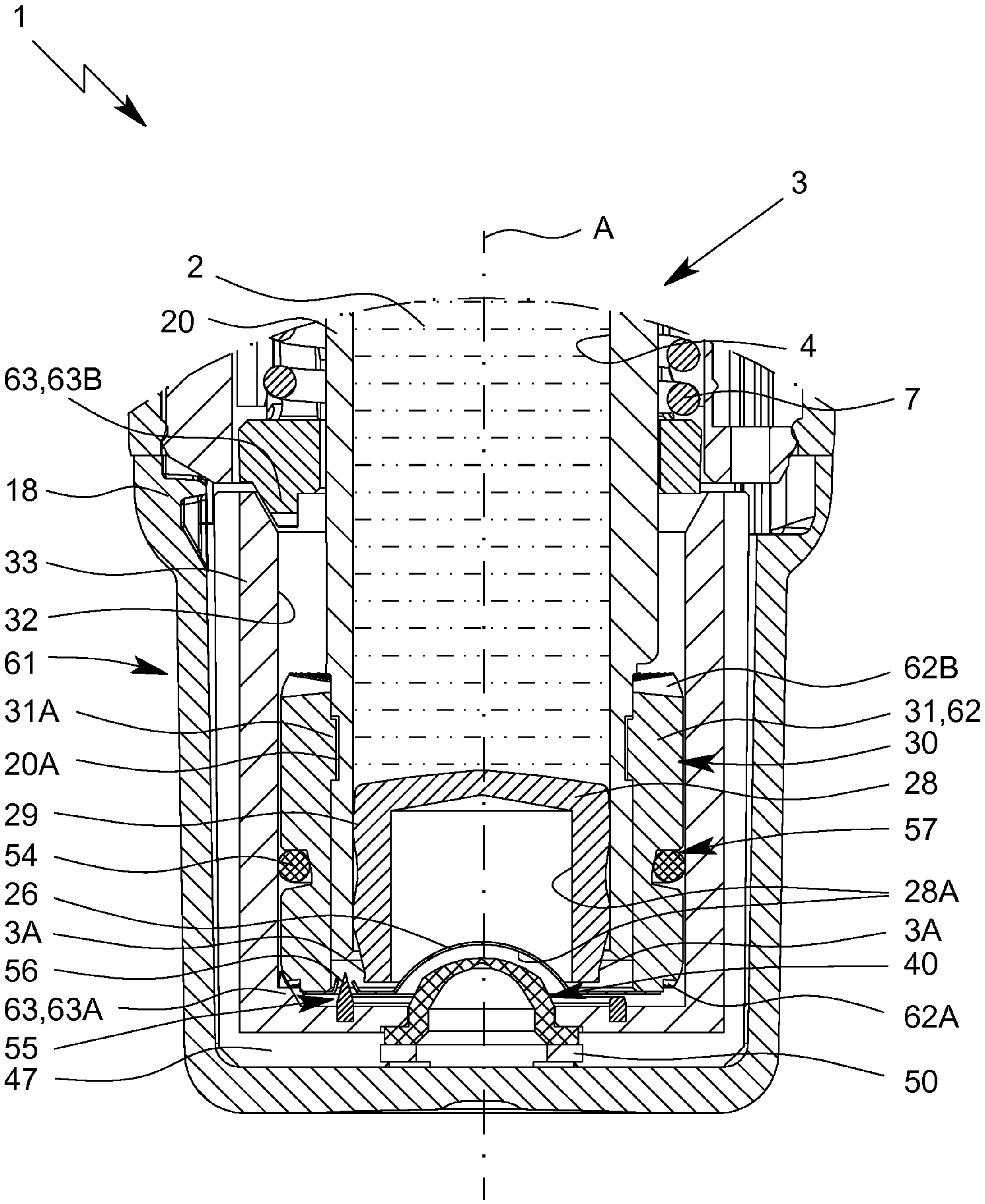
FIG. 20 a schematic section of a lower part of the nebulizer according to another embodiment in the tensioned state.
Figure 21:
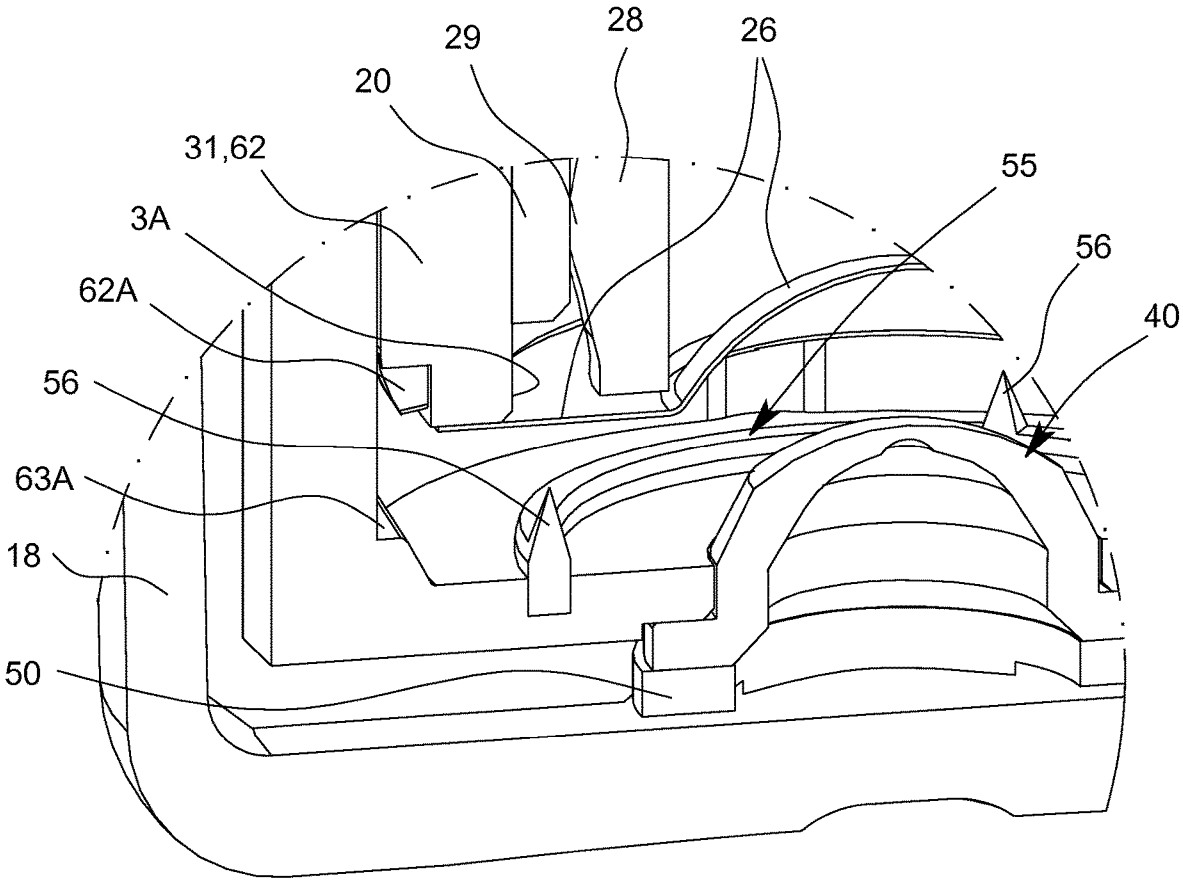
FIG. 21 a partial enlargement illustrating the nebulizer of FIG. 20 in the delivery state.
Figure 22:
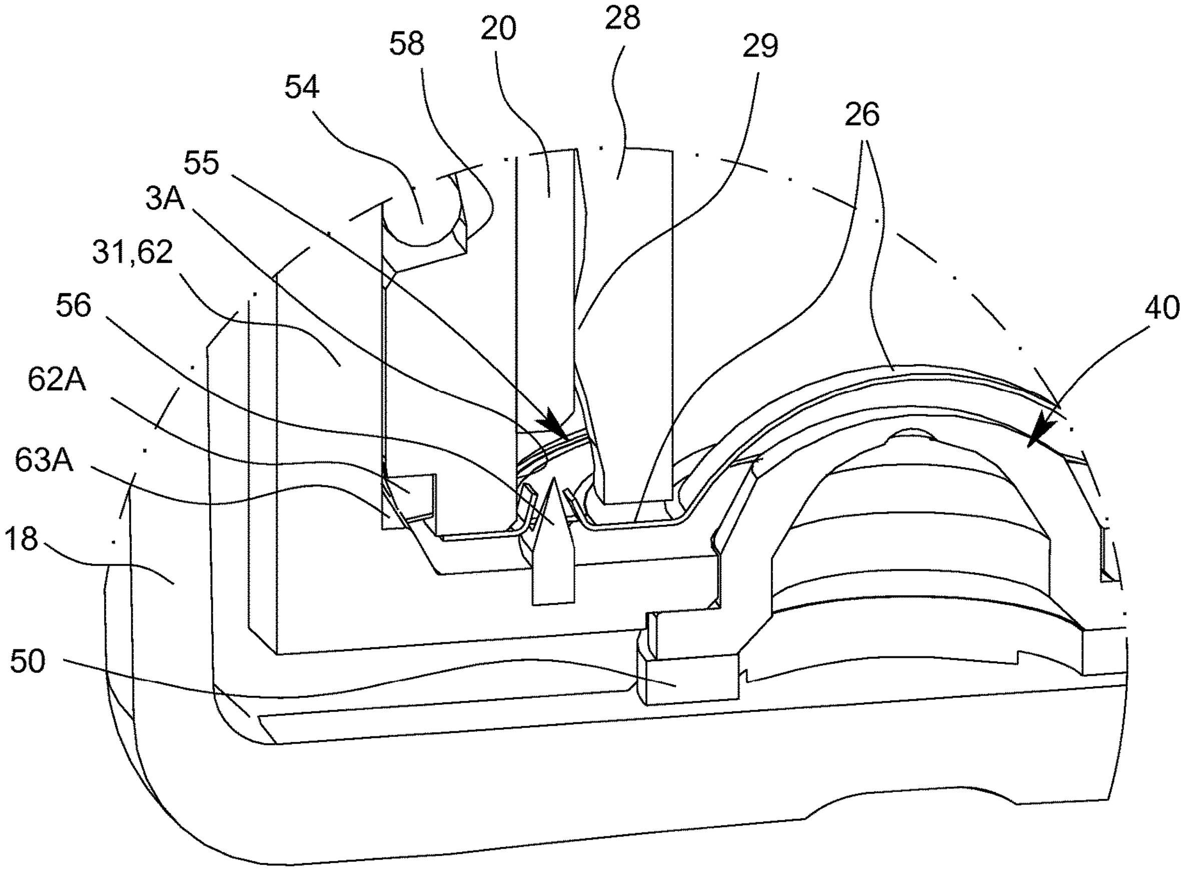
FIG. 22 a partial enlargement illustrating the nebulizer of FIG. 20 in the tensioned state.
Figure 23:
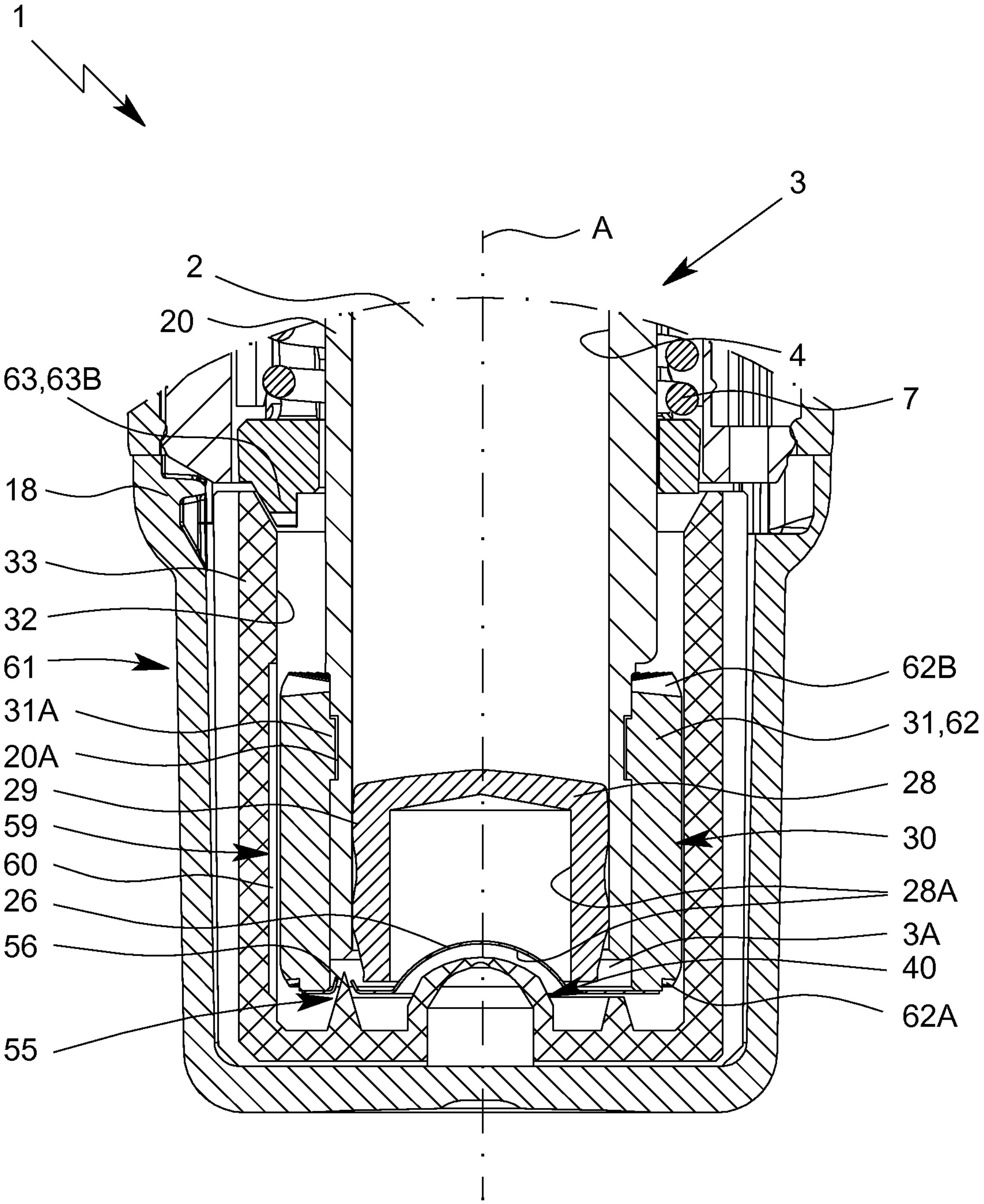
FIG. 23 a schematic section of a lower part of the nebulizer in the tensioned state similar to FIG. 20, but with a modified container.

FIG. 20 shows a schematic section of a lower part of the nebulizer 1 in the tensioned state. FIG. 21 shows a partial enlargement illustrating the nebulizer 1 of FIG. 20 in the delivery state. FIG. 22 shows a partial enlargement illustrating the nebulizer 1 after being tensioned for the first time. FIG. 23 shows a schematic section of a lower part of the nebulizer 1 in the tensioned state similar to FIG. 20, but with a modified container 3 and a modified air pump 30.

In contrast to the previous embodiment, the present embodiment shown in FIG. 20 comprises a fluid piston 28 that is formed integrally with the seal 29, e.g. by injection molding. With other words, the fluid piston 28 forms the seal 29, preferably by at least one radial protrusion extending around the fluid piston 28.

The term "integrally" preferably means that the components/parts in question are made of the same material and/or in one piece. In particular, the components/parts are (bi-) injection molded and/or manufactured from, e.g. shaped and/or milled out of, one single block.

Preferably, the fluid piston 28 is made of plastics, in particular of elastomer, thermoplastic and/or thermoset, mostly preferred of (synthetic) rubber, such as butyl rubber.

As already mentioned, the elasticity of the fluid piston 28 is (further) increased due to the first recess 28A, preferably such that the (additional) seal 29 can be omitted and/or that the fluid piston 28 can easily glide within the container 3 or its casing 20.

The (axial) seal 26 covers—in contrast to the previous embodiment—preferably the entire axial end of the container 3 and/or pump piston 31.

In particular in order to prevent any interference with the valve 40/control valve 44, the seal 26 is preferably curved, in particular concavely on a side facing the valve 40, inlet valve 43 and/or control valve 44. Preferably, the seal 26 is dome-like shaped and/or matches at least essentially the shape of the valve 40.

Mostly preferred, the seal 26 comprises or forms the (first) central recess 28A.

Preferably, the seal 26 is axially spaced apart from the valve 40, inlet valve 43 and/or control valve 44, in particular independent from the axial positon of the container 3 in the nebulizer 1 or housing 19 and/or even when the container 3 is in its lower/first axial (end) position, in particular such that air can flow between the valve 40, inlet valve 43 and/or control valve 44 on the one hand and the seal 26 on the other hand and/or from the valve 40, inlet valve 43 and/or control valve 44 through the at least one hole of the seal 26 that has been pierced into the seal 26 by means of the opening device 55.

Alternatively and/or additionally, the seal 26, in particular its surface, is provided with grooves, notches or the like, at least on a side facing the valve 40, inlet valve 43 and/or control valve 44, in order to allow air to flow between the valve 40, inlet valve 43 and/or control valve 44 on the one hand and the seal 26 on the other hand and/or from the valve 40, inlet valve 43 and/or control valve 44 through the at least one hole of the seal 26 that has been pierced into the seal 26 by means of the opening device 55.

Preferably, the seal 26—in contrast to the previous embodiment—is not attached/fixed to the fluid piston 28 and/or (only) attached/fixed to the pump piston 31 and/or casing 20, in particular such that the fluid piston 28 is movable relative to the seal 26.

The opening device 55, in particular its opening element 56, is preferably adapted to pierce/perforate the seal 26, in particular only locally/selectively, preferably such that at least one, preferably several holes are formed in the seal 26, in particular eccentrically, spaced apart from the central axis A and/or between the fluid piston 28 and the casing 20 or pump piston 31.

With other words, the central portion of the seal 26 remains connected to the edge portion of the seal 26, preferably wherein only the edge portion of the seal 26 is attached to the pump piston 31, as best seen in FIGS. 21 and 22.

Preferably, the opening device 55, in particular its opening element 56, pierces through the seal 26 into the gap between the casing 20 and fluid piston 28, in particular into the circumferential/circular recess 3A of the container 3, casing 20 and/or fluid piston 28, as already mentioned. Preferably, the casing 20 and/or the fluid piston 28 are/is accordingly inclined.

Preferably, the opening device 55 comprises or is formed by several, here three, opening elements 56, preferably wherein the opening elements 56 are embodied as spikes, mostly preferred annularly arranged and/or spaced apart around the circumference of the preferably ring-shaped opening device 55 (most preferably wherein the valve 40 is arranged within a ring defined by the opening device 55). In particular, the opening elements 56 are arranged around valve 40.

The opening device 55 and the valve 40 might be formed integrally, as shown in the embodiment according to FIG. 23.

Alternatively or additionally, the valve 40 and the (radial) seal 54 acting between the pump piston 31 and the cylinder 32 might be formed integrally.

Mostly preferred, the valve 40, the opening device 55, the cylinder 32, the control device 59, in particular the pressure relief means 60, and/or the seal 54 acting between the pump piston 31 and the cylinder 32 are formed integrally and/or in one piece, e.g. by injection molding. This allows an easy construction and/or an easy and/or quick assembly of the nebulizer 1.

Preferably, the pump piston 31 is rotatable relative to the container 3, in particular its casing 20. In particular, the pump piston 31 is rotatably held by or connected with the casing 20 of the container 3.

In the embodiment shown in FIGS. 20 to 26, the pump piston 31 is preferably clipped on the casing 20, in particular such that it can rotate relative to the casing 20.

Preferably, the pump piston 31 comprises a circumferential protrusion 31A and the casing 20 comprises a circumferential corresponding groove 20A or vice versa, preferably wherein the protrusion 31A is inserted into the groove 20A, in particular such that the pump piston 31 is axially held by means of the casing 20.

Preferably, the protrusion 31A and the groove 20A extend around the circumference of the pump piston 31 and the casing 20, respectively.

Preferably, the nebulizer 1 is at least partially reusable and/or can be used with several containers 3. Mostly preferred, the nebulizer 1 can be opened in order to replace/exchange the container 3, preferably by detaching the housing part 18. In particular, solutions are possible wherein the container 3 forms a unit and/or is replaced/exchanged together with the housing part 18, air pump 30 and/or insert 33.

As already mentioned, the total number of uses of the nebulizer 1 and/or the number of containers 3, which can be used with the same nebulizer 1, is preferably counted/indicated and/or restricted. The nebulizer 1 preferably comprises a device for counting and/or indicating the number of uses performed or still possible with the nebulizer 1 or for counting and/or indicating the number of containers 3 that have been used or still can be used with the (current) nebulizer 1. Such a device is shown in FIG. 1 and disclosed in WO 2004/024340 A1.

Preferably, the nebulizer 1 or the container 3 comprises an (additional) indicator device 61 for counting and/or indicating a number of uses performed or still possible with the (current) container 3 or volume 4, e.g. in order to indicate when the container 3 has to been exchanged/replaced.

Preferably, the nebulizer 1 might be equipped with both, a (first) indicator device 61 for counting and/or indicating a number of uses performed or still possible with the (current) container 3 or volume 4 and a (second) indicator device for counting and/or indicating a number of uses performed or still possible with the nebulizer 1 and/or for counting and/or indicating a number of container 3 that have been used or still can be used with the (current) nebulizer 1. However, both devices can be realized independent from one another.

The functionality of the indicator device 61 will be described in the following in particular with reference to FIG. 24, which shows a perspective view of the partially sectioned and illustrated nebulizer 1 in the non-tensioned state.

The indicator device 61 preferably comprises an indicator element 62 and an actuator 63 for actuating/indexing the indicator element 62.

Preferably, the indicator element 62 is arranged at the bottom/base 22 of the container 3. In particular, the indicator element 62 comprises or forms a first axial end and/or the bottom/base 22 of the container 3 and/or moves (axially) together with the container 3.

In particular, the indicator element 62 is rotatably connected/attached to the container 3, in particular its casing 20. Optionally, the indicator element 62 is only rotatable in one direction and/or secured against a rotation in one direction, e.g. by a ratchet or the like (not shown).

Preferably, the indicator element 62 is ring-shaped, cylindrical and/or extends around the container 3, in particular its casing 20. With other words, the indicator device 61, in particular its indicator element 62, surrounds the casing 20 radially.

Preferably, the indicator element 62 is embodied as a hollow cylinder and/or formed in one piece.

Mostly preferred, the indicator element 62 comprises or forms the pump piston 31 or vice versa.

The indicator element 62 preferably comprises a marking 62C for indicating the number of uses already performed or still possible with the respective container 3 or volume 4.

The marking 62C is preferably embodied as a numerical marking and/or a serial of numbers. However, other solutions are possible as well, e.g. wherein the marking 62C is embodied as a color gradient or the like.

Preferably, the indicator device 61 comprises an indicator housing 64, preferably wherein the indicator housing 64 is at least essentially cylindrical and/or has an at least essentially cylindrical form and/or wherein the indicator element 62 is enclosed within the indicator housing 64.

Preferably, the indicator housing 64 comprises a window 64A, in particular in its circumferential wall, preferably wherein the marking 62C indicating the current number of uses performed or still possible with the respective container 3 is visible through the window 64A for a user or patient.

The window 64A can be embodied as an opening within the indicator housing 64, preferably wherein in this case the window 64A is axially spaced apart from the pump chamber 39.

However, other constructional solutions are possible as well, e.g. wherein the window 64A is formed by a transparent portion of the indicator housing 64.

Preferably, the indicator housing 64 is rigidly/immovably connected to the cylinder 32, insert 33 and/or housing part 18. Mostly preferred, the indicator housing 64 is rotated together with the inner part 17, housing part 18, cylinder 32 and/or insert 33 and/or relative to the upper housing part 16 during tensioning of the nebulizer 1.

In particular, the housing part 18, cylinder 32 and/or the insert 33 comprises or forms the indicator housing 64, or vice versa.

The indicator device 61 preferably comprises the actuator 63 or cooperates with the actuator 63.

The actuator 63 is preferably rigidly/immovably connected/attached to the housing part 18, cylinder 32, insert 33 and/or indicator housing 64. Mostly preferred, the actuator 63 is rotated together with the inner part 17, housing part 18, cylinder 32, insert 33 and/or indicator housing 64 and/or relative to the upper housing part 16 during tensioning of the nebulizer 1.

In particular, the housing part 18, cylinder 32, insert 33 and/or indicator housing 64 comprises or forms the actuator 63.

Preferably, the container 3, in particular its casing 20, is rotated together with the inner part 17, housing part 18, cylinder 32, insert 33, actuator 63 and/or indicator housing 64 and/or relative to the upper housing part 16 during tensioning of the nebulizer 1.

Preferably, the container 3, in particular its casing 20, is—in particular radially and/or in a circumferential direction—hold by and/or—in particular axially—guided within the housing part 18, cylinder 32, insert 33, actuator 63 and/or indicator housing 64, in particular such that it can move axially within the housing part 18, cylinder 32, insert 33, actuator 63 and/or indicator housing 64 and/or such that it is moved/rotated together with the inner part 17, housing part 18, cylinder 32, insert 33, actuator 63 and/or indicator housing 64.

Mostly preferred, the torque is transmitted from the inner part 17, housing part 18, cylinder 32, insert 33, actuator 63 and/or indicator housing 64 to the container 3, in particular its casing 20, such that these components rotate together relative to the upper housing part 16 during tensioning of the nebulizer 1.

With other words, preferably only the indicator element 62 and/or the pump piston 31 can rotate relative to the inner part 17, housing part 18, cylinder 32, insert 33, actuator 63 and/or indicator housing 64.

Preferably, the container 3, in particular its casing 20, comprises a protrusion and the inner part 17, housing part 18, cylinder 32, insert 33, actuator 63 and/or indicator housing 64 comprises a corresponding recess (or vice versa), preferably wherein the protrusion protrudes into the recess, in particular such that container 3 cannot rotate but move axially relative to the inner part 17, housing part 18, cylinder 32, insert 33, actuator 63 and/or indicator housing 64. In this way, the container 3, in particular its casing 20, is preferably correctly orientated relative to the housing part 18, cylinder 32, insert 33, actuator 63 and/or indicator housing 64.

In the present embodiment, the container 3, in particular its casing 20, comprises a longitudinal protrusion and the actuator 63 comprises a corresponding recess, as best seen in FIG. 20. However, other constructional solutions are possible as well.

Preferably, the container 3 is already (pre-)inserted in the nebulizer 1, in particular its housing 19, in the delivery state of the nebulizer 1. However, other solutions are possible.

Preferably, the container 3 is exchanged/replaced/inserted together, i.e. as a unit, with the housing part 18, air pump 30, insert 33 and/or indicator device 61, in particular its housing 64, as already mentioned.

In order to orientate the indicator element 62 relative to the container 3, casing 20, housing part 18, insert 33 and/or indicator housing 64 (e.g. when a (new) container 3 is inserted into the nebulizer 1), the indicator element 62 on the one hand and the container 3, casing 20, housing part 18, insert 33 and/or indicator housing 64 on the other hand might be provided with marks. However, it is preferred that the indicator element 62 is already orientated correctly in the delivery state of the container 3 or of the unit formed by the container 3, housing part 18, air pump 30, insert 33 and/or indicator device 61.

The actuator 63 is preferably adapted to directly or indirectly, e.g. via a transmission, actuate or index, in particular rotate, the indicator element 62, preferably stepwise/incrementally and/or by counting/actuation/indexing steps.

The term "actuate" or "index" means preferably that the indicator element 62 is moved/rotated forward or in increments or complete (counting) steps, in particular for counting and/or indicating the number of uses performed or still possible with the container 3. Mostly preferred, "actuate" or "index" means that the indicator element 62 is incrementally/stepwise rotated relative to the casing 20, housing part 18, cylinder 32, insert 33 and/or indicator housing 64, in particular in order to count a single use of the nebulizer 1, i.e. the withdrawal and dispensing of dose of the liquid 2.

Preferably, only a complete withdrawal and/or nebulization of a dose of the liquid 2 and/or a complete use performed is counted as a counting step.

The actuator 63 is preferably adapted to index/actuate the indicator element 62, in particular completely, (only) when the container 3, the pump piston 31 and/or the indicator element 62 reaches its first/lower axial (end) position and, further, its second/upper axial (end) position and/or has reached both axial (end) positions.

Preferably, the first/lower axial (end) position of the container 3, pump piston 31 and/or the indicator element 62 is the position in which the container 3, pump piston 31 and/or the indicator element 62 is axially moved as far away as possible from the mouthpiece 13 and/or as close as possible to the bottom of the housing part 18, cylinder 32 and/or insert 33 and/or in which the volume of the pump chamber 39 is minimized and/or in which tensioning of the nebulizer 1 is completed, as shown in FIG. 20.

Figure 24:
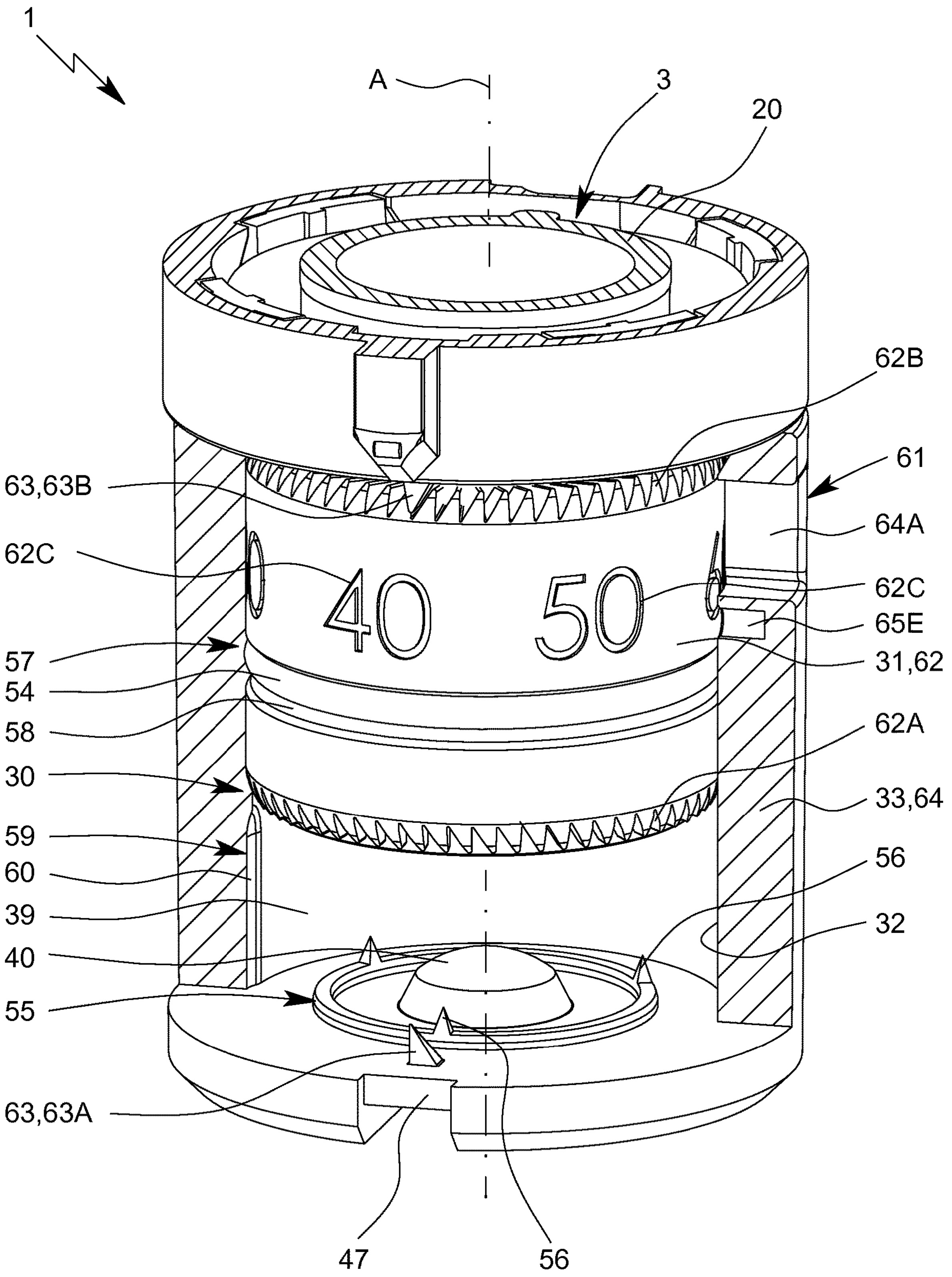
FIG. 24 a perspective view of the partially sectioned and illustrated nebulizer according to FIG. 20 in the non-tensioned state.

The second/upper axial (end) position of the container 3, pump piston 31 and/or the indicator element 62 is preferably the position of the container 3, pump piston 31 and/or indicator element 62 in which the container 3, pump piston 31 and/or indicator element 62 is moved as close as possible to the mouthpiece 13 and/or as far as possible from the bottom of the housing part 18, cylinder 32 and/or insert 33 and/or in which the volume of the pump chamber 39 is maximized and/or in which nebulization process is completed, as shown in FIG. 24.

Mostly preferred, the container 3, pump piston 31 and/or indicator element 62 come (s) into contact or engages with the actuator 63 in the first/lower axial (end) position and in the second/upper axial (end) position.

The actuator 63 preferably comprises a first actuating element 63A and a second actuating element 63B, preferably wherein the actuating elements 63A, 63B are spaced apart axially from one another and/or orientated in opposite axial directions.

Preferably, the actuator 63 is a multi-part, in particular two-part, component and/or is assembled by several, in particular two, components, preferably wherein different components comprise or form the actuating elements 63A, 63B and/or wherein the actuating elements 63A, 63B each forms a different component.

Preferably, the first actuating element 63A is preferably rigidly/immovably connected/attached to the housing part 18, cylinder 32, insert 33 and/or indicator housing 64. In particular, the housing part 18, cylinder 32, insert 33 and/or indicator housing 64 comprises or forms only the first actuating element 63A. Mostly preferred, the housing part 18, cylinder 32, insert 33 and/or indicator housing 64 are formed integrally with the first actuating element 64A.

Preferably, the second actuating element 63B is preferably rigidly/immovably connected/attached to the housing part 18, cylinder 32, insert 33 and/or indicator housing 64. In particular, the second actuating element 63B comprises or forms a cap and/or a (radial) bearing part for the container 3 and/or a (axial) bearing part for the drive spring 7.

Preferably, the second actuating element 63B is axially connected to, in particular inserted into, the housing part 18, cylinder 32, insert 33 and/or indicator housing 64, preferably in a form-fit or force-fit manner, as best seen in FIGS. 20 and 23.

Preferably, the first actuating element 63A is adapted to index/actuate/rotate the indicator element 62, in particular halfway and/or half a (counting) step forward, (only) in the first/lower axial (end) position and/or when the container 3, pump piston 31 and/or the indicator element 62 has reached the first/lower axial (end) position and/or when the indicator element 62 comes into contact/engages with the first actuating element 63A.

Preferably, the second actuating element 63B is adapted to index/actuate/rotate the indicator element 62, in particular halfway and/or half a (counting) step forward, (only) in the second/upper axial (end) position and/or when the container 3, pump piston 31 and/or the indicator element 62 has reached the second/upper axial (end) position and/or when the indicator element 62 comes into contact/engages with the second actuating element 63B, as shown in FIG. 24.

Preferably, the actuating element 63A, 63B are embodied as (axial)—preferably inclined—protrusions that extend in the direction of the indicator element 62.

Mostly preferred, the actuating elements 63A, 63B only interact with the indicator element 62 when the latter approaches the first/lower and second/upper axial (end) position, respectively.

The indicator element 62 preferably comprises at least one gear ring 62A, 62B having a plurality of (inclined) teeth, in particular wherein the gear ring 62A, 62B is arranged on a front face/surface of the indicator element 62 and/or around the casing 20.

Due to the inclination of the gear ring 62A, 62B, in particular its teeth, and/or of the actuating element(s) 63A, 63B an axial movement of the container 3 is transformed in a rotational movement of the indicator element 62. In particular, the indicator element 62 is rotated and/or driven by the actuator 63 when the actuating element(s) 63A, 63B, in particular the inclined surface thereof, and the gear ring 62A, 62B, in particular the inclined surface of the tooth being in contact with the actuating element(s) 63A, 63B, glide past each other.

Preferably, the indicator element 62 comprises a first gear ring 62A and a second gear ring 62B, preferably wherein the gear rings 62A, 62B are spaced apart axially from one another and/or orientated in opposite axial directions. Mostly preferred, the gear rings 62A, 62B are formed integrally.

Preferably, the first gear ring 62A interacts (directly) with the first actuating element 63A when the indicator element 62 approaches the first/lower axial (end) position.

Preferably, the second gear ring 62B interacts (directly) with the second actuating element 63B when the indicator element 62 approaches the second/upper axial (end) position, as shown in FIG. 24.

Mostly preferred, the indicator device 61 is adapted to carry out a complete indexing/actuation/counting step and/or to count the withdrawal and/or nebulization of a dose of the liquid 2 only when the nebulizer 1 has been tensioned/loaded completely and, further, when the dispensing process has been completed successively (i.e. when the nebulization has taken place).

In particular, the indicator device 61 only completes an indexing/actuation step and/or only counts the withdrawal and/or nebulization of a dose of the liquid 2, when the container 3, pump piston 31 and/or the indicator element 62 has reached both axial (end) positions successively.

With other words, the movement of the container 3, pump piston 31 and/or the indicator element 62 into its first/lower axial position or into its second/upper axial position causes only that the indicator element 62 is moved/rotated halfway and/or by half a (counting) step forward. In this way, an uncompleted tensioning of the nebulizer 1—even when performed several times in a row—is not counted as a usage of the nebulizer 1/container 3 and, thus, does not contribute to/manipulate the indicated number of uses performed or still possible with the container 3 or volume 4. Thus, an improper handling of the nebulizer 1 will not result in a wrong counting.

As already mentioned, the indicator element 62 preferably comprises or forms the pump piston 31 or vice versa.

Preferably, the indicator housing 64 comprises or forms the cylinder 32 or vice versa.

In particular, the (axial) movement of the pump piston 31 is used for the actuation of the indicator device 61, i.e. the indicator element 62, and/or for counting or indicating the number of uses performed or still possible with the container 3.

With other words, the indicator device 61 is preferably integrated into the air pump 30 and/or actuated together with and/or driven by the air pump 30. This allows a simple construction of the nebulizer 1.

The nebulizer 1, in particular indicator device 61, preferably comprises a blocking device 65, in particular wherein the blocking device 65 is adapted to block a further use of the nebulizer 1 or container 3 in a locked state, preferably when a predetermined number of uses has been reached or exceeded with the current container 3.

Mostly preferred, the container 3 can (only) be removed/exchanged together with the housing part 18, air pump 30, insert 33, indicator device 61 and/or blocking device 65.

The functionality of the blocking device 65 will be described in the following with reference to FIGS. 25 and 26, which show a section of the partially illustrated nebulizer 1 in the direction of the axis A.

Preferably, the blocking device 65 is integrated in the indicator device 61, in particular in the indicator element 62.

The blocking device 65 preferably comprises a first blocking element 65A, a second blocking element 65B and/or a spring 65C, preferably wherein the spring 65C is arranged between the first blocking element 65A and the second blocking element 65B and/or presses against both blocking elements 65A, 65B.

Preferably, the indicator device 61, in particular indicator element 62, comprises an opening 65D, preferably wherein the blocking device 65 is at least partially arranged in the opening 65D and/or wherein the opening 65D extends radially and/or from one side to the other in the indicator element 62.

Mostly preferred, the blocking device 65 is rotated together with the indicator element 62. However, other constructional solutions are possible as well, e.g. wherein the blocking device 65 is arranged in the casing 20 and/or insert 33.

Preferably, the spring 65C presses the first blocking element 65A against the housing part 18, cylinder 32, insert 33 and/or indicator housing 64 and/or presses the second blocking element 65B against the container 3, in particular its casing 20.

Preferably, the force exerted by the spring 65C does not interfere with the movement of the indicator element 62 or pump piston 31 relative to the container 3, casing 20, housing part 18, cylinder 32, insert 33 and/or indicator housing 64.

Figure 25:
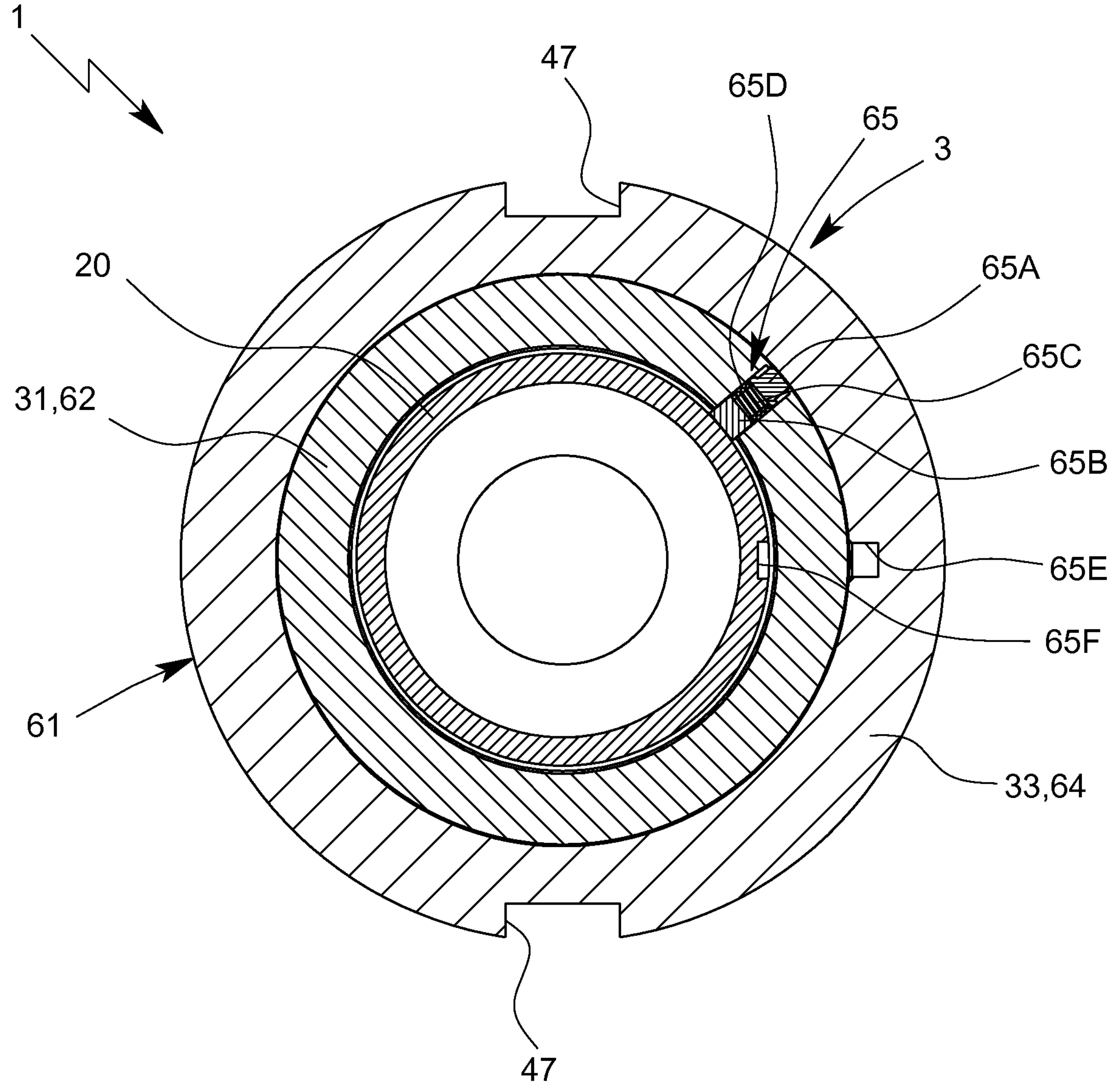
FIG. 25 a schematic section of the partially illustrated nebulizer according to FIG. 20 illustrating a blocking device for blocking an indicator device.
Figure 26:
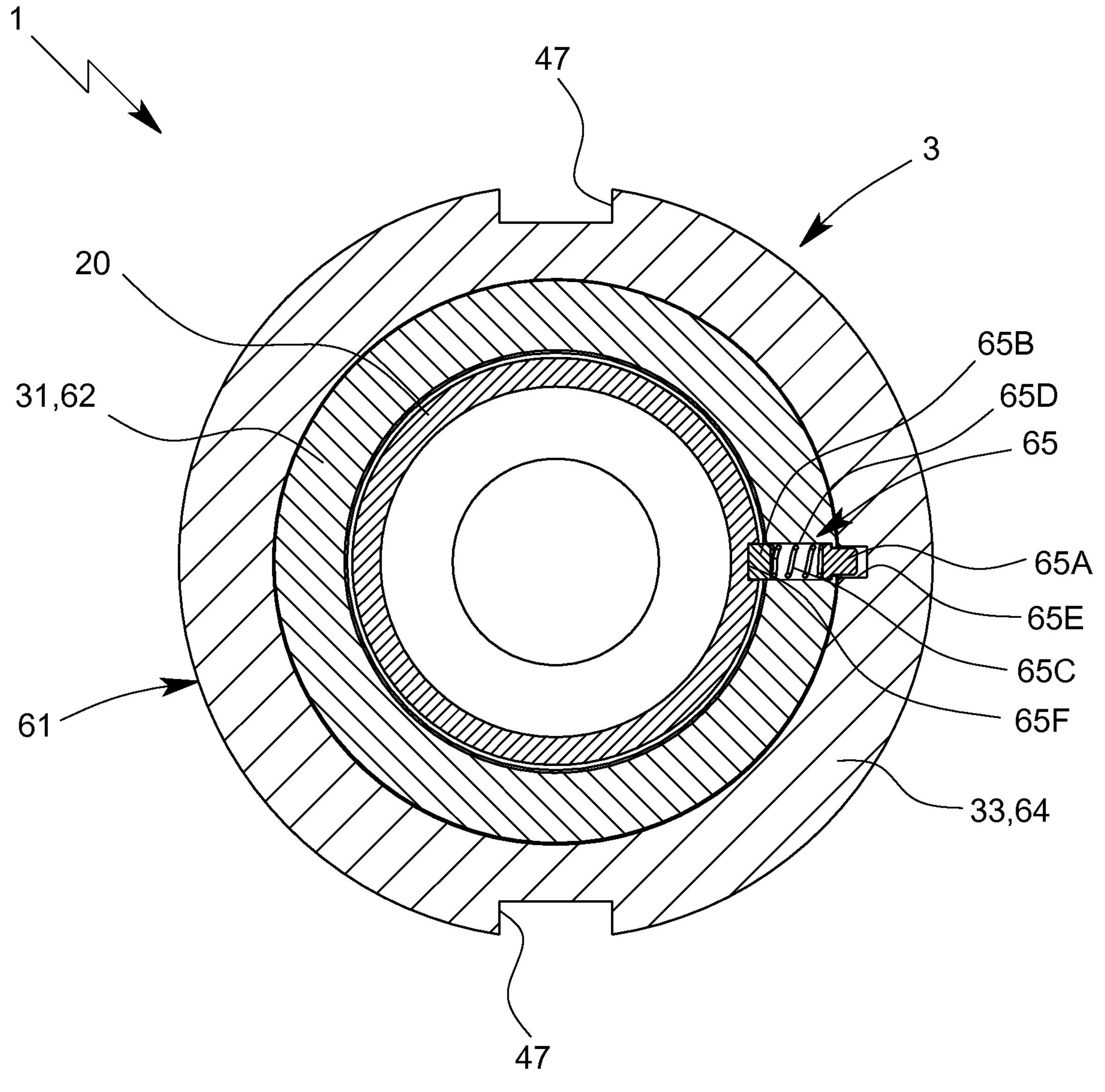
FIG. 26 a schematic section of the partially illustrated nebulizer according to FIG. 25 in the blocked state.

FIG. 25 shows the blocking device 65 in the unlocked state, i.e. when movement of the indicator device 61 or pump piston 31 relative to the container 3, casing 20, cylinder 32, insert 33 and/or indicator housing 64 is possible and/or not blocked by the blocking device 65.

When a certain number of actuations, operations or discharge doses of the liquid 2 has been reached or exceeded, in particular when the indicator element 62 has been rotated by more than 180° or 270° and/or less than 350° (starting from the delivery/unused state of the nebulizer 1), the blocking device 65 blocks/locks the nebulizer 1 against a (further) actuation or use. The locked state of the nebulizer 1 is shown in FIG. 26.

The indicator element 62 can be rotated around the axis A and/or relative to the container 3, casing 20, housing part 18, cylinder 32, insert 33 and/or indicator housing 64 until the blocking device 65, in particular its blocking elements 65A, 65B, engage(s)—preferably in a form-fit manner—with the container 3, housing part 18, casing 20, cylinder 32, insert 33 and/or indicator housing 64.

Preferably, the housing part 18, cylinder 32, insert 33 and/or indicator housing 64 comprises a first recess 65E and/or the container 3, in particular the casing 20, comprises a second recess 65F, preferably wherein the first recess 65E is adapted to receive the first blocking element 65A and the second recess 65F is adapted to receive the second blocking element 65B, at least in the locked state and/or when a predetermined number of uses has been reached or exceeded with the current container 3.

With other words, the blocking device 65 is adapted to establish a form-fit connection between the pump piston 31/indicator element 62 and the container 3/casing 20 on the one hand, in particular by pushing the second blocking element 65B into the second recess 65F, and between the pump piston 31/indicator element 62 and the housing part 18/cylinder 32/insert 33/indicator housing 64 on the other hand, in particular by pushing the first blocking element 65A into the first recess 65E.

Individual features, aspects and/or principles of the embodiments described may also be combined with one another as desired and may be used particularly in the shown nebulizer 1, but also in similar or different nebulizers.

Unlike freestanding equipment or the like the proposed nebulizer 1 is preferably designed to be portable and in particular is a mobile hand operated device.

The proposed solution may, however, be used not only in the nebulizers 1 specifically described here but also in other nebulizers or inhalers or in other devices for the delivery of liquid formulations.

Preferably, the liquid 2 is especially an aqueous pharmaceutical formulation or an ethanolic pharmaceutical formulation. However, it may also be some other pharmaceutical formulation, a suspension or the like.

Preferably, the expression liquid is to be broadly understood to encompass any kinds of such as suspensions, solutions, liquefied formulations and the like.

Preferably, the liquid 2 has low vapor pressure and/or high boiling point, in particular higher than 80° C. or 90° C.

Preferably, the liquid 2 is propellant-free.

Preferred ingredients and/or formulations of the preferably medicinal liquid 2 are listed in particular in WO 2009/115200 A1, preferably on pages 25 to 40, or in EP 2 614 848 A1, paragraphs 0040 to 0087, which are incorporated herewith by reference. In particular, these may be aqueous or non-aqueous solutions, mixtures, formulations containing ethanol or free from any solvent, or the like.

Additional Embodiments and/or Combinations

Further, independent aspects of the present invention are listed in the following:

1. Nebulizer (1) for nebulizing a liquid (2), comprising:
   a preferably replaceable container (3) containing multiple doses of the liquid (2);
   a fluid pump (5) for withdrawing a dose of the liquid (2) from the container (3) and pressurizing the respective dose for nebulization;
   an air pump (30) associated to the container (3) for pressurizing the liquid (2) in the container (3) to help withdrawing the liquid (2) in doses from the container (3); and
   preferably a housing part (18) which can be detached from the nebulizer (1) or opened for inserting or replacing the container (3);
   characterized in that the nebulizer (1) or air pump (30) comprises a control valve (44) limiting the air pressure acting on the liquid (2) in the container (3) to a maximum value above the ambient pressure independently from a filling level of the container (3) with the liquid (2), and/or that the container (3) is constructed according to any one of aspects 11 to 15.
2. Nebulizer according to aspect 1, characterized in that the nebulizer (1) or air pump (30) comprises an inlet valve (43) preventing any underpressure in the air pump (30) or its pump chamber (39).
3. Nebulizer according to aspect 2, characterized in that the control valve (44) and the inlet valve (43) are formed by the same valve (40) or valve element (42).
4. Nebulizer according to any one of the preceding aspects, characterized in that the air pump (30) is actuated by a relative movement of the container (3) within a housing (19) of the nebulizer (1).

5. Nebulizer according to any one of the preceding aspects, characterized in that the container (3) is moveable preferably stroke-like in the nebulizer (1) when withdrawing a dose of liquid (2) and/or when pressurizing or dispensing a dose of the liquid (2).
6. Nebulizer according to any one of the preceding aspects, characterized in that during use of the nebulizer (1), the air pump (30) and the fluid pump (5) pressurize alternately, in particular the air pump (30) pressurizes air when tensioning or loading the nebulizer (1) and the fluid pump (5) pressurizes a dose of liquid (2) when dispensing or nebulizing the dose of liquid (2).
7. Nebulizer according to any one of the preceding aspects, characterized in that the container (3) comprises a collapsible bag (4) containing the liquid (2).
8. Nebulizer according to any one of aspects 1 to 7, characterized in that the container (3) comprises a rigid casing (20) and a fluid piston (28) moveable therein forming a space for directly receiving the liquid (2).
9. Nebulizer according to any one of the preceding aspects, characterized in that the air pump (30) comprises or forms a piston/cylinder arrangement for pumping air to help withdrawing the liquid (2) in doses from the container (3).
10. Nebulizer according to any one of the preceding aspects, characterized in that the air pump (30) is arranged in the container (3) or forms an inseparable assembly with the container (3).
11. Container (3) containing multiple doses of a liquid (2) for nebulizing by a nebulizer (1), the container (3) comprising an air pump (30) in the container (3) for pressurizing the liquid (2) in the container (3) to help withdrawing the dose of the liquid (2) from the container (3), wherein the air pump (30) comprises a pump piston (31) and a return spring (36), characterized in that the return spring (36) is arranged between the pump piston (34) and a collapsible volume (4) of the container (3), and/or that the container (3), air pump (30) or pump piston (31) comprises an actuation element (51) for actuating the pump piston (31), and/or that the container (3), air pump (30) or pump piston (31) comprises a valve (40) for controlling or limiting the air pressure acting on the liquid (2) in the container (3) and/or preventing any underpressure in the air pump (30) or a pump chamber (39) thereof.

12. Container according to aspect 11, characterized in that the container (3) comprises a rigid casing (20) and a fluid piston (28) moveable therein forming the collapsible volume (4) of the container (3).
13. Container according to aspect 11 or 12, characterized in that the valve (40) comprises or forms a control valve (44) limiting the air pressure acting on the liquid (2) in the container (3) to a maximum value above the ambient pressure independently from the filling level of the container (3) with the liquid (2).
14. Container according to any one of aspects 11 to 13, characterized in that the valve (40) comprises or forms an inlet valve (43) preventing any underpressure in the air pump (30) or its pump chamber (39).
15. Container according to any one of aspects 11 to 14, characterized in that the container (3) comprises a bearing part (37) holding one end of the return spring (36) and/or forming an axial stop for a fluid piston (28) of the container (3).

LIST OF REFERENCE NUMERALS

1 nebulizer
2 liquid
3 container
3A recess (of container)
4 variable/collapsible volume
5 pressure generator/fluid pump
6 holder
7 drive spring
8 blocking element
9 conveying tube
10 non-return valve
11 pressure chamber
12 nozzle
13 mouthpiece
14 aerosol
15 air supply opening
16 upper housing part
17 inner part
17A upper part of inner part
17B lower part of inner part
17C retaining element
18 housing part (lower part)
18A aeration device
18B recess (of housing part)
19 nebulizer housing
20 (outer) casing
20A groove (of casing)
21 head
22 base
23 venting hole
24 shell/inner housing
25 closure
26 seal (of container)
27 venting opening
28 fluid piston
28A first recess (of fluid piston)
28B second recess (of fluid piston)
29 seal (of fluid piston)
30 air pump
31 pump piston
31A protrusion (of pump piston)
32 cylinder
33 insert
33A stop
33B protrusion (of insert)
34 port
35 seal (of port)
36 return spring
37 bearing part
38 bearing part
39 pump chamber
40 valve
41 leakage passage
42 valve element
42A flexible portion
43 inlet/check valve
44 control valve
45 opening
46 channel
47 channel
48 outlet opening
49 modified end
50 support/throttle element
51 actuation element
52 venting passage

53 central opening
54 seal (of pump piston)
55 opening device
56 opening element
57 sealing device
58 groove
59 pressure control device
60 pressure relief means
61 indicator device
62 indicator element
62A first gear ring
62B second gear ring
62C marking
63 actuator
63A first actuating element
63B second actuating element
64 indicator housing
64A window
65 blocking device
65A first blocking element
65B second blocking element
65C spring (of blocking device)
65D opening
65E first recess
65F second recess
A axis
C curve
PA ambient pressure
P1 first maximum value
P2 second maximum value
X axis
Y axis

The invention claimed is:

1. A nebulizer (1) for nebulizing a liquid (2), comprising:

a replaceable container (3) containing multiple doses of the liquid (2), a fluid pump (5) for withdrawing a dose of the liquid (2) from the container (3) and pressurizing the respective dose for nebulization, an air pump (30) for pressurizing the liquid (2) in the container (3) to help withdrawing the liquid (2) in doses from the container (3), and a housing part (18) which is detachable from the nebulizer (1) or opened for inserting or replacing the container (3), wherein the nebulizer (1) or the air pump (30) comprises a control valve (44) adapted to limit the air pressure generated by the air pump (30) for pressurizing the liquid (2) in the container (3) to one or more values above ambient pressure (PA) independently from a filling level of the container (3) with respect to the liquid (2).

2. The nebulizer (1) according to claim 1, wherein the nebulizer (1) or the air pump (30) comprises a pressure relief means (60) to decrease the air pressure acting on the liquid (2) in the container (3), wherein the pressure relief means (60) is adapted to open automatically dependent on the position of the container (3) within the nebulizer (1).

3. The nebulizer (1) according to claim 1, wherein the air pump (30) comprises a pump piston (31) and a cylinder (32) cooperating with the pump piston (31), and wherein the container (3), the air pump (30) or the pump piston (31) comprises a further valve (40) for preventing any underpressure in the air pump (30) or a pump chamber (39) thereof.

4. The nebulizer according to claim 1, wherein the control valve (44) is adapted to open automatically when the air pressure in the air pump (30) exceeds a first maximum value (P1) above the ambient pressure (PA).

5. The nebulizer according to claim 4, wherein the control valve (44) is adapted to close automatically when the air pressure in the air pump (30) decreases or corresponds to a second maximum value (P2) above the ambient pressure (PA).

6. The nebulizer according to claim 1, wherein at least one of:

the nebulizer (1) or air pump (30) comprises an inlet valve (43) preventing any underpressure in the air pump (30) or a pump chamber (39) thereof, the inlet valve (43) is adapted to open automatically when the air pressure in the air pump (30) is below the ambient pressure (PA), and the inlet valve (43) is adapted to close automatically when the air pressure in the air pump (30) increases or corresponds to the ambient pressure (PA).

7. The nebulizer according to claim 6, wherein the control valve (44) and the inlet valve (43) are formed at least one of: integrally, by a same valve (40), and by a same valve element (42).

8. The nebulizer according to claim 1, wherein the control valve has a dome shape.

9. The nebulizer according to claim 1, wherein the control valve is embodied as a duckbill valve.

10. The nebulizer according to claim 1, wherein the control valve comprises flexible portions (42A).

11. The nebulizer according to claim 10, wherein the flexible portions (42A) are adapted to open towards the interior of the air pump (30) in order to allow ambient air to flow into the air pump (30) and/or that the portions (42A) are adapted to open away from the interior of the air pump (30) in order to allow air to flow out of the air pump (30).

12. The nebulizer according to claim 1, wherein the air pump (30) is actuated by a relative movement of the container (3) within a housing (19) of the nebulizer (1) and/or that the container (3) is axially moveable in the nebulizer (1) when at least one of: withdrawing a dose of liquid (2), and pressurizing or dispensing a dose of the liquid (2).

13. The nebulizer according to claim 1, wherein during use of the nebulizer (1), the air pump (30) and the fluid pump (5) pressurize alternately.

14. The nebulizer according to claim 1, wherein the air pump (30) comprises or forms a piston/cylinder arrangement for pumping air to help withdrawing the liquid (2) in doses from the container (3), where the piston/cylinder arrangement comprises a pump piston (31) and a cylinder (32), wherein the pump piston (31) is axially moveable within the cylinder (32).

15. The nebulizer according to claim 1, wherein the container (3) comprises a collapsible bag (4) containing the liquid (2).

16. The nebulizer according to claim 1, wherein the container (3) comprises a rigid casing (20) and a fluid piston (28) moveable within the casing (20).

17. The nebulizer according to claim 16, wherein the fluid piston (28) and the casing (20) form a volume (4) containing the liquid (2), wherein the volume (4) is reduced or reducible by an axial movement of the fluid piston (28) within the casing (20).

18. The nebulizer according to claim 16, wherein at least one of:

the fluid piston (28) comprises a first central recess (28A) on a side turned away from a volume (4) for receiving the control valve (44), an inlet valve (43) and/or a further valve (40), and the fluid piston (28) comprises a second central recess (28B) on a side facing the volume (4).

19. The nebulizer according to claim 1, wherein the air pump (30) is arranged in the container (3) or forms an inseparable assembly with the container (3).

20. The nebulizer according to claim 1, wherein the nebulizer (1) or air pump (30) comprises pressure relief means (60) including an overpressure valve, to decrease the air pressure acting on the liquid (2) in the container (3), wherein the pressure relief means (60) is adapted to open automatically dependent on an axial position of the container (3) within a pump piston (31) within a cylinder (32).

21. The nebulizer according to claim 20, wherein the pressure relief means (60) is embodied as a bypass channel integrated into at least one of: the air pump (30), the pump piston (31) thereof, and the cylinder (32) thereof.

22. The nebulizer according to claim 1, wherein the container (3), comprises a seal (26) that seals the axial end of the container (3).

23. The nebulizer according to claim 22, wherein at least one of:

the seal (26) is curved, the seal (26) is curved concavely on a side facing a further valve (40), an inlet valve (43) and/or the control valve (44), and the seal (26) comprises the first central recess (28A).

24. The nebulizer according to claim 22, wherein the air pump (30) or the housing part (18), comprises or forms an opening device (55) adapted to open the seal (26).

25. The nebulizer according to claim 24, wherein at least one of:

the opening device (55) comprises at least one opening element (56) in order to pierce the seal (26), and the opening element (56) is embodied as a spike and/or radially spaced apart from at least one of the central axis (A) of the nebulizer (1) and the control valve (43).

26. The nebulizer according to claim 1, wherein a cylinder (32), the control valve, an inlet valve, a seal (54) acting between a pump piston (31) and the cylinder (32) and/or an opening device (55) are formed integrally.

* * * * *